US011684660B2

(12) United States Patent
Kaumaya et al.

(10) Patent No.: US 11,684,660 B2
(45) Date of Patent: Jun. 27, 2023

(54) HUMAN PD1 PEPTIDE VACCINES AND USES THEREOF

(71) Applicants: OHIO STATE INNOVATION FOUNDATION, Columbus, OH (US); MAYO FOUNDATION FOR MEDICAL EDUCATION AND RESEARCH, Rochester, MN (US)

(72) Inventors: Pravin T. P. Kaumaya, Westerville, OH (US); Tanios Bekaii-Saab, Scottsdale, AZ (US)

(73) Assignees: OHIO STATE INNOVATION FOUNDATION, Columbus, OH (US); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 685 days.

(21) Appl. No.: 16/498,929

(22) PCT Filed: Mar. 28, 2018

(86) PCT No.: PCT/US2018/024831
§ 371 (c)(1),
(2) Date: Sep. 27, 2019

(87) PCT Pub. No.: WO2018/183488
PCT Pub. Date: Oct. 4, 2018

(65) Prior Publication Data
US 2020/0197498 A1 Jun. 25, 2020

Related U.S. Application Data

(60) Provisional application No. 62/477,895, filed on Mar. 28, 2017.

(51) Int. Cl.
*A61K 38/00* (2006.01)
*A61K 39/00* (2006.01)
*A61P 35/00* (2006.01)
*C07K 14/705* (2006.01)
*C07K 16/28* (2006.01)

(52) U.S. Cl.
CPC ............ *A61K 39/001106* (2018.08); *A61K 39/001129* (2018.08); *A61P 35/00* (2018.01); *C07K 14/70503* (2013.01); *C07K 16/2803* (2013.01); *A61K 2039/55566* (2013.01); *A61K 2039/572* (2013.01); *A61K 2039/575* (2013.01); *A61K 2039/6075* (2013.01)

(58) Field of Classification Search
CPC ............................ A61K 38/00; A61K 39/0011
See application file for complete search history.

(56) References Cited

U.S. PATENT DOCUMENTS

| 3,610,795 A | 10/1971 | Antoine |
| 4,342,566 A | 8/1982 | Theofilopoulos et al. |
| 5,804,440 A | 9/1998 | Burton et al. |
| 6,096,441 A | 8/2000 | Hauser et al. |
| 7,691,396 B2 | 4/2010 | Kaumaya et al. |
| 7,883,843 B2 * | 2/2011 | Milich ............... A61K 39/385 |
| | | 435/5 |
| 2010/0234283 A1 * | 9/2010 | Kaumaya ............ C07K 14/52 |
| | | 514/8.1 |
| 2011/0318373 A1 | 12/2011 | Sasikumar et al. |
| 2014/0010831 A1 | 1/2014 | Kaumaya |
| 2014/0302070 A1 * | 10/2014 | Chen ................ C07K 16/2818 |
| | | 435/375 |
| 2015/0017194 A1 * | 1/2015 | Akahata .............. A61K 39/12 |
| | | 435/320.1 |

FOREIGN PATENT DOCUMENTS

| RU | 2599417 C2 | 10/2016 | |
| WO | 94/29348 | 12/1994 | |
| WO | WO-9738011 A1 * | 10/1997 | .......... A61K 39/385 |
| WO | WO-2005066867 A2 * | 7/2005 | ....... C07K 14/70521 |
| WO | 2006121168 A1 | 11/2006 | |
| WO | 2015/005500 | 1/2015 | |
| WO | 2016/021209 | 2/2016 | |
| WO | WO-2016022994 A2 * | 2/2016 | ............ A61K 35/17 |
| WO | 2016/106159 | 6/2016 | |

OTHER PUBLICATIONS

Nair et al. (J. Immunol. Feb. 1, 2003; 170 (3): 1362-73).*
Tindle et al. (Proc. Natl. Acad. Sci. USA. Jul. 1, 1991; 88 (13): 5887-91).*
Nezafat et al. (J. Theor. Biol. May 21, 2014; 349: 121-34).*
Pourseif et al. (Bioimpacts. 2018; 8 (1): 39-52).*
Athanasiou et al. (Front. Immun. Jun. 13, 2017; 8: 684; pp. 1-25).*
Finger et al. (Gene. Sep. 15, 1997; 197 (1-2): 177-87).*
Li et al. (J. Biol. Chem. Jun. 18, 2010; 285 (25): 19572-81).*
Bergmann et al. (J. Immunol. Oct. 15, 1996; 157 (8): 3242-9).*
Nielsen et al. (Cell Immunol. Jun. 2005; 235 (2): 109-16).*
Fessas et al. (Semin. Oncol. Apr. 2017; 44 (2): 136-140).*
Li et al. (MAbs. May-Jun. 2017; 9 (4): 628-37).*
Guo et al. (J. Cancer. Feb. 10, 2017; 8 (3): 410-416).*
International Preliminary Report on Patentability issued for Application No. PCT/US2018/024831, dated Oct. 10, 2019.
European Search Report issued for U.S. Appl. No. 18/778,305, dated Nov. 27, 2020.
Allen, S. D., et al. "Therapeutic peptidomimetic strategies for autoimmune diseases costimulation blockade." The Journal of peptide research 65.6 (2005): 591-604.
Allen, Stephanie D., et al. "Peptide vaccines of the HER-2/neu dimerization loop are effective in inhibiting mammary tumor growth in vivo." The Journal of Immunology 179.1 (2007): 472-482.

(Continued)

*Primary Examiner* — Stephen L Rawlings
(74) *Attorney, Agent, or Firm* — Meunier Carlin & Curfman LLC

(57) ABSTRACT

Disclosed are compositions related to synthetic PD-1 peptides, chimeric PD-1 peptides, anti-PD-1 antibodies and methods of treating cancers, autoimmune diseases, and Alzheimer's disease using said peptides or antibodies.

15 Claims, 42 Drawing Sheets

Figure 2A:
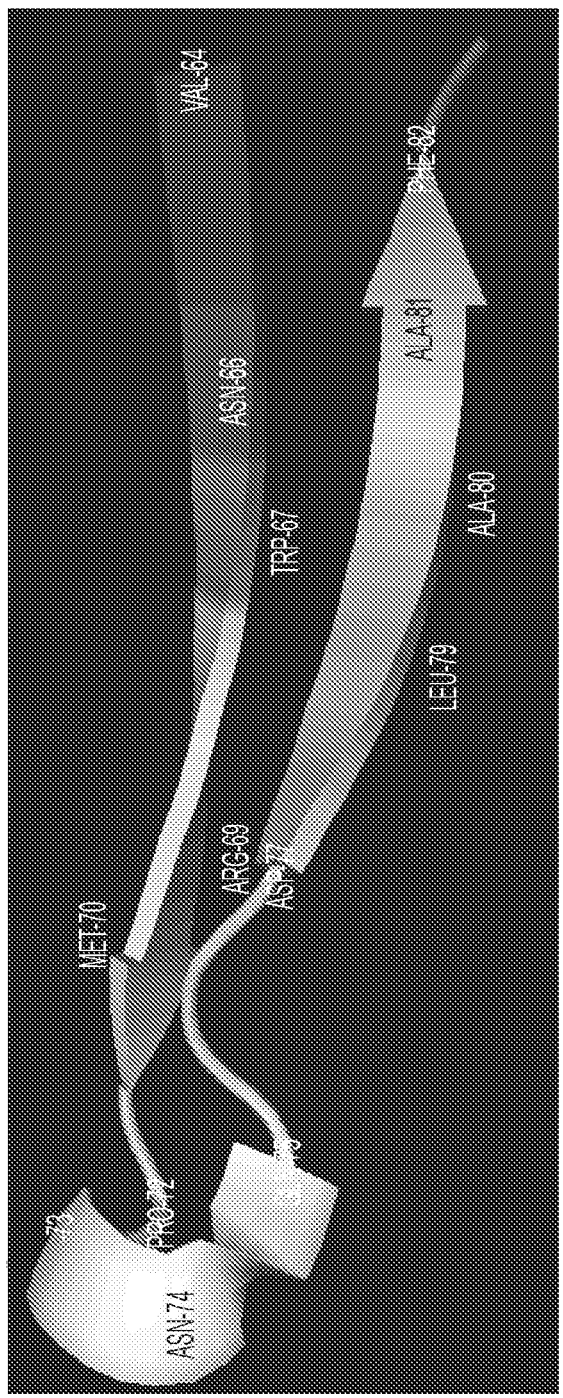

Specification includes a Sequence Listing.

(56) References Cited

OTHER PUBLICATIONS

Almquist, Ronald G., et al. "Synthesis and biological activity of a ketomethylene analog of a tripeptide inhibitor of angiotensin converting enzyme." Journal of medicinal chemistry 23.12 (1980): 1392-1398.

Arteaga, Carlos L., and Jeffrey A. Engelman. "ERBB receptors: from oncogene discovery to basic science to mechanism-based cancer therapeutics." Cancer cell 25.3 (2014): 282-303.

Bagshawe, K. D., et al. "A cytotoxic agent can be generated selectively at cancer sites." British journal of cancer 58.6 (1988): 700-703.

Bagshawe, K. D. "Towards generating cytotoxic agents at cancer sites. The First Bagshawe Lecture." Br. J. Cancer 60 (1989): 275-281.

Baras, Alexander S., et al. "The ratio of CD8 to Treg tumor-infiltrating lymphocytes is associated with response to cisplatin-based neoadjuvant chemotherapy in patients with muscle invasive urothelial carcinoma of the bladder." Oncoimmunology 5.5 (2016): e1134412.

Baselga, José, and Carlos L. Arteaga. "Critical update and emerging trends in epidermal growth factor receptor targeting in cancer." Journal of Clinical Oncology 23.11 (2005): 2445-2459.

Baselga, Jose, and Sandra M. Swain. "Novel anticancer targets: revisiting ERBB2 and discovering ERBB3." Nature Reviews Cancer 9.7 (2009): 463-475.

Baselga, Jose. "Targeting tyrosine kinases in cancer: the second wave." Science 312.5777 (2006): 1175-1178.

Battelli, M. G., et al. "T lymphocyte killing by a xanthine-oxidase-containing immunotoxin." Cancer Immunology, Immunotherapy 35.6 (1992): 421-425.

Brahmer, J. R., et al. "Camacho 625 LH, Kauh J, Odunsi K, Pitot HC, Hamid O, Bhatia S, Martins R, Eaton K, Chen S, Salay 626 TM, Alaparthy S, Grosso JF, Korman AJ, Parker SM, Agrawal S, Goldberg SM, Pardoll 627 DM, Gupta A, Wigginton JM. 2012. Safety and activity of anti-PD-L1 antibody in patients with 628 advanced cancer." N Engl J Med 366: 2455-2465.

Brown, Valerie I., and Mark I. Greene. "Molecular and cellular mechanisms of receptor-mediated endocytosis." DNA and cell biology 10.6 (1991): 399-409.

Brüggemann, Marianne, N. P. Davies, and I. R. Rosewell. "Designer mice: the production of human antibody repertoires in transgenic animals." The Year in immunology 7 (1993): 33-40.

Chames P, Van Regenmortel M, Weiss E, Baty D. Therapeutic antibodies: successes, limitations and hopes for the future. Br J Pharmacol. 2009;157(2):220-33. doi: 10.1111/j.1476-5381.2009.00190.x. PubMed PMID: 19459844; PubMed Central PMCID: PMCPMC2697811.

Chou PY, Fasman GD. Prediction of the secondary structure of proteins from their amino acid sequence. Advances in enzymology and related areas of molecular biology. 1978;47:45-148. PubMed PMID: 364941.

Cobleigh MA, Langmuir VK, Sledge GW, Miller KD, Haney L, Novotny WF, Reimann JD, Vassel A. A phase I/II dose-escalation trial of bevacizumab in previously treated metastatic breast cancer. Seminars in oncology. 2003;30(5 Suppl 16): 117-24. PubMed PMID: 14613032.

Dakappagari NK, Douglas DB, Triozzi PL, Stevens VC, Kaumaya PT. Prevention of mammary tumors with a chimeric HER-2 B-cell epitope peptide vaccine. Cancer Res. 2000;60(14):3782-9. PubMed PMID: 10919651.

Dakappagari NK, Lute KD, Rawale S, Steele JT, Allen SD, Phillips G, Reilly RT, Kaumaya PT. Conformational HER-2/neu B-cell epitope peptide vaccine designed to incorporate two native disulfide bonds enhances tumor cell binding and antitumor activities. J Biol Chem. 2005;280(1):54-63. doi: 10.1074/jbc.M411020200. PubMed PMID: 15507452.

Dakappagari NK, Pyles J, Parihar R, Carson WE, Young DC, Kaumaya PT. A chimeric multi-human epidermal growth factor receptor-2 B cell epitope peptide vaccine mediates superior antitumor responses. J Immunol. 2003;170(8):4242-53. Epub Apr. 12, 2003. PubMed PMID: 12682258.

Dakappagari NK, Sundaram R, Rawale S, Liner A, Galloway DR, Kaumaya PT. Intracellular delivery of a novel multiepitope peptide vaccine by an amphipathic peptide carrier enhances cytotoxic T-cell responses in HLA-A*201 mice. J Pept Res. 2005;65(2): 189-99. Epub Feb. 12, 2005. doi: JPP212 [pii] 10.1111/j.1399-3011.2005.00212.x. PubMed PMID: 15705163.

DeLeeuw, R.J., et al., The prognostic value of FoxP3+ tumor-infiltrating lymphocytes in cancer: a critical review of the literature. Clin Cancer Res, 2012. 18(11): p. 3022-9.

Eskens FA, Verweij J. The clinical toxicity profile of vascular endothelial growth factor (VEGF) and vascular endothelial growth factor receptor (VEGFR) targeting angiogenesis inhibitors; a review. European journal of cancer. 2006;42(18):3127-39. Epub Nov. 14, 2006. doi: S0959-8049(06)00848-3 [pii] 10.1016/j.ejca.2006.09.015. PubMed PMID: 17098419.

Ferrone et al., eds., Noges Publications, Park Ridge, N.J., (1985) ch. 22 and pp. 303-357.

Folkman J. Tumor angiogenesis: therapeutic implications. The New England journal of medicine. 1971;285(21):1182-6. PubMed PMID: 4938153.

Foy KC, Liu Z, Phillips G, Miller M, Kaumaya PT. Combination treatment with HER-2 and VEGF peptide mimics induces potent anti-tumor and anti-angiogenic responses in vitro and in vivo. J Biol Chem. 2011;286(15):13626-37. Epub Feb. 18, 2011. doi: 10.1074/jbc.M110.216820. PubMed PMID: 21325276; PubMed Central PMCID: PMC3075707.

Foy KC, Miller MJ, Moldovan N, Carson WE, Kaumaya PTP. Combined vaccination with HER-2 peptide followed by therapy with VEGF peptide mimics exerts effective anti-tumor and anti-angiogenic effects in vitro and in vivo. Oncoimmunology. 2012;1(7).

Foy KC, Vicari D, Kaumaya PTP. Therapeutic Peptides Targeting HER-2/neu and VEGF Signaling Pathways in Breast Cancer. Handbook of Biologically Active Peptides2013. p. 612-6.

Garrett, J.T., et al., Novel engineered trastuzumab conformational epitopes demonstrate in vitro and in vivo antitumor properties against HER-2/neu. J Immunol, 2007. 178(11): p. 7120-31.

Grothey A. Recognizing and managing toxicities of molecular targeted therapies for colorectal cancer. Oncology (Williston Park). 2006;20(14 Suppl 10):21-8. Epub Mar. 16, 2007. PubMed PMID: 17354514.

Smith, T.W., Butler, V.P., Jr., Haber, E.: Cardiac glyco side-specific antibodies in the treatment of digitalis intoxication. In: Antibodies in Human Diagnosis and Therapy. Haber, E., Krause, R.M. (eds.) New York: Raven Press pp. 365-389 (1977).

Hadrup, S., M. Donia, and P. Thor Straten, Effector CD4 and CD8 T cells and their role in the tumor microenvironment. Cancer Microenviron, 2013. 6(2): p. 123-33.

Hamid, Omid, et al. "Safety and tumor responses with lambrolizumab (anti-PD-1) in melanoma." New England Journal of Medicine 369.2 (2013): 134-144.

Hann, Michael M., et al. "On the double bond isostere of the peptide bond: preparation of an enkephalin analogue." Journal of the Chemical Society, Perkin Transactions 1 (1982): 307-314.

Harding FA, Stickler MM, Razo J, DuBridge RB. The immunogenicity of humanized and fully human antibodies: residual immunogenicity resides in the CDR Yegions. mAbs. 2010;2(3):256-65. PubMed PMID: 20400861; PubMed Central PMCID: PMCPMC2881252.

Hoeben A, Landuyt B, Highley MS, Wildiers H, Van Oosterom AT, De Bruijn EA. Vascular endothelial growth Factor and Angiogenesis. Pharmacological Reviews Dec. 2004, 56 (4) 549-580.

Holladay, Mark W., and Daniel H. Rich. "Synthesis of hydroxy ethylene and ketomethylene dipeptide isosteres." Tetrahedron Letters 24.41 (1983): 4401-4404.

Hopp TP, Woods KR. Prediction of protein antigenic determinants from amino acid sequences. Proceedings of the National Academy of Sciences of the United States of America. 1981;78(6):3824-8. PubMed PMID: 6167991; PubMed Central PMCID: PMC319665.

Houck KA, Ferrara N, Winer J, Cachianes G, Li B, Leung DW. The vascular endothelial growth factor family: identification of a fourth

(56) References Cited

OTHER PUBLICATIONS molecular species and characterization of alternative splicing of RNA. Molecular endocrinology. 1991;5(12):1806-14. Epub Dec. 1, 1991. PubMed PMID: 1791831.

Hruby, Victor J. "Conformational restrictions of biologically active peptides via amino acid side chain groups." Life sciences 31.3 (1982): 189-199.

Hudson, Derek, et al. "Methionine enkephalin and isosteric analogues I. Synthesis on a phenolic resin support." International journal of peptide and protein research 14.3 (1979): 177-185.

Hughes, Brenda J., et al. "Monoclonal antibody targeting of liposomes to mouse lung in vivo." Cancer research 49.22 (1989): 6214-6220.

Hynes, Nancy E., and Heidi A. Lane. "ERBB receptors and cancer: the complexity of targeted inhibitors." Nature Reviews Cancer 5.5 (2005): 341-354.

Ishida, Yasumasa, et al. "Induced expression of PD-1, a novel member of the immunoglobulin gene superfamily, upon programmed cell death." The EMBO journal 11.11 (1992): 3887-3895.

Iwai, Yoshiko, et al. "Involvement of PD-L1 on tumor cells in the escape from host immune system and tumor immunotherapy by PD-L1 blockade." Proceedings of the National Academy of Sciences 99.19 (2002): 12293-12297.

Jaeger, John A., Douglas H. Turner, and Michael Zuker. "[17] Predicting optimal and suboptimal secondary structure for RNA." (1990): 281-306.

Jaeger, John A., Douglas H. Turner, and Michael Zuker. "Improved predictions of secondary structures for RNA." Proceedings of the National Academy of Sciences 86.20 (1989): 7706-7710.

Jain, Rakesh K., et al. "Lessons from phase III clinical trials on anti-VEGF therapy for cancer." Nature clinical practice Oncology 3.1 (2006): 24-40.

Jakobovits, Aya, et al. "Germ-line transmission and expression of a human-derived yeast artificial chromosome." Nature 362.6417 (1993): 255-258.

Jakobovits, Aya, et al. "Analysis of homozygous mutant chimeric mice: deletion of the immunoglobulin heavy-chain joining region blocks B-cell development and antibody production." Proceedings of the National Academy of Sciences 90.6 (1993): 2551-2555.

Jennings-White et al., "Synthesis of Ketomethylene Analogs of Dipeptides," Tetrahedron Letters, 1982; 23:2533-2534.

Karplus, P. Andrew, and Georg E. Schulz. "Refined structure of glutathione reductase at 1.54 Å resolution." Journal of molecular biology 195.3 (1987): 701-729.

Kaumaya, Pravin TP, et al. "Phase I active immunotherapy with combination of two chimeric, human epidermal growth factor receptor 2, B-cell epitopes fused to a promiscuous T-cell epitope in patients with metastatic and/or recurrent solid tumors." Journal of Clinical Oncology 27.31 (2009): 5270.

Kaumaya, Pravin TP. "A paradigm shift: cancer therapy with peptide-based B-cell epitopes and peptide immunotherapeutics targeting multiple solid tumor types: emerging concepts and validation of combination immunotherapy." Human vaccines & immunotherapeutics 11.6 (2015): 1368-1386.

Kaumaya, Pravin TP. "Could precision-engineered peptide epitopes/vaccines be the key to a cancer cure?." Future Oncology 7.7 (2011): 807-810.

Kaumaya, Pravin TP, et al. ""De novo" engineering of peptide immunogenic and antigenic determinants as potential vaccines." Peptides (1994): 133-164.

Kaumaya, Pravin TP. "HER-2/neu cancer vaccines: Present status and future prospects." International journal of peptide research and therapeutics 12.1 (2006): 65-77.

Köhler, Georges, and Cesar Milstein. "Continuous cultures of fused cells secreting antibody of predefined specificity." nature 256.5517 (1975): 495-497.

Kyte, Jack, and Russell F. Doolittle. "A simple method for displaying the hydropathic character of a protein." Journal of molecular biology 157.1 (1982): 105-132.

Li, Bing, et al. "KDR (VEGF receptor 2) is the major mediator for the hypotensive effect of VEGF." Hypertension 39.6 (2002): 1095-1100.

Litzinger and Huang, Biochimica et Biophysica Acta, 1104:179-187, (1992).

Lynch, Marcus P., and Pravin TP Kaumaya. "Advances in HTLV-1 peptide vaccines and therapeutics." Current Protein and Peptide Science 7.2 (2006): 137-145.

Miller, Megan Jo, Kevin Chu Foy, and Pravin TP Kaumaya. "Cancer immunotherapy: present status, future perspective, and a new paradigm of peptide immunotherapeutics." Discovery medicine 15.82 (2013): 166-176.

Morley, J. S. "Modulation of the action of regulatory peptides by structural modification." Trends in Pharmacological Sciences 1.2 (1980): 463-468.

Motzer, Robert J., et al. "Nivolumab for metastatic renal cell carcinoma: results of a randomized phase II trial." Journal of clinical oncology 33.13 (2015): 1430-7.

Needleman, Saul B., and Christian D. Wunsch. "A general method applicable to the search for similarities in the amino acid sequence of two proteins." Journal of molecular biology 48.3 (1970): 443-453.

Nelson AL, Dhimolea E, Reichert JM. Development trends for human monoclonal antibody therapeutics. Nature reviews Drug discovery. 2010;9(10):767-74. doi: 10.1038/nrd3229. PubMed PMID: 20811384.

Novotný, Jiří, et al. "Antigenic determinants in proteins coincide with surface regions accessible to large probes (antibody domains)." Proceedings of the National Academy of Sciences 83.2 (1986): 226-230.

Oshima, Robert G., et al. "Angiogenic acceleration of Neu induced mammary tumor progression and metastasis." Cancer research 64.1 (2004): 169-179.

Pearson, William R., and David J. Lipman. "Improved tools for biological sequence comparison." Proceedings of the National Academy of Sciences 85.8 (1988): 2444-2448.

Pietersz, Geoffrey A., and Ian FC McKenzie. "Antibody conjugates for the treatment of cancer." Immunological reviews 129.1 (1992): 57-80.

Preston, Claudia C., et al. "The ratios of CD8+ T cells to CD4+ CD25+ FOXP3+ and FOXP3-T cells correlate with poor clinical outcome in human serous ovarian cancer." PloS one 8.11 (2013): e80063.

Rizvi, Naiyer A., et al. "Activity and safety of nivolumab, an anti-PD-1 immune checkpoint inhibitor, for patients with advanced, refractory squamous non-small-cell lung cancer (CheckMate 063): a phase 2, single-arm trial." The lancet oncology 16.3 (2015): 257-265.

Roffler, Steven R., et al. "Anti-neoplastic glucuronide prodrug treatment of human tumor cells targeted with a monoclonal antibody-enzyme conjugate." Biochemical pharmacology 42.10 (1991): 2062-2065.

Rose, George D., et al. "Hydrophobicity of amino acid residues in globular proteins." Science 229.4716 (1985): 834-838.

Roskoski Jr, Robert. "The ErbB/HER family of protein-tyrosine kinases and cancer." Pharmacological research 79 (2014): 34-74.

Senter, Peter D., et al. "Generation of 5-fluorouracil from 5-fluorocytosine by monoclonal antibody-cytosine deaminase conjugates." Bioconjugate chemistry 2.6 (1991): 447-451.

Senter, Peter D., et al. "Generation of cytotoxic agents by targeted enzymes." Bioconjugate chemistry 4.1 (1993): 3-9.

Sharma P, Allison JP. The future of immune checkpoint therapy. Science. 2015;348(6230):56-61. doi: 10.1126/science.aaa8172. PubMed PMID: 25838373.

Shinohara, Takashi, et al. "Structure and chromosomal localization of the human PD-1 gene (PDCD1)." Genomics 23.3 (1994): 704-706.

Smith, Temple F., and Michael S. Waterman. "Comparison of biosequences." Advances in applied mathematics 2.4 (1981): 482-489.

Spatola, Arno F., et al. "Structure-activity relationships of enkephalins containing serially replaced thiomethylene amide bond surrogates." Life sciences 38.14 (1986): 1243-1249.

(56) References Cited

OTHER PUBLICATIONS

Srinivasan, Mythily, et al. "Suppression of experimental autoimmune encephalomyelitis using peptide mimics of CD28." The Journal of Immunology 169.4 (2002): 2180-2188.
Srinivasan, Mythily, et al. "A retro-inverso peptide mimic of CD28 encompassing the MYPPPY motif adopts a polyproline type II helix and inhibits encephalitogenic T cells in vitro." The Journal of Immunology 167.1 (2001): 578-585.
Steele, Joan T., Stephanie D. Allen, and Pravin TP Kaumaya. "Cancer Immunotherapy with Rationally Designed Synthetic Peptides." Handbook of Biologically Active Peptides. Academic Press, 2006. 491-498.
Sundaram, Roshni, Naveen K. Dakappagari, and Pravin TP Kaumaya. "Synthetic peptides as cancer vaccines." Peptide Science: Original Research on Biomolecules 66.3 (2002): 200-216.
Thornton, J. M., et al. "Location of 'continuous' antigenic determinants in the protruding regions of proteins." The EMBO journal 5.2 (1986): 409-413.
Topalian, Suzanne L., Charles G. Drake, and Drew M. Pardoll. "Immune checkpoint blockade: a common denominator approach to cancer therapy." Cancer cell 27.4 (2015): 450-461.
Topalian, Suzanne L., et al. "Safety, activity, and immune correlates of anti-PD-1 antibody in cancer." New England Journal of Medicine 366.26 (2012): 2443-2454.
Vicari, Daniele, et al. "Engineered conformation-dependent VEGF peptide mimics are effective in inhibiting VEGF signaling pathways." Journal of Biological Chemistry 286.15 (2011): 13612-13625.
Wang, Bing, Pravin TP Kaumaya, and David E. Cohn. "Immunization with synthetic VEGF peptides in ovarian cancer." Gynecologic oncology 119.3 (2010): 564-570.
Welling, Gjalt W., et al. "Prediction of sequential antigenic regions in proteins." FEBS letters 188.2 (1985): 215-218.
Yarden, et al., "Untangling the ErbB signaling network. 2001." Nat Rev Mol Cell Biol 2 (2001): 127-137.
Zak, Krzysztof M., et al. "Structure of the complex of human programmed death 1, PD-1, and its ligand PD-L1" Structure 23.12 (2015): 2341-2348.
Zhu, Zhenping, and Larry Witte. "Inhibition of tumor growth and metastasis by targeting tumor-associated angiogenesis with antagonists to the receptors of vascular endothelial growth factor." Investigational new drugs 17.3 (1999): 195-212.
Zoller, Mark J. "New recombinant DNA methodology for protein engineering." Current opinion in biotechnology 3.4 (1992): 348-354.
Zuker, Michael. "On finding all suboptimal foldings of an RNA molecule." Science 244.4900 (1989): 48-52.
International Search Report and Written Opinion issued by the International Searching Authority (ISA/US) in PCT Application No. PCT/US2018/024831 dated Aug. 1, 2018. 13 pages.
Russian Patent Office. Office Action issued in Russian Application No. 2019131252 dated Jun. 1, 2021. 18 pages, including English translation.
European Patent Office. Communication pursuant to Article 94(3) EPC issued in European Application No. 18778305.5 dated Jun. 14, 2021. 6 pages.
Kontermann, Roland E., and Ulrich Brinkmann. "Bispecific antibodies." Drug discovery today 20.7 (2015): 838-847.
Shen, Juqun, et al. "Single variable domain-IgG fusion: a novel recombinant approach to Fc domain-containing bispecific antibodies." Journal of Biological Chemistry 281.16 (2006): 10706-10714.
Burks, A. Wesley, Nina King, and Gary A. Bannon. "Modification of a major peanut allergen leads to loss of IgE binding." International archives of allergy and immunology 118.2-4 (1999): 313.
Luo, Zhongli, Shunkang Wang, and Shuguang Zhang. "Fabrication of self-assembling D-form peptide nanofiber scaffold d-EAK16 for rapid hemostasis." Biomaterials 32.8 (2011): 2013-2020.
Chen, Xiaoying, Jennica L. Zara, and Wei-Chiang Shen "Fusion protein linkers: property, design and functionality." Advanced drug delivery reviews 65.10 (2013): 1357-1369.
Maeda, Yumi, et al. "Engineering of functional chimeric protein G-VargulaLuciferase." Analytical biochemistry 249.2 (1997): 147-152.
Muller, Sylviane, et al. "Spliceosomal peptide P140 for immunotherapy of systemic lupus erythematosus: results of an early phase II clinical trial." Arthritis & Rheumatism: Official Journal of the American College of Rheumatology 58.12 (2008): 3873-3883.
Russian Patent Office Office Action issued in Russian Application No. 2019131252 dated Oct. 29, 2021. 30 pages, including English translation.
Office Action issued for Japanese Application No. 2019-553504, dated Jan. 19, 2022.

* cited by examiner

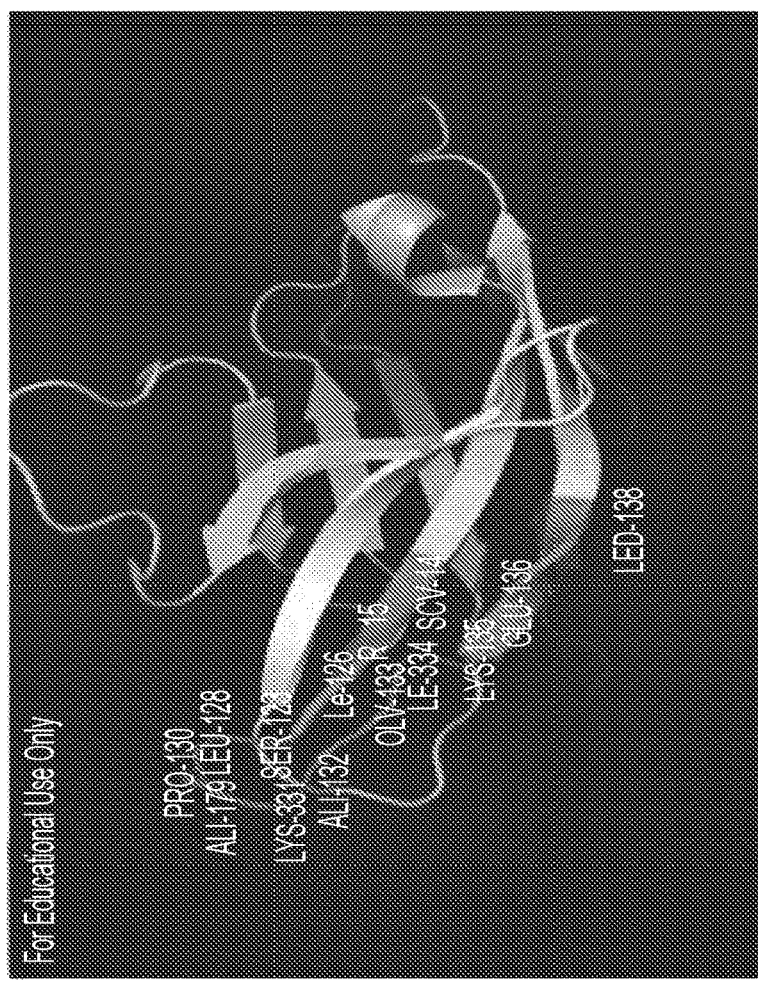
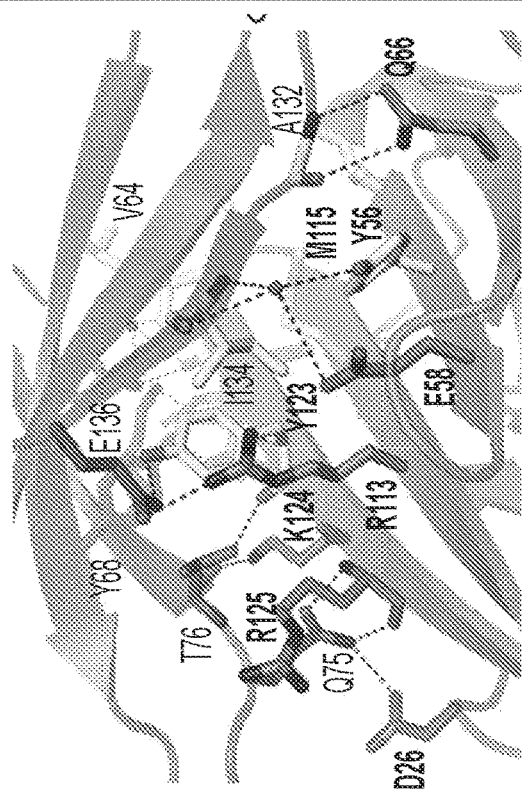
F I G. 1

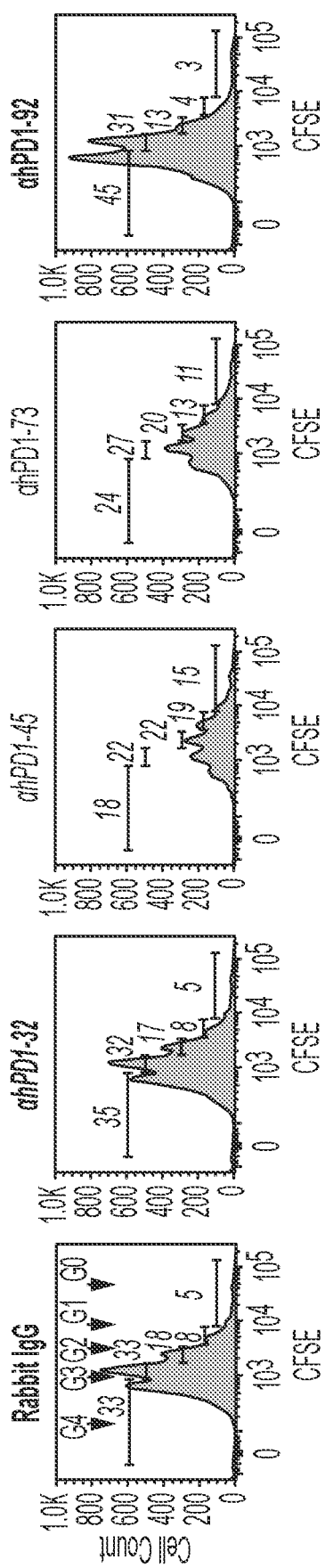
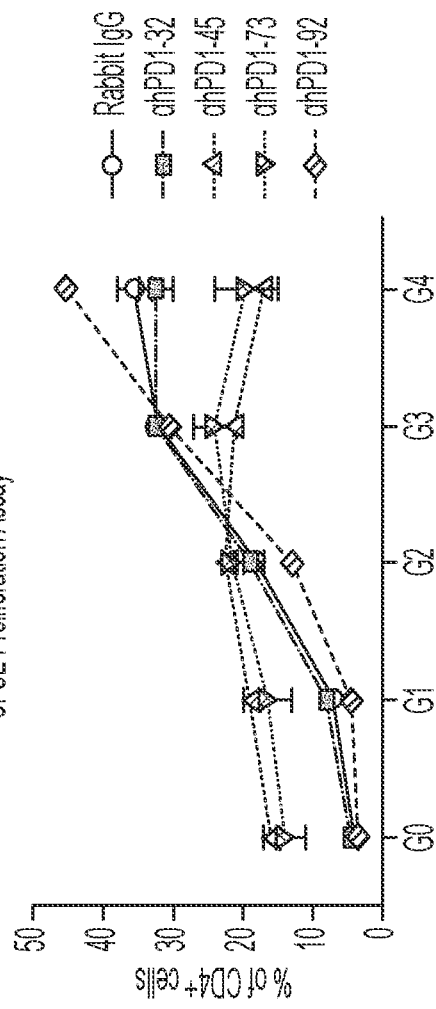
FIG. 13A
FIG. 13B

SEQUENCE LISTING

<160> NUMBER OF SEQ ID NOS: 30

<210> SEQ ID NO 1
<211> LENGTH: 126
<212> TYPE: PRT
<213> ORGANISM: Artificial Sequence
<220> FEATURE:
<223> OTHER INFORMATION: synthetic construct

<400> SEQUENCE: 1

Pro Pro Thr Phe Ser Pro Ala Leu Leu Val Val Thr Glu Gly Asp Asn
1               5                   10                  15

Ala Thr Phe Thr Cys Ser Phe Ser Asn Thr Ser Glu Ser Phe Val Leu
            20                  25                  30

Asn Trp Tyr Arg Met Ser Pro Ser Asn Gln Thr Asp Lys Leu Ala Ala
        35                  40                  45

Phe Pro Glu Asp Arg Ser Gln Pro Gly Gln Asp Cys Arg Phe Arg Val
    50                  55                  60

Thr Gln Leu Pro Asn Gly Arg Asp Phe His Met Ser Val Val Arg Ala
65                  70                  75                  80

Arg Arg Asn Asp Ser Gly Thr Tyr Leu Cys Gly Ala Ile Ser Leu Ala
                85                  90                  95

Pro Lys Leu Gln Ile Lys Glu Ser Leu Arg Ala Glu Arg Val Thr Glu
            100                 105                 110

Arg Arg Ala Glu Val Pro Thr Ala His Pro Ser Pro Ser Pro
        115                 120                 125

<210> SEQ ID NO 2
<211> LENGTH: 19
<212> TYPE: PRT
<213> ORGANISM: Artificial Sequence
<220> FEATURE:
<223> OTHER INFORMATION: synthetic construct

<400> SEQUENCE: 2

Val Leu Asn Trp Tyr Arg Met Ser Pro Ser Asn Gln Thr Asp Lys Leu
1               5                   10                  15

Ala Ala Phe

<210> SEQ ID NO 3
<211> LENGTH: 19
<212> TYPE: PRT
<213> ORGANISM: Artificial Sequence
<220> FEATURE:
<223> OTHER INFORMATION: synthetic construct

<400> SEQUENCE: 3

Lys Leu Ala Ala Phe Pro Glu Asp Arg Ser Gln Pro Gly Gln Asp Cys
1               5                   10                  15

Arg Phe Arg

<210> SEQ ID NO 4
<211> LENGTH: 18
<212> TYPE: PRT
<213> ORGANISM: Artificial Sequence
<220> FEATURE:
<223> OTHER INFORMATION: synthetic construct

<400> SEQUENCE: 4

Asp Phe His Met Ser Val Val Arg Ala Arg Arg Asn Asp Ser Gly Thr
1               5                   10                  15

Tyr Leu

<210> SEQ ID NO 5
<211> LENGTH: 19
<212> TYPE: PRT
<213> ORGANISM: Artificial Sequence
<220> FEATURE:
<223> OTHER INFORMATION: synthetic construct

<400> SEQUENCE: 5

Gly Ala Ile Ser Leu Ala Pro Lys Ala Gln Ile Lys Glu Ser Leu Arg
1               5                   10                  15

Ala Glu Leu

<210> SEQ ID NO 6
<211> LENGTH: 18
<212> TYPE: PRT
<213> ORGANISM: Artificial Sequence
<220> FEATURE:
<223> OTHER INFORMATION: synthetic construct

<400> SEQUENCE: 6

Lys Leu Leu Ser Leu Ile Lys Gly Val Ile Val His Arg Leu Glu Gly
1               5                   10                  15

Val Glu

<210> SEQ ID NO 7
<211> LENGTH: 4
<212> TYPE: PRT
<213> ORGANISM: Artificial Sequence
<220> FEATURE:
<223> OTHER INFORMATION: synthetic construct

<400> SEQUENCE: 7

Gly Pro Ser Leu
1

<210> SEQ ID NO 8
<211> LENGTH: 41
<212> TYPE: PRT
<213> ORGANISM: Artificial Sequence
<220> FEATURE:
<223> OTHER INFORMATION: synthetic construct

<400> SEQUENCE: 8

Lys Leu Leu Ser Leu Ile Lys Gly Val Ile Val His Arg Leu Glu Gly
1               5                   10                  15

Val Glu Gly Pro Ser Leu Val Leu Asn Trp Tyr Arg Met Ser Pro Ser
            20                  25                  30

Asn Gln Thr Asp Lys Leu Ala Ala Phe
        35                  40

<210> SEQ ID NO 9
<211> LENGTH: 41
<212> TYPE: PRT
<213> ORGANISM: Artificial Sequence
<220> FEATURE:
<223> OTHER INFORMATION: synthetic construct

<400> SEQUENCE: 9

Lys Leu Leu Ser Leu Ile Lys Gly Val Ile Val His Arg Leu Glu Gly
1               5                   10                  15

Val Glu Gly Pro Ser Leu Lys Leu Ala Ala Phe Pro Glu Asp Arg Ser
            20                  25                  30

```
Gln Pro Gly Gln Asp Cys Arg Phe Arg
        35                  40

<210> SEQ ID NO 10
<211> LENGTH: 40
<212> TYPE: PRT
<213> ORGANISM: Artificial Sequence
<220> FEATURE:
<223> OTHER INFORMATION: synthetic construct

<400> SEQUENCE: 10

Lys Leu Leu Ser Leu Ile Lys Gly Val Ile Val His Arg Leu Glu Gly
1               5                   10                  15

Val Glu Gly Pro Ser Leu Asp Phe His Met Ser Val Val Arg Ala Arg
            20                  25                  30

Arg Asn Asp Ser Gly Thr Tyr Leu
        35                  40

<210> SEQ ID NO 11
<211> LENGTH: 41
<212> TYPE: PRT
<213> ORGANISM: Artificial Sequence
<220> FEATURE:
<223> OTHER INFORMATION: synthetic construct

<400> SEQUENCE: 11

Lys Leu Leu Ser Leu Ile Lys Gly Val Ile Val His Arg Leu Glu Gly
1               5                   10                  15

Val Glu Gly Pro Ser Leu Gly Ala Ile Ser Leu Ala Pro Lys Ala Gln
            20                  25                  30

Ile Lys Glu Ser Leu Arg Ala Glu Leu
        35                  40

<210> SEQ ID NO 12
<211> LENGTH: 19
<212> TYPE: PRT
<213> ORGANISM: Artificial Sequence
<220> FEATURE:
<223> OTHER INFORMATION: synthetic construct

<400> SEQUENCE: 12

Phe Ala Ala Leu Lys Asp Thr Gln Asn Ser Pro Ser Met Arg Tyr Trp
1               5                   10                  15

Asn Leu Val

<210> SEQ ID NO 13
<211> LENGTH: 19
<212> TYPE: PRT
<213> ORGANISM: Artificial Sequence
<220> FEATURE:
<223> OTHER INFORMATION: synthetic construct

<400> SEQUENCE: 13

Arg Phe Arg Cys Asp Gln Gly Pro Gln Ser Arg Asp Glu Pro Phe Ala
1               5                   10                  15

Ala Leu Lys

<210> SEQ ID NO 14
<211> LENGTH: 18
<212> TYPE: PRT
<213> ORGANISM: Artificial Sequence
<220> FEATURE:
<223> OTHER INFORMATION: synthetic construct
```

```
<400> SEQUENCE: 14

Leu Tyr Thr Gly Ser Asp Asn Arg Arg Ala Arg Val Val Ser Met His
1               5                   10                  15

Phe Asp

<210> SEQ ID NO 15
<211> LENGTH: 19
<212> TYPE: PRT
<213> ORGANISM: Artificial Sequence
<220> FEATURE:
<223> OTHER INFORMATION: synthetic construct

<400> SEQUENCE: 15

Leu Glu Ala Arg Leu Ser Glu Lys Ile Gln Ala Lys Pro Ala Leu Ser
1               5                   10                  15

Ile Ala Gly

<210> SEQ ID NO 16
<211> LENGTH: 41
<212> TYPE: PRT
<213> ORGANISM: Artificial Sequence
<220> FEATURE:
<223> OTHER INFORMATION: synthetic construct

<400> SEQUENCE: 16

Lys Leu Leu Ser Leu Ile Lys Gly Val Ile Val His Arg Leu Glu Gly
1               5                   10                  15

Val Glu Gly Pro Ser Leu Phe Ala Ala Leu Lys Asp Thr Gln Asn Ser
            20                  25                  30

Pro Ser Met Arg Tyr Trp Asn Leu Val
        35                  40

<210> SEQ ID NO 17
<211> LENGTH: 41
<212> TYPE: PRT
<213> ORGANISM: Artificial Sequence
<220> FEATURE:
<223> OTHER INFORMATION: synthetic construct

<400> SEQUENCE: 17

Lys Leu Leu Ser Leu Ile Lys Gly Val Ile Val His Arg Leu Glu Gly
1               5                   10                  15

Val Glu Gly Pro Ser Leu Arg Phe Arg Cys Asp Gln Gly Pro Gln Ser
            20                  25                  30

Arg Asp Glu Pro Phe Ala Ala Leu Lys
        35                  40

<210> SEQ ID NO 18
<211> LENGTH: 40
<212> TYPE: PRT
<213> ORGANISM: Artificial Sequence
<220> FEATURE:
<223> OTHER INFORMATION: synthetic construct

<400> SEQUENCE: 18

Lys Leu Leu Ser Leu Ile Lys Gly Val Ile Val His Arg Leu Glu Gly
1               5                   10                  15

Val Glu Gly Pro Ser Leu Leu Tyr Thr Gly Ser Asp Asn Arg Arg Ala
            20                  25                  30

Arg Val Val Ser Met His Phe Asp
        35                  40
```

<210> SEQ ID NO 19
<211> LENGTH: 41
<212> TYPE: PRT
<213> ORGANISM: Artificial Sequence
<220> FEATURE:
<223> OTHER INFORMATION: synthetic construct

<400> SEQUENCE: 19

Lys Leu Leu Ser Leu Ile Lys Gly Val Ile Val His Arg Leu Glu Gly
1               5                   10                  15

Val Glu Gly Pro Ser Leu Leu Glu Ala Arg Leu Ser Glu Lys Ile Gln
            20                  25                  30

Ala Lys Pro Ala Leu Ser Ile Ala Gly
        35                  40

<210> SEQ ID NO 20
<211> LENGTH: 19
<212> TYPE: PRT
<213> ORGANISM: Artificial Sequence
<220> FEATURE:
<223> OTHER INFORMATION: synthetic construct

<400> SEQUENCE: 20

Asn Ser Val Asp Asp Ala Leu Ile Asn Ser Thr Ile Tyr Ser Tyr Phe
1               5                   10                  15

Pro Ser Val

<210> SEQ ID NO 21
<211> LENGTH: 17
<212> TYPE: PRT
<213> ORGANISM: Artificial Sequence
<220> FEATURE:
<223> OTHER INFORMATION: synthetic construct

<400> SEQUENCE: 21

Pro Gly Ile Asn Gly Lys Ala Ile His Leu Val Asn Asn Gln Ser Ser
1               5                   10                  15

Glu

<210> SEQ ID NO 22
<211> LENGTH: 15
<212> TYPE: PRT
<213> ORGANISM: Artificial Sequence
<220> FEATURE:
<223> OTHER INFORMATION: synthetic construct

<400> SEQUENCE: 22

Gln Tyr Ile Lys Ala Asn Ser Lys Phe Ile Gly Ile Thr Glu Leu
1               5                   10                  15

<210> SEQ ID NO 23
<211> LENGTH: 21
<212> TYPE: PRT
<213> ORGANISM: Artificial Sequence
<220> FEATURE:
<223> OTHER INFORMATION: synthetic construct

<400> SEQUENCE: 23

Phe Asn Asn Phe Thr Val Ser Phe Trp Leu Arg Val Pro Lys Val Ser
1               5                   10                  15

Ala Ser His Leu Glu
            20

```
<210> SEQ ID NO 24
<211> LENGTH: 15
<212> TYPE: PRT
<213> ORGANISM: Artificial Sequence
<220> FEATURE:
<223> OTHER INFORMATION: synthetic construct

<400> SEQUENCE: 24

Leu Ser Glu Ile Lys Gly Val Ile Val His Arg Leu Glu Gly Val
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: synthetic construct

<400> SEQUENCE: 25

Phe Phe Leu Leu Thr Arg Ile Leu Thr Ile Pro Gln Ser Leu Asn
1               5                   10                  15

<210> SEQ ID NO 26
<211> LENGTH: 20
<212> TYPE: PRT
<213> ORGANISM: Artificial Sequence
<220> FEATURE:
<223> OTHER INFORMATION: synthetic construct

<400> SEQUENCE: 26

Thr Cys Gly Val Gly Val Arg Val Arg Ser Arg Val Asn Ala Ala Asn
1               5                   10                  15

Lys Lys Pro Glu
            20

<210> SEQ ID NO 27
<211> LENGTH: 31
<212> TYPE: PRT
<213> ORGANISM: Artificial Sequence
<220> FEATURE:
<223> OTHER INFORMATION: synthetic construct

<400> SEQUENCE: 27

Leu His Cys Pro Ala Leu Val Thr Tyr Asn Thr Asp Thr Phe Glu Ser
1               5                   10                  15

Met Pro Asn Pro Glu Gly Arg Tyr Thr Phe Gly Ala Ser Cys Val
            20                  25                  30

<210> SEQ ID NO 28
<211> LENGTH: 53
<212> TYPE: PRT
<213> ORGANISM: Artificial Sequence
<220> FEATURE:
<223> OTHER INFORMATION: synthetic construct

<400> SEQUENCE: 28

Lys Leu Leu Ser Leu Ile Lys Gly Val Ile Val His Arg Leu Glu Gly
1               5                   10                  15

Val Glu Gly Pro Ser Leu Leu His Cys Pro Ala Leu Val Thr Tyr Asn
            20                  25                  30

Thr Asp Thr Phe Glu Ser Met Pro Asn Pro Glu Gly Arg Tyr Thr Phe
        35                  40                  45

Gly Ala Ser Cys Val
    50
```

```
<210> SEQ ID NO 29
<211> LENGTH: 30
<212> TYPE: PRT
<213> ORGANISM: Artificial Sequence
<220> FEATURE:
<223> OTHER INFORMATION: synthetic construct

<400> SEQUENCE: 29

Val Ala Arg Cys Pro Ser Gly Val Lys Pro Asp Leu Ser Tyr Met Pro
1               5                   10                  15

Ile Trp Lys Phe Pro Asp Glu Glu Gly Ala Cys Gln Pro Leu
            20                  25                  30

<210> SEQ ID NO 30
<211> LENGTH: 52
<212> TYPE: PRT
<213> ORGANISM: Artificial Sequence
<220> FEATURE:
<223> OTHER INFORMATION: synthetic construct

<400> SEQUENCE: 30

Lys Leu Leu Ser Leu Ile Lys Gly Val Ile Val His Arg Leu Glu Gly
1               5                   10                  15

Val Glu Gly Pro Ser Leu Val Ala Arg Cys Pro Ser Gly Val Lys Pro
            20                  25                  30

Asp Leu Ser Tyr Met Pro Ile Trp Lys Phe Pro Asp Glu Glu Gly Ala
        35                  40                  45

Cys Gln Pro Leu
    50
```

HUMAN PD1 PEPTIDE VACCINES AND USES THEREOF

CROSS REFERENCE TO RELATED APPLICATIONS

This application is a national stage application filed under 35 U.S.C. § 371 of PCT/US2018/024831 filed Mar. 28, 2018, which claims the benefit of U.S. Provisional Application No. 62/477,895, filed on Mar. 28, 2017, applications which are incorporated herein by reference in their entirety.

I. BACKGROUND

Cancer is now the primary cause of death in developed countries and world-wide. The financial burden of this disease, and more importantly, the suffering it causes, is immense. There is an obvious and urgent need to speed the development and application of new, more efficacious anti-cancer therapies. The field of oncology is vast and comprises several indications, including some rare/orphan forms. Although oncology continues to be one of the most active areas in terms of drug development, there is still a significant unmet need.

Recent advances in cancer immunology have documented the importance of T cell-mediated anti-tumor immunity against human cancers, and inhibitory receptors expressed by T cells have become important targets for cancer immunotherapy. Signaling through the immune checkpoint programmed cell death protein-1 (PD-1) enables tumor progression by dampening antitumor immune responses. Therapeutic blockade of the signaling axis between PD-1 and its ligand programmed cell death ligand-1 (PD-L1) with monoclonal antibodies has shown remarkable clinical success in the treatment of cancer and demonstrated impressive activity across a broad set of cancer subtypes, even at advanced and metastatic stages of disease. Therapeutics targeting this pathway are currently in clinical trials. Pembrolizumab and nivolumab are the first of this anti-PD-1 pathway family of checkpoint inhibitors to gain accelerated approval from the US Food and Drug Administration (FDA) for the treatment of ipilimumab-refractory melanoma.

Monoclonal antibodies targeting immunologic checkpoints and especially the PD-1/PD-L1 axis provided spectacular results in cancer therapy in the recent years. Despite their proven utility, antibodies have specific drawbacks as therapeutics, including poor tissue/tumor penetrance which may be especially pertinent when targeting the PD-1:PD-L1 signaling pathway. For example, PD-1-expressing effector T cells are found infiltrated within solid tissue of PD-L1-expressing tumors. This is problematic for antibodies, which are impeded from entering tumors due to their large size. It follows that antibodies may therefore fail to completely antagonize PD-1:PD-L1 signaling at the intended therapeutic site within tumors, leading to suboptimal efficacy.

Checkpoint blockades turn on a new paradigm shift in immunotherapy for cancer. However, a lot of cancer patients failed to respond to the PD-1/PD-L1 checkpoint blockades. What are needed are new PD-1/PD-L1 checkpoint inhibitors for the treatment of cancer, viral infections, autoimmune diseases and Alzheimer's disease.

II. SUMMARY

Disclosed are methods and compositions related to synthetic PD-1 peptides.

In one aspect, disclosed herein are PD-1 chimeric peptides for stimulating an immune response to a PD-1 protein comprising one or more PD-1 B cell epitopes, a T helper (Th) epitope (for example, a measles virus fusion protein peptide such as SEQ ID NO: 6), and a linker (such as, for example, SEQ ID NO: 7) joining the PD-1 B cell epitope to the Th epitope, wherein the one or more PD-1 B cell epitopes consist of a sequence selected from the group consisting of SEQ ID NO:2, SEQ ID NO:3, SEQ ID NO:4, and SEQ ID NO:5.

Also disclosed herein are chimeric peptides of any preceding aspect, wherein the peptide comprises the amino acid sequence as set forth in SEQ ID NO: 8, SEQI DNO: 9, SEQ ID NO:10 or SEQ ID NO:11.

In one aspect, disclosed herein are synthetic PD-1 peptides for stimulating an immune response to a PD-1 protein comprising one or more of the sequences as set forth in SEQ ID NO: 12, SEQ ID NO: 13, SEQ ID NO: 14, or SEQ ID NO: 15 including the D enantiomer of the disclosed sequences. In one aspect, the synthetic peptide can be acetylated.

Also disclosed herein are chimeric peptides comprising the synthetic peptide of any preceding aspect, further comprising a Th epitope (for example, a measles virus fusion protein peptide such as SEQ ID NO: 6), and a linker (such as, for example, SEQ ID NO: 7) joining the synthetic PD-1 peptide to the Th epitope.

Also disclosed herein are chimeric peptides of any preceding aspect, wherein the peptide comprises the amino acid sequence as set forth in SEQ ID NO: 16, SEQ ID NO: 17, SEQ ID NO: 18, or SEQ ID NO: 19.

In one aspect, disclosed herein are pharmaceutical compositions comprising one or more chimeric or synthetic peptides of any preceding and a pharmaceutically acceptable vehicle.

Also disclosed are pharmaceutical compositions of any preceding aspect further comprising one or more HER-2 B cell epitopes (such as for example, SEQ ID NO: 27, SEQ ID NO: 28, SEQ ID NO: 29, or SEQ ID NO: 30) and/or one or more anti-Her-2 antibodies.

In one aspect, disclosed herein are methods of treating a cancer, Alzheimer's disease, or autoimmune disease in a subject comprising administering to the subject any of the peptides or compositions of any preceding aspect.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows close-up views of the hPD-1/hPD-L1 Interface hPD-1 and hPD-L1 are represented by blue and green ribbons, respectively. All residues important for the interaction are highlighted as sticks. Residues forming the hydrophobic core are colored yellow. Water molecules are shown as red spheres. Hydrogen bonds are depicted as black dashed lines. (A) Front-side view Zak et al., 2015, Structure 23, 2341-2348. (B) PD-1 peptides modelled.

Figure 2B:
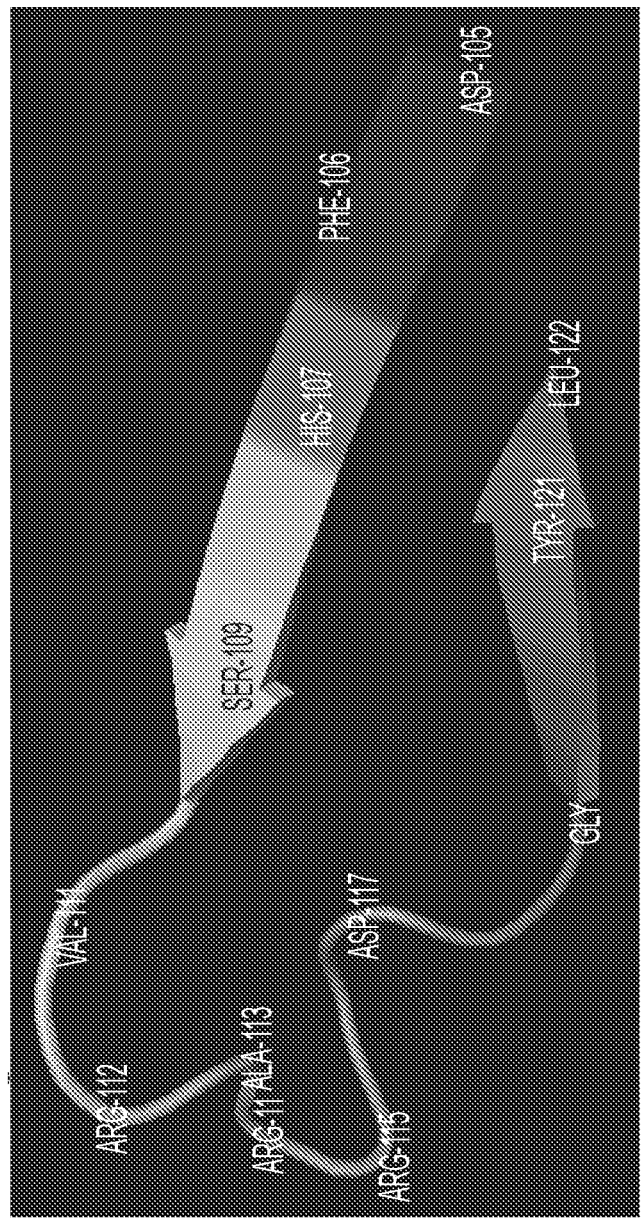
Figure 2C:
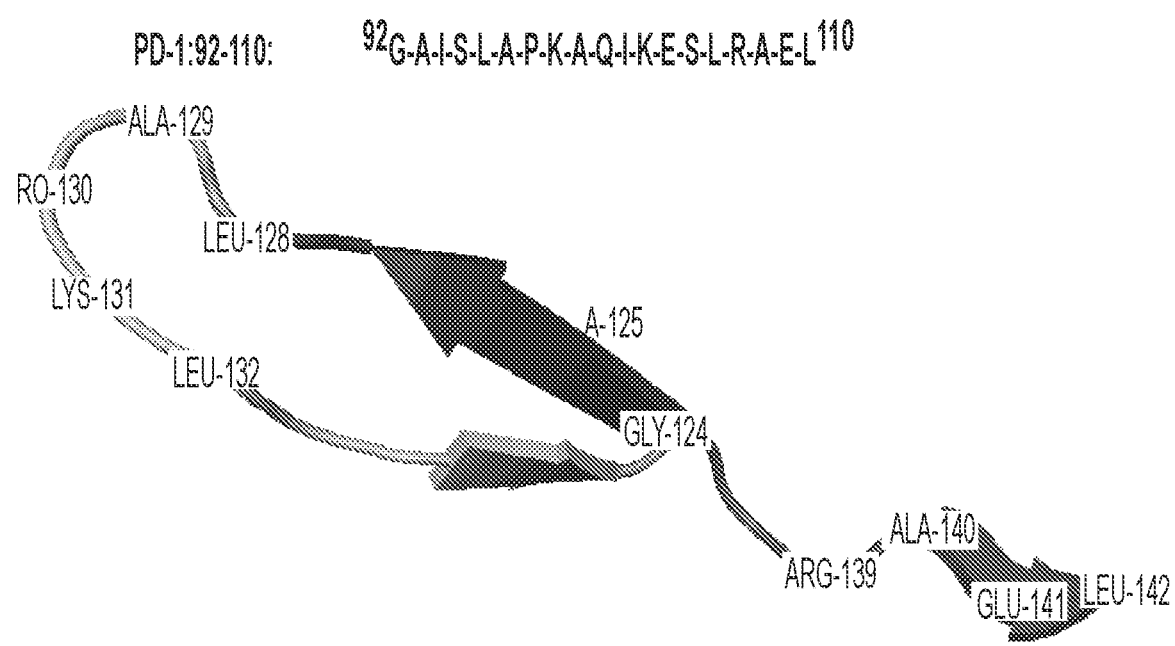

FIGS. 2A, 2B, and 2C show modeling of the PD-1 Peptides as conformation epitopes. FIG. 2A shows PD-1 (32-50)(SEQ ID NO: 2). FIG. 2B shows PD-1 (73-90))(SEQ ID NO: 4). FIG. 2C shows PD-1 (92-110))(SEQ ID NO: 5).

Figure 3A:
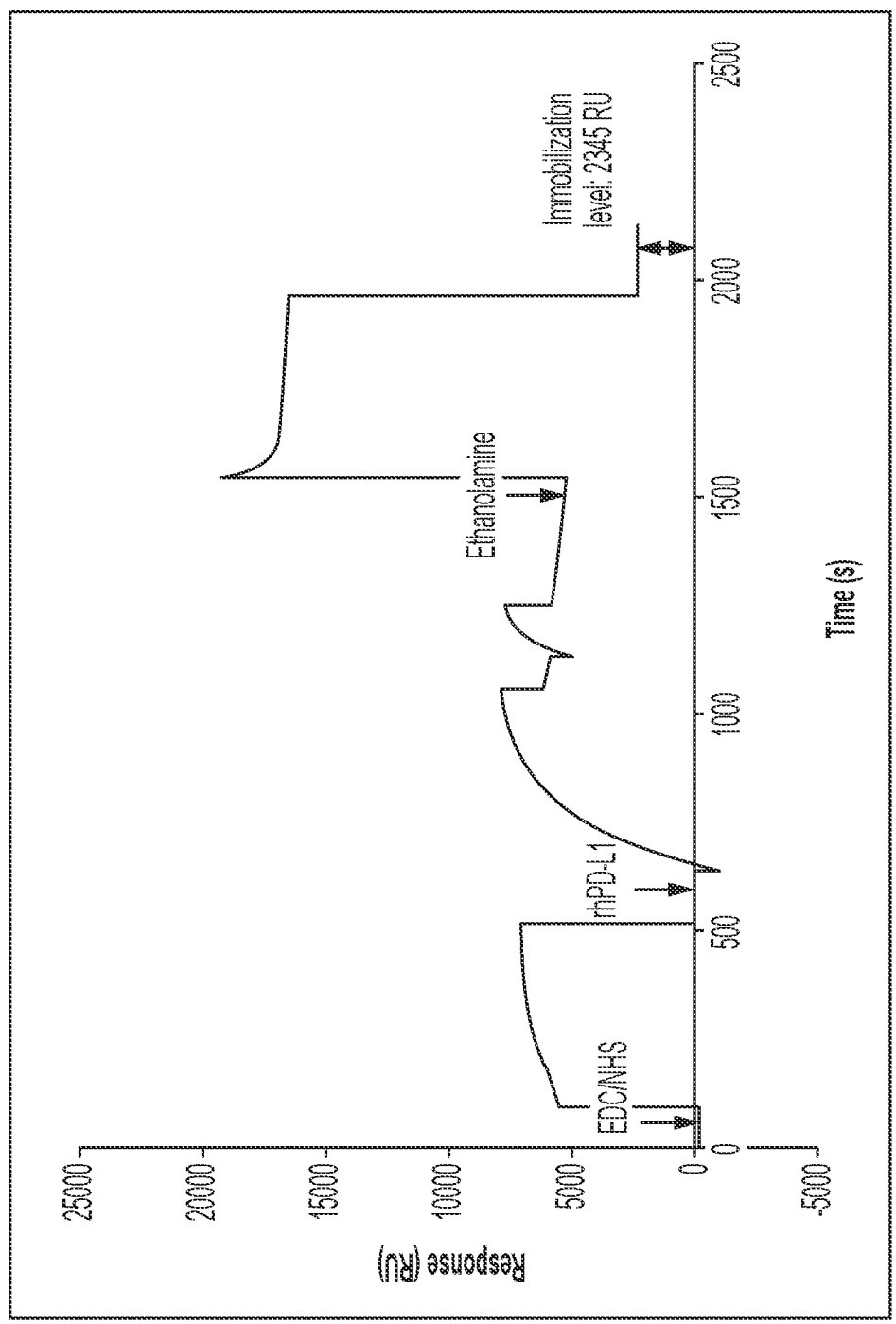
Figure 3B:
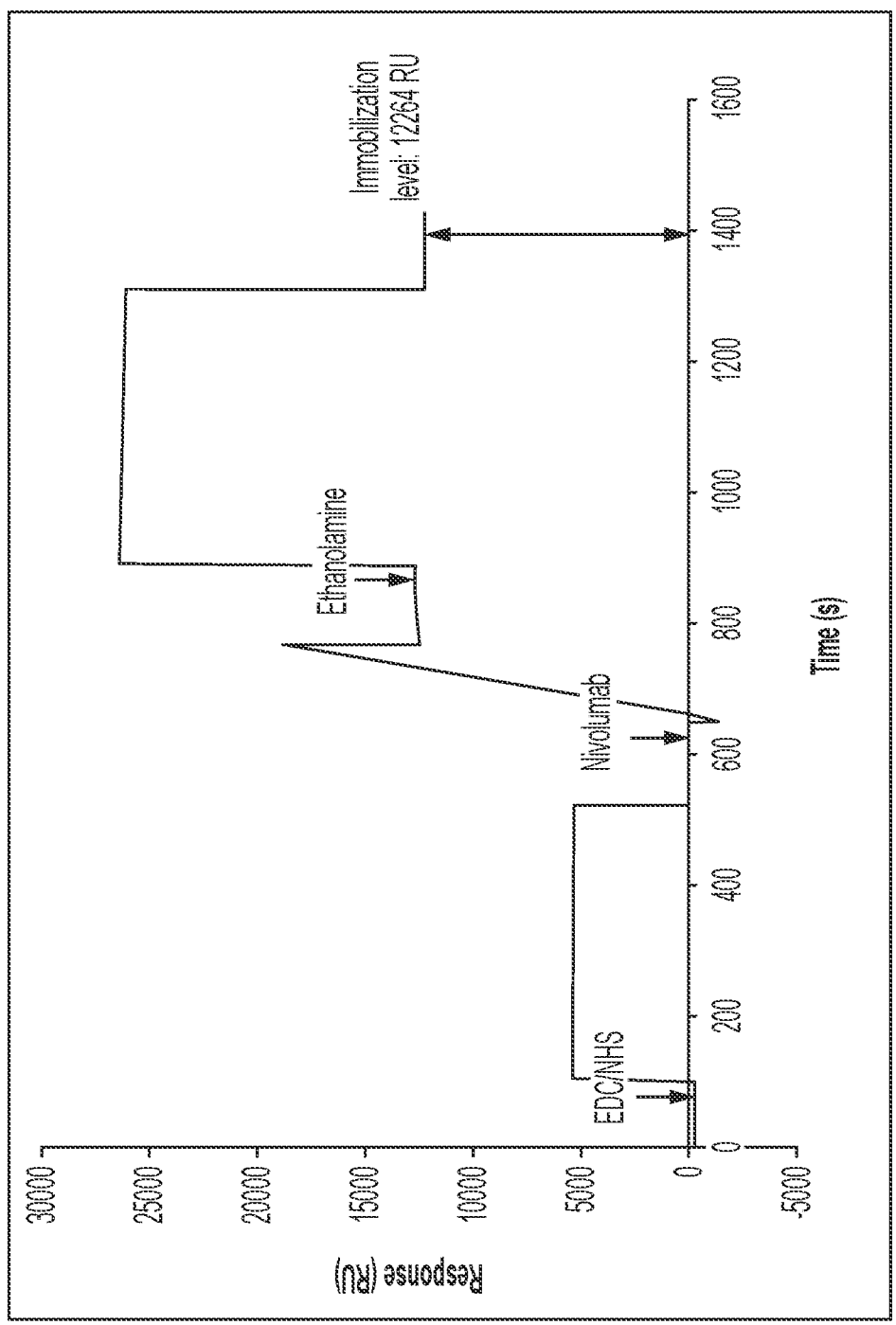
Figure 3C:
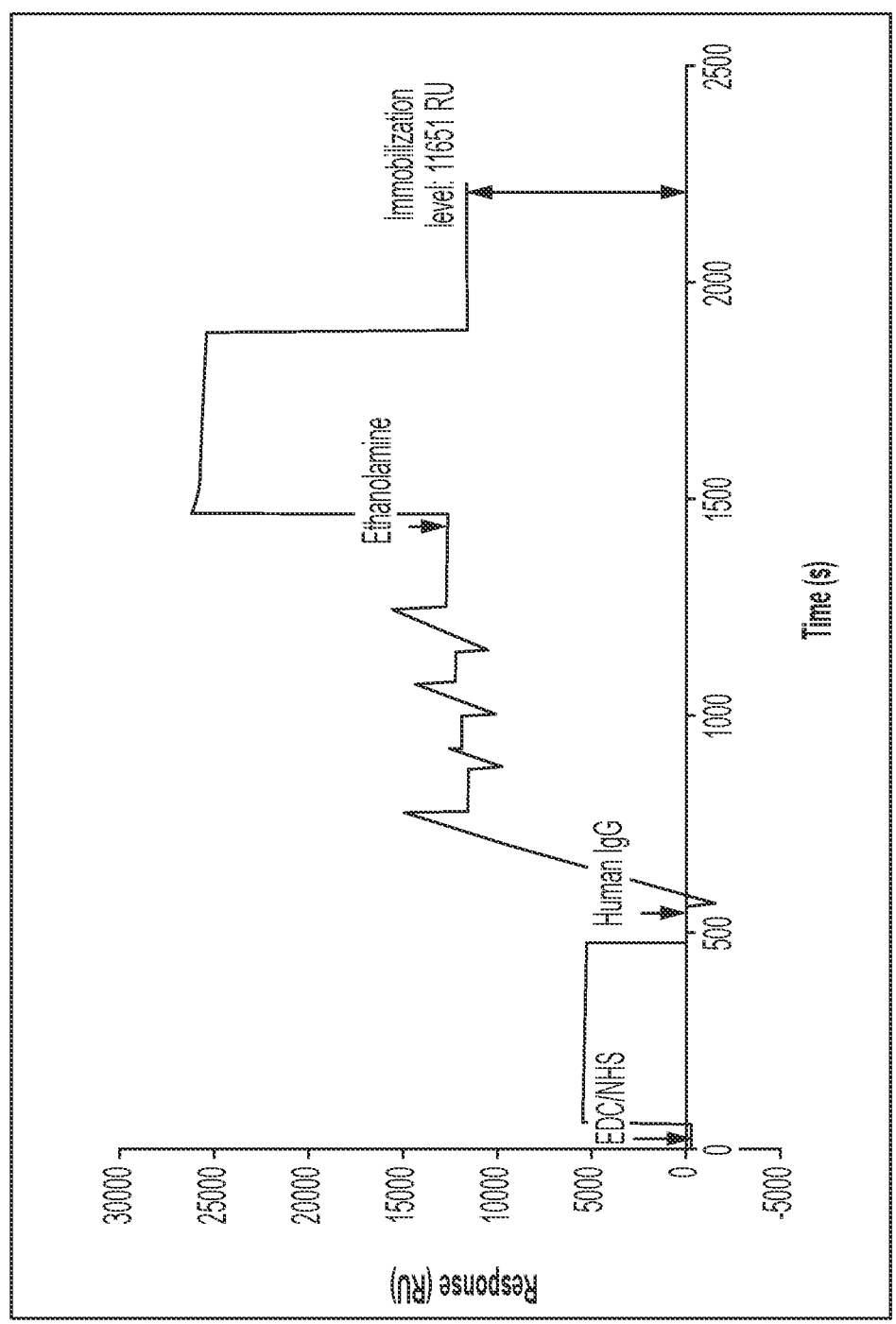
Figure 3D:
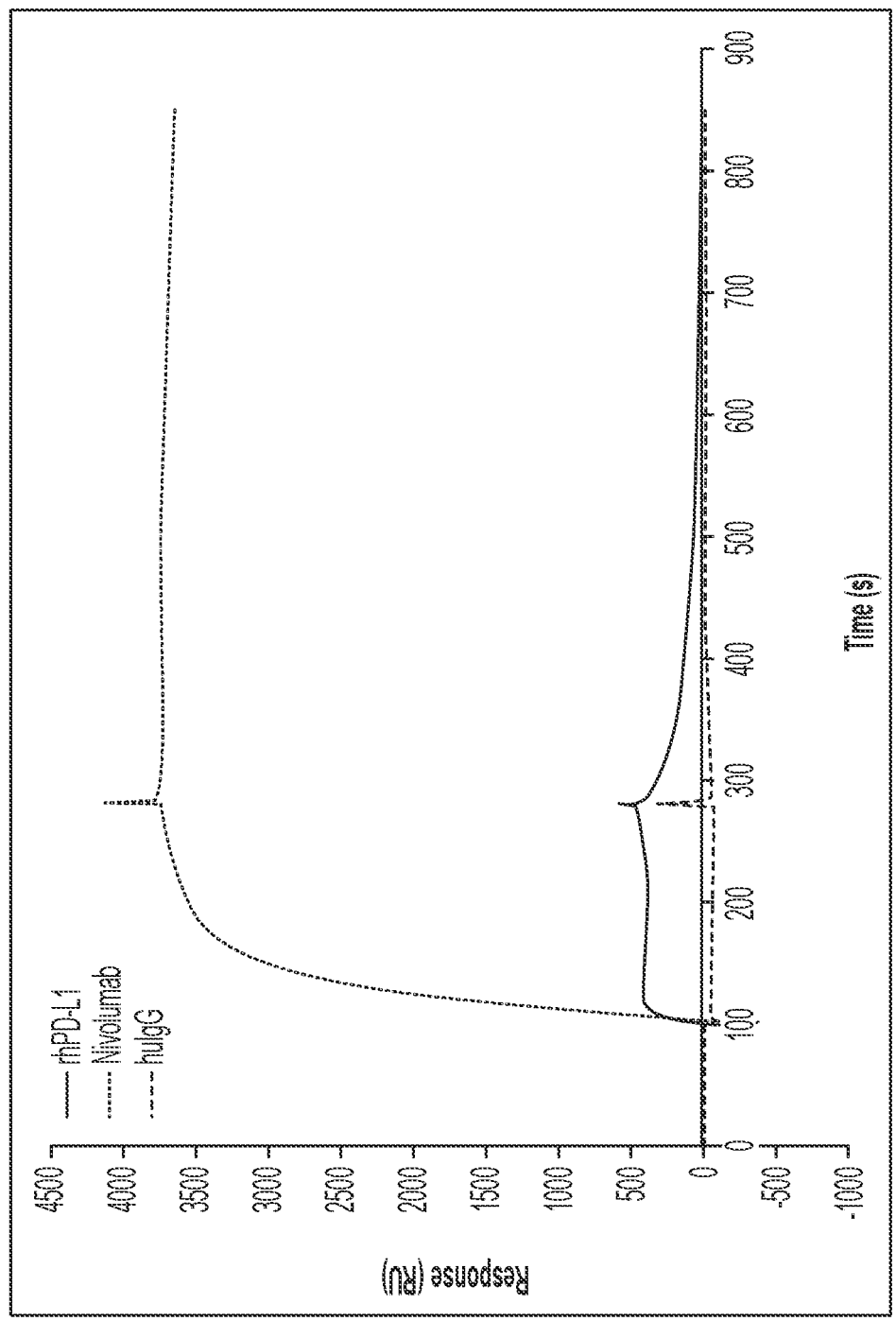
Figure 3E:
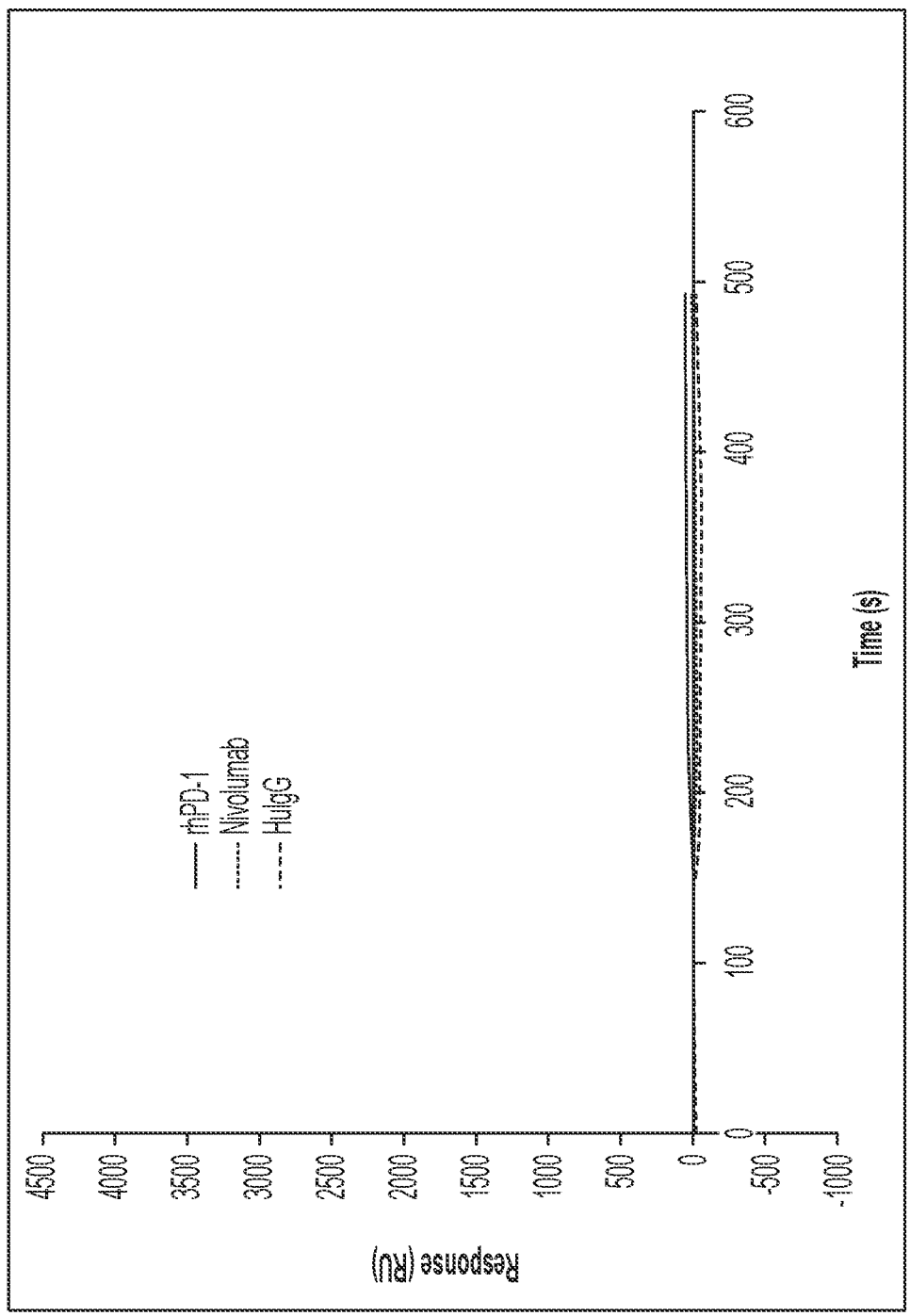

FIGS. 3A, 3B, 3C, 3D, and 3E show surface plasmon resonance spectroscopy for binding experiments to the extracellular domain of human hPD-L1. The resulting immobilization levels for rhPD-L1 (FIG. 3A), Nivolumab (FIG. 3B), Human IgG (FIG. 3C) are 2345 RU, 12264 RU and 11651 RU respectively. Validation of the sensor chip was shown by measuring the specificity of fhPD-1 and Nivolumab binding. 1 µM (17.3 µg/ml) rhPD-1 was injected over the chip for 3 min at 10 µl/min (FIG. 3D). 1 µM BSA was used as the negative control. The chip was regenerated by 10 mM Glycine-HCl, pH 2.5 (FIG. 3E).

Figure 4A:
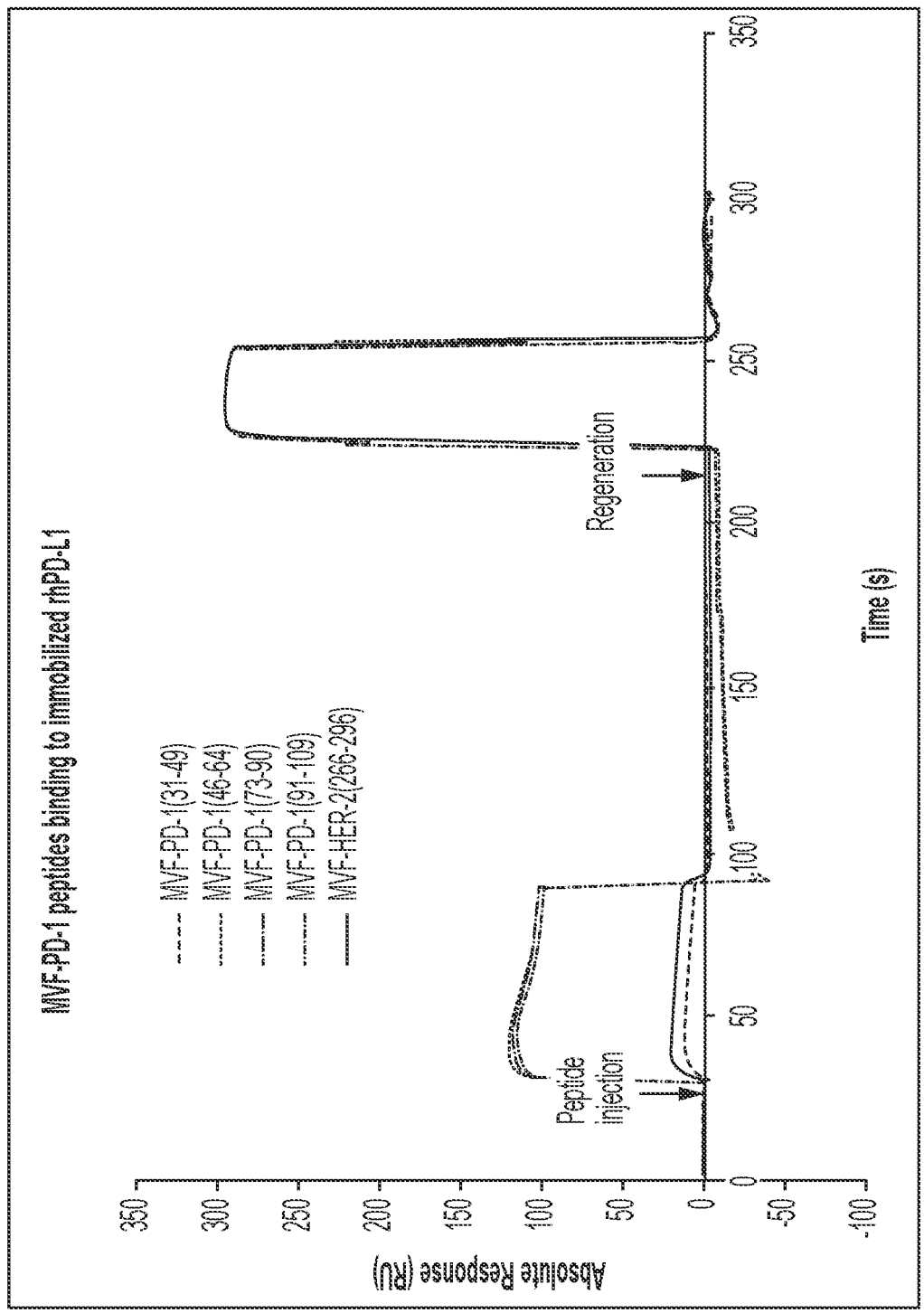
Figure 4B:
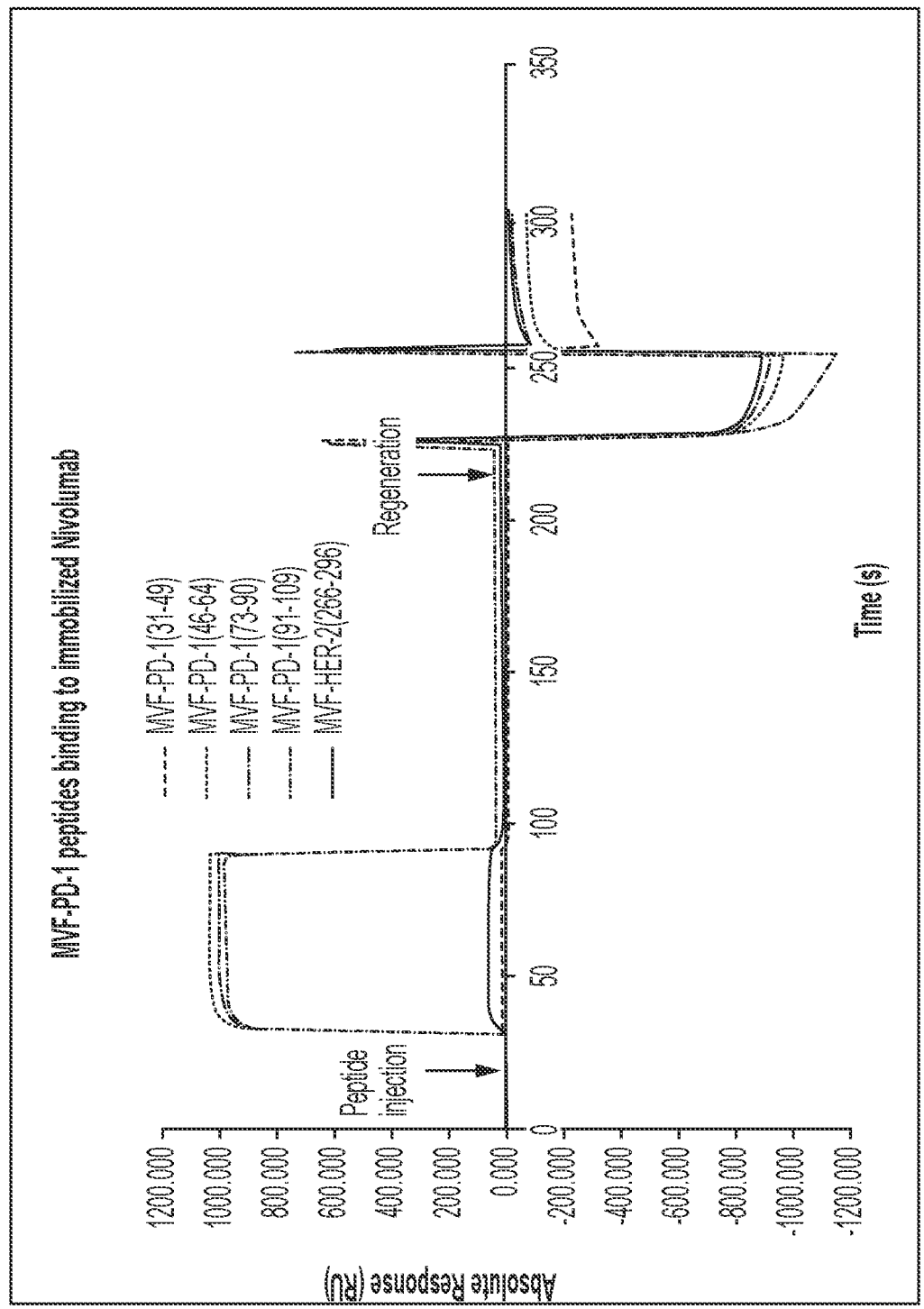
Figure 4C:
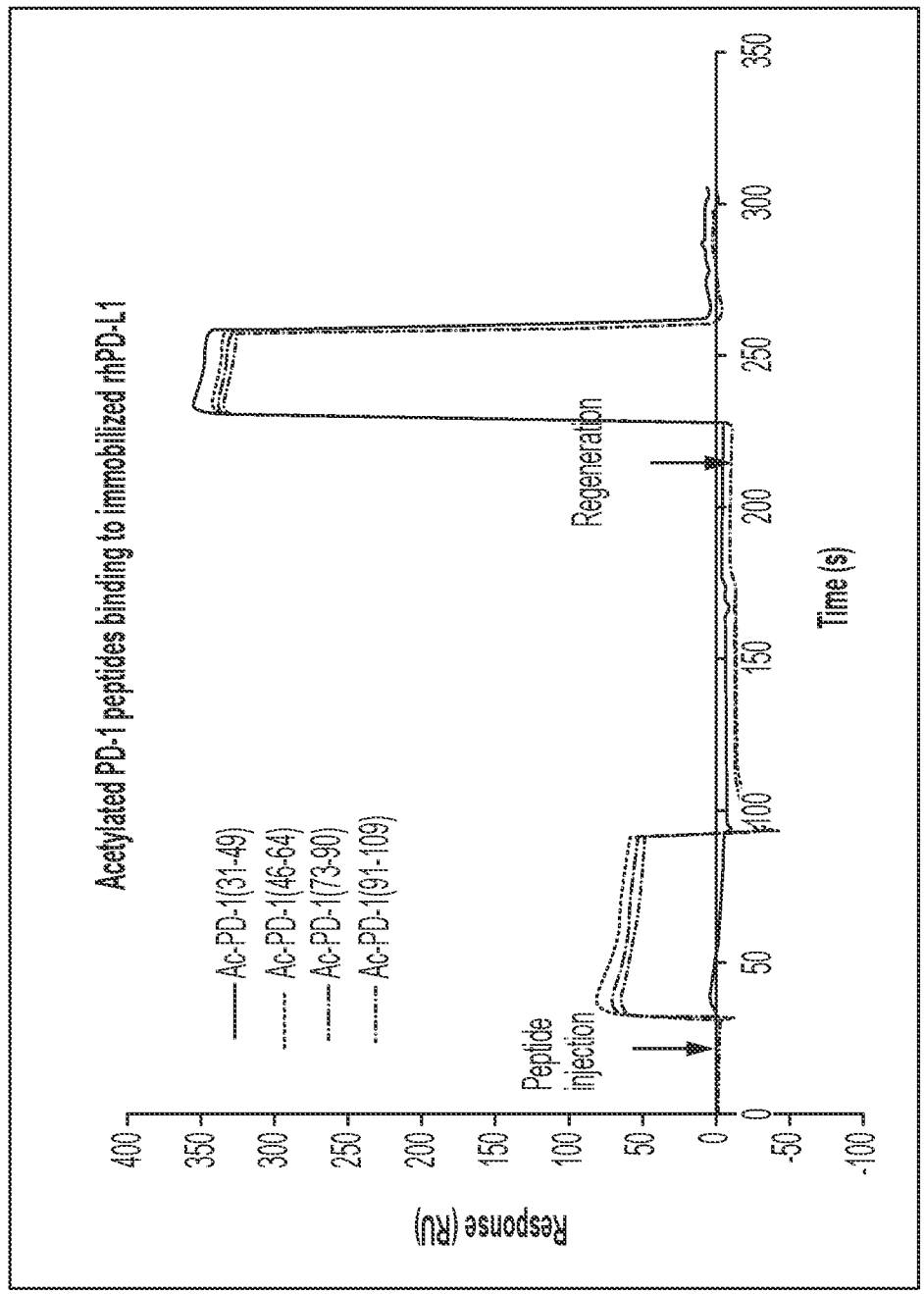
Figure 4D:
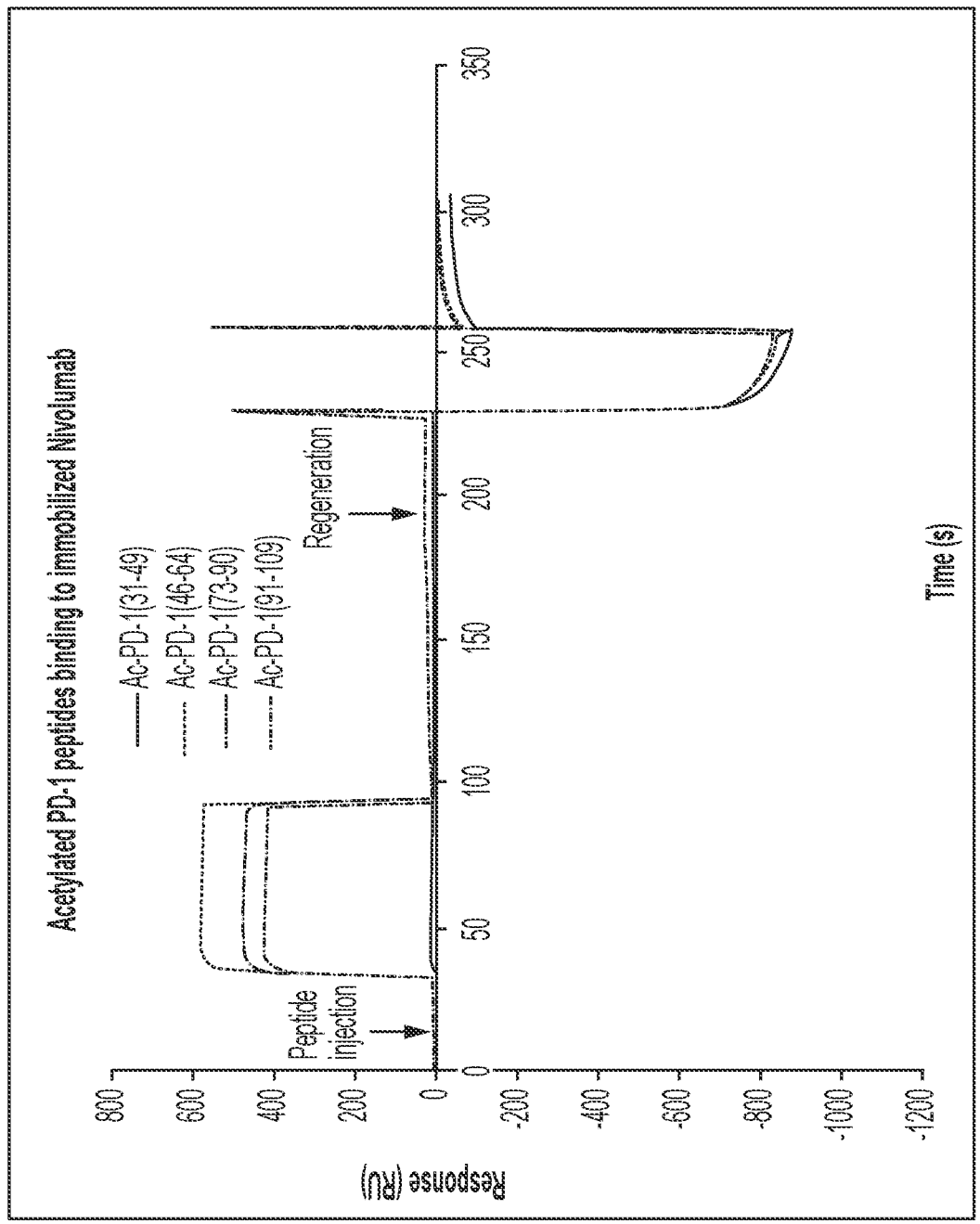
Figure 4E:
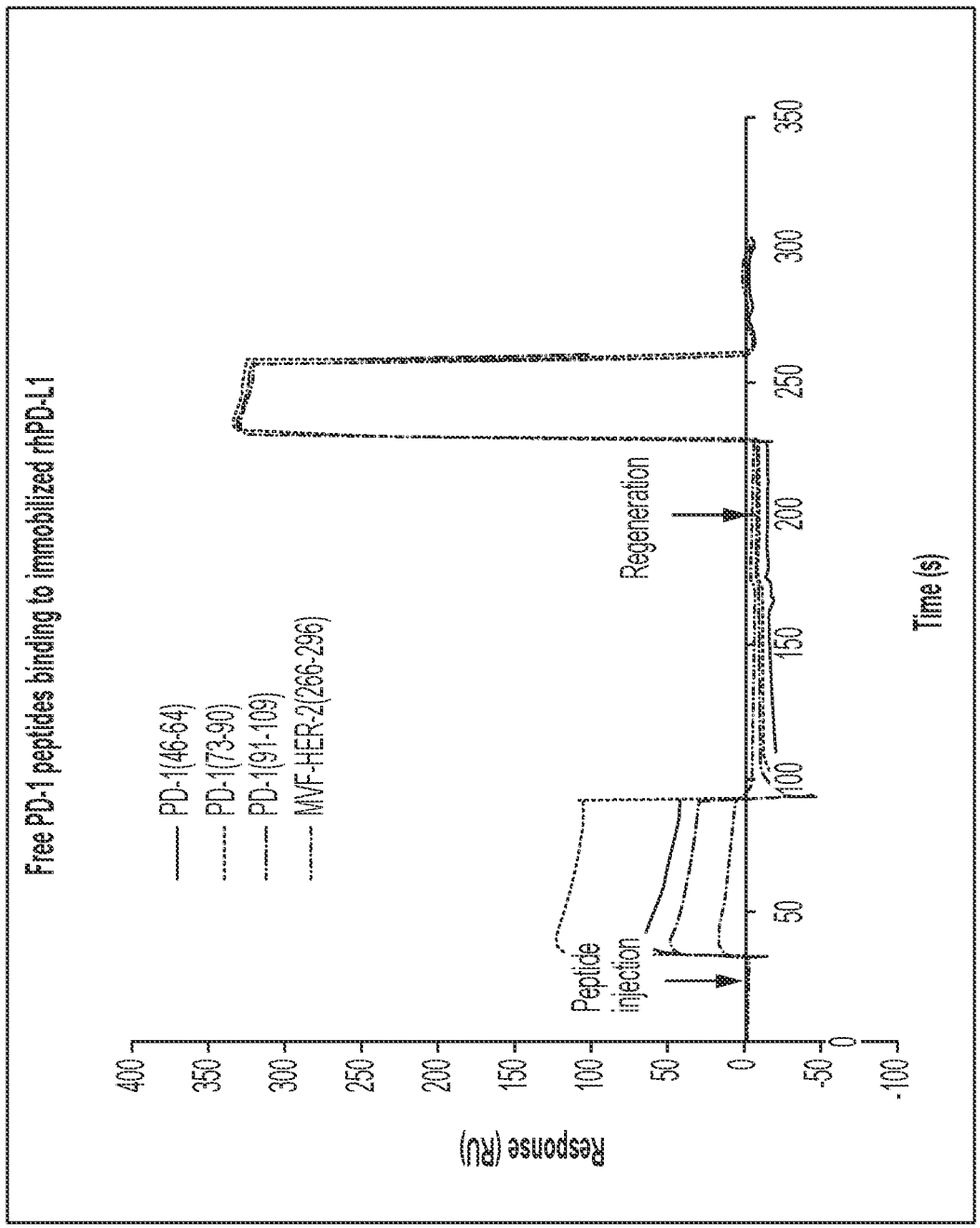
Figure 4F:
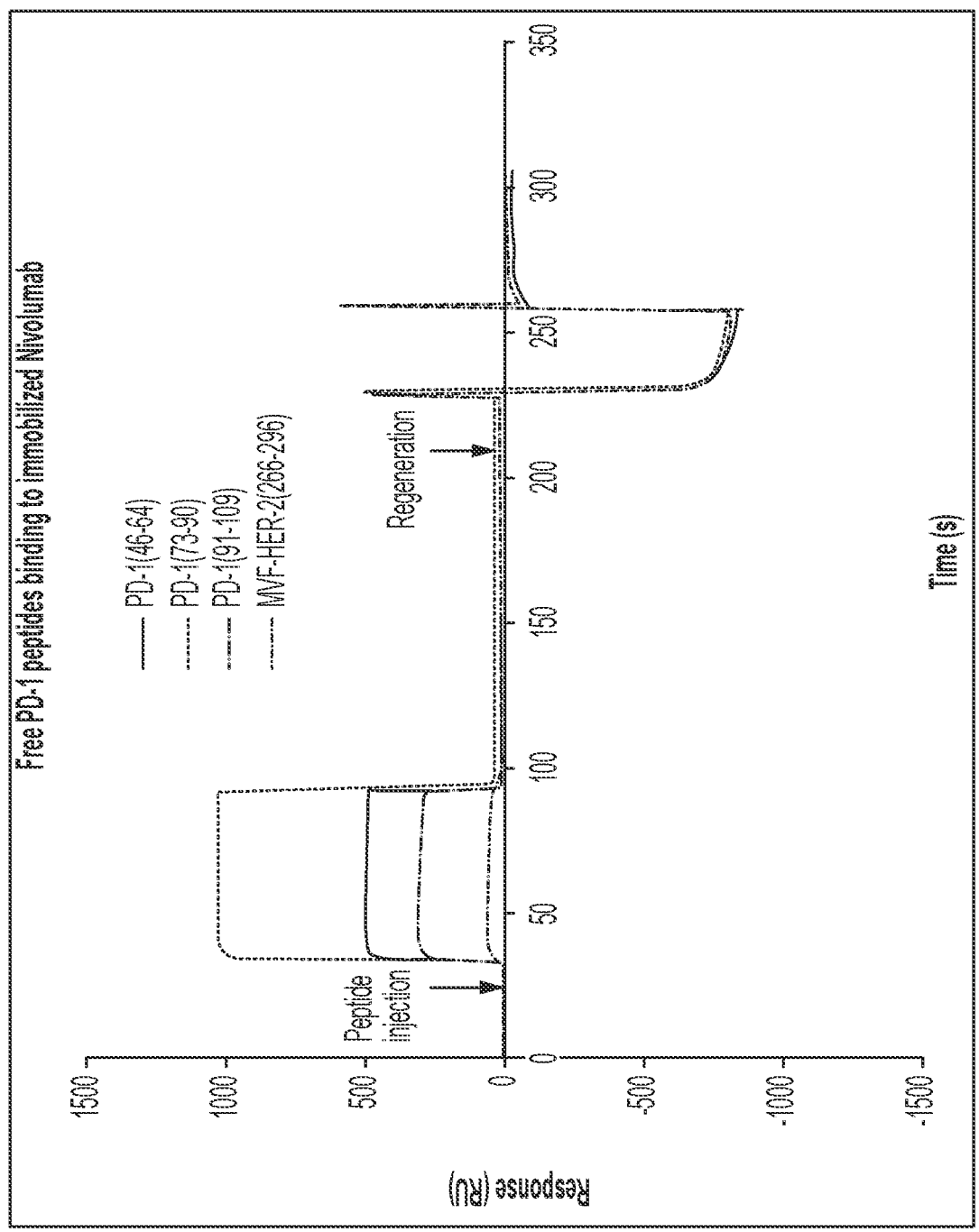

FIGS. 4A, 4B, 4C, 4D, 4E, and 4F show that MVF peptides and acetylated peptides bind to rhPD-L1 and Nivolumab. MVF-PD-1 (45-64), MVF-PD-1 (73-90), MVF-PD-1 (92-110) bind to immobilized rhPD-L1 (FIG. 4A) or Nivolumab (FIG. 4B). Ac-PD-1 (45-64), Ac-PD-1 (73-90), Ac-PD-1 (92-110) bind to immobilized rhPD-L1 (FIGS. 4C and 4D) or Nivolumab (FIGS. 4E and 4F).

Figure 5A:
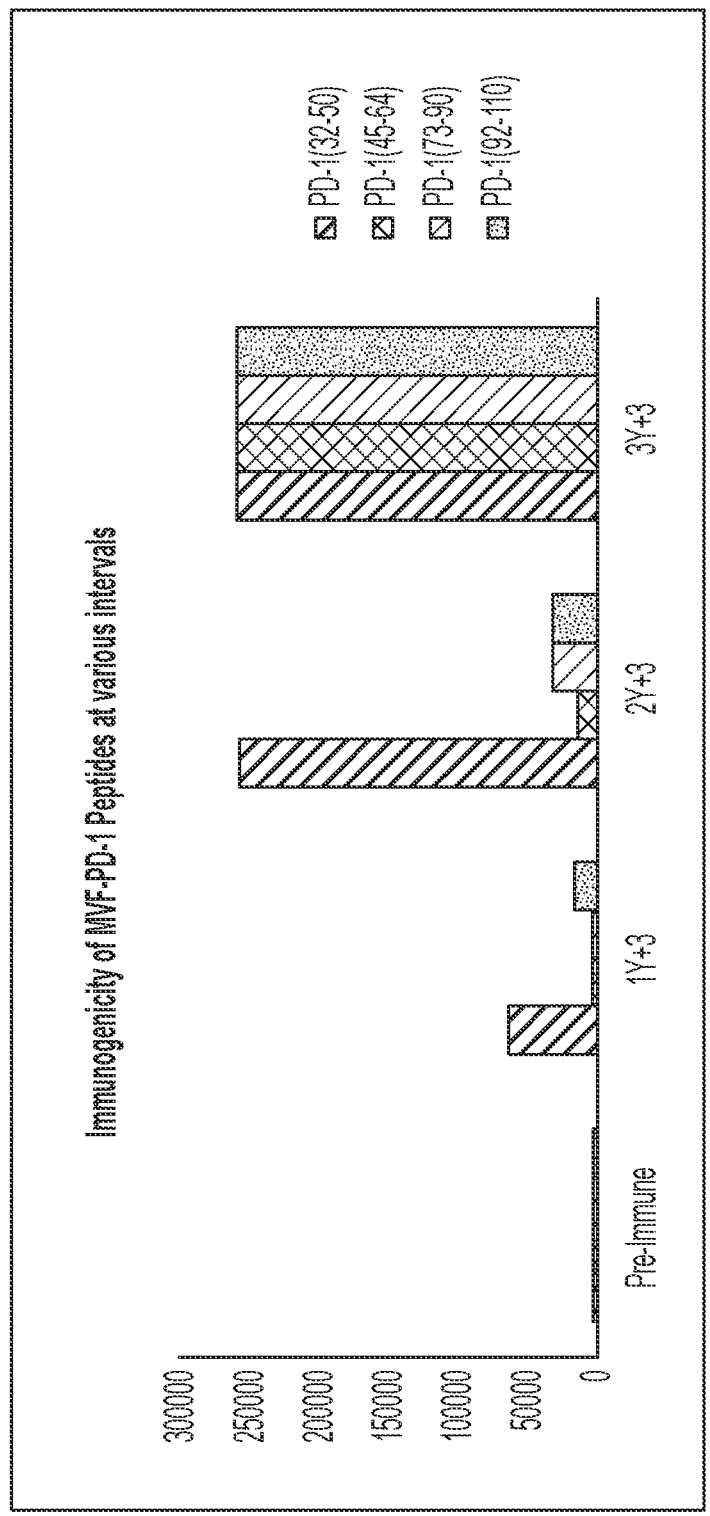

FIG. 5A shows the 1st (1Y+3) 3rd (2Y+3) and 6th (3Y+3) test bleeds were tested by ELISA on 200 ng/well of MVF-peptide or. Sera was initially diluted to 1:2000 and then serially diluted down the plate to a maximum of 1:250,000. ABTS was used as a substrate in the assay. Titers were defined as the final dilution that still had an absorbance >than 0.200 when read at 415λ.

Figure 5B:
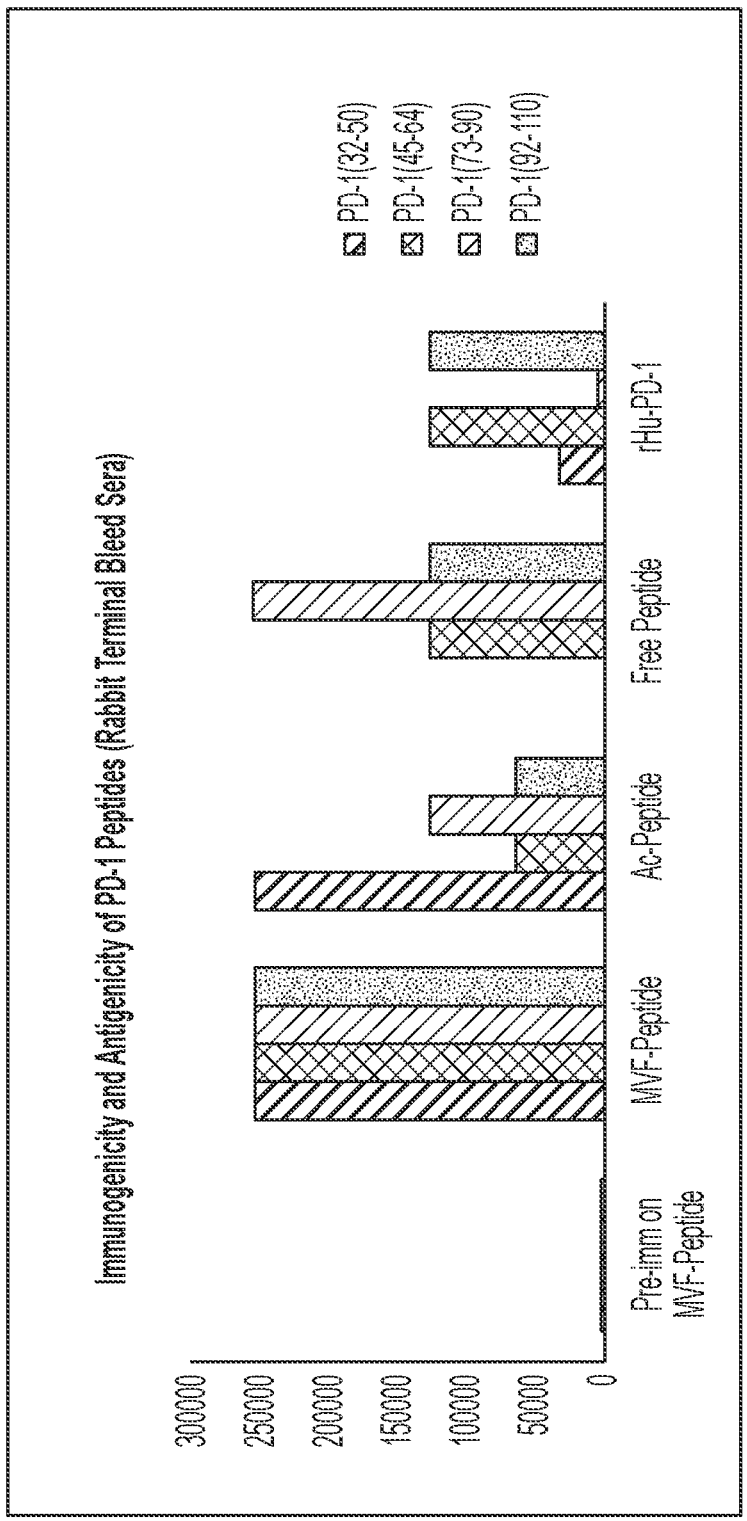

FIG. 5B shows that terminal bleed sera were tested by ELISA on 200 ng/well of the various peptide constructs (MVF-peptide, acetylated peptide, free peptide and recombinant human PD-1 protein. Sera was initially diluted to 1:2000 and then serially diluted down the plate to a maximum of 1:250,000. ABTS was used as a substrate in the assay. Titers were defined as the final dilution that still had an absorbance >than 0.200 when read at 415λ.

Figure 5C:
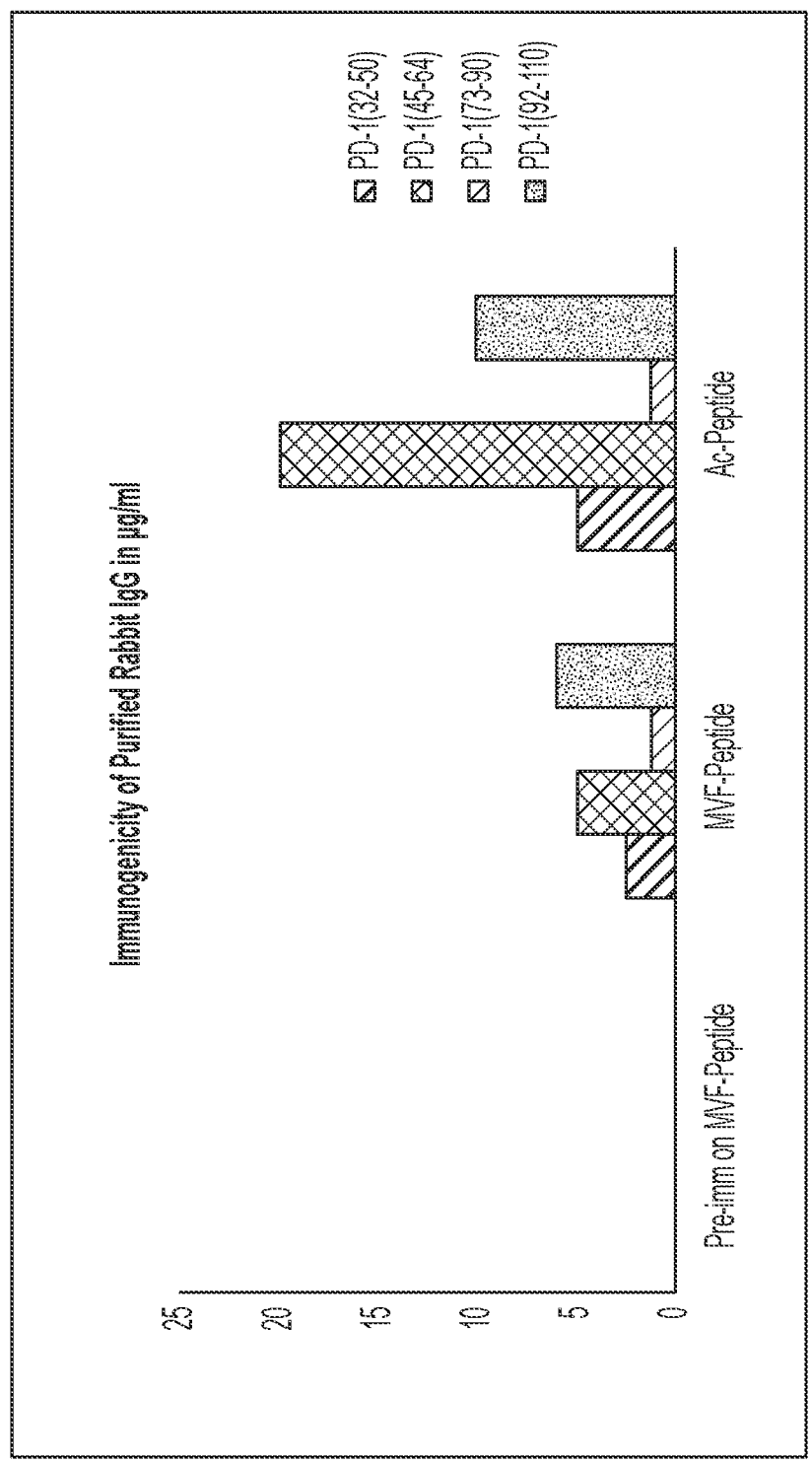

FIG. 5C shows an antibody purified from the terminal sera was tested by ELISA on 200 ng/well of peptide. Antibody was initially diluted to 20 µg/ml and then serially diluted down the plate to a maximum of 625 ng/ml. ABTS was used as a substrate in the assay. Titers were defined as the final dilution that still had an absorbance >than 0.200 when read at 415λ.

Figure 6:
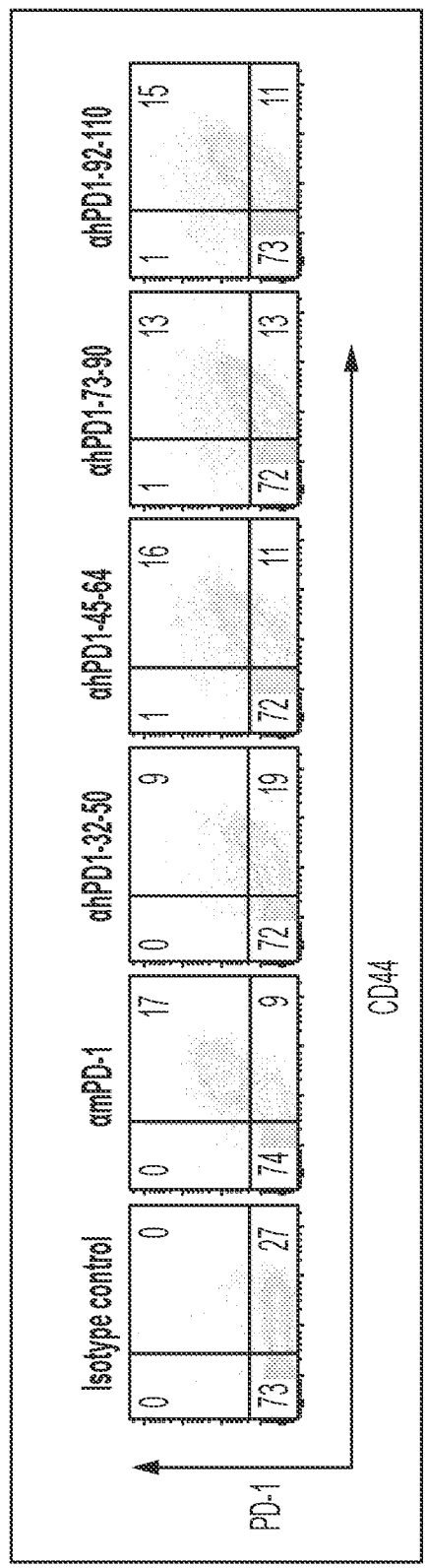

FIG. 6 shows that splenocytes from naïve TCR transgenic mice were activated with MBP Ac1-11 for 3 days. PD-1 expression was determined by flow cytometry. Cells were stained with α-mPD-1 or α-hPD-1 antibodies as labeled. Cells were gated on CD4+ T cells.

Figure 7:
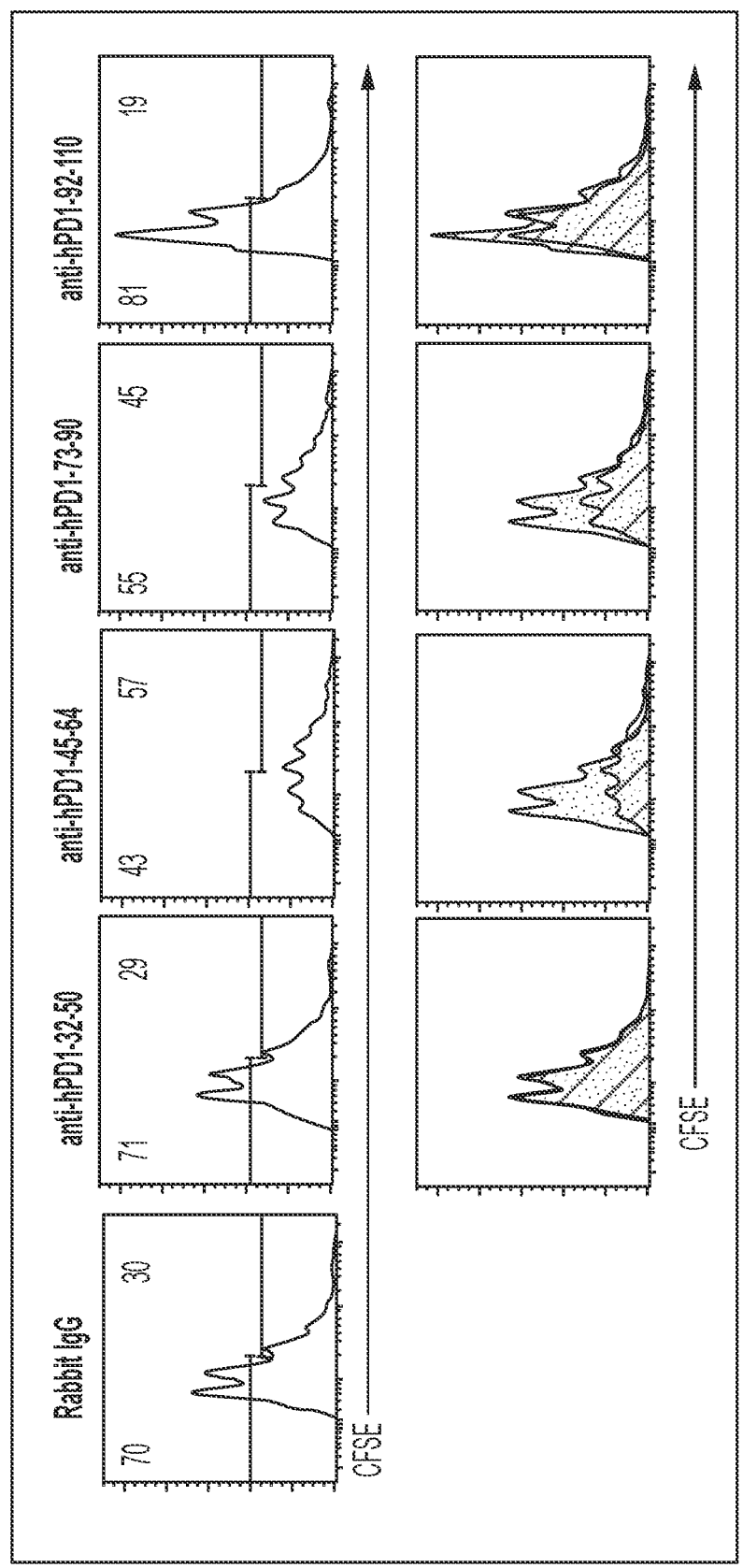

FIG. 7 shows purified α-hPD-1 polyclonal antibodies alter antigen-specific proliferation of myelin-specific CD4 T cells. (A) Splenocytes from naïve TCR transgenic mice were labeled with CFSE and activated with MBP Ac1-11 in the presence of 50 mg/ml of αhPD-1 antibodies or control rabbit IgG for 4 days. Cells were gated on CD4+ cells. (B) Overlay of CFSE histogram of cells treated with specific αhPD-1 antibody (blue) with those treated with control rabbit IgG (red) in (A).

Figure 8:
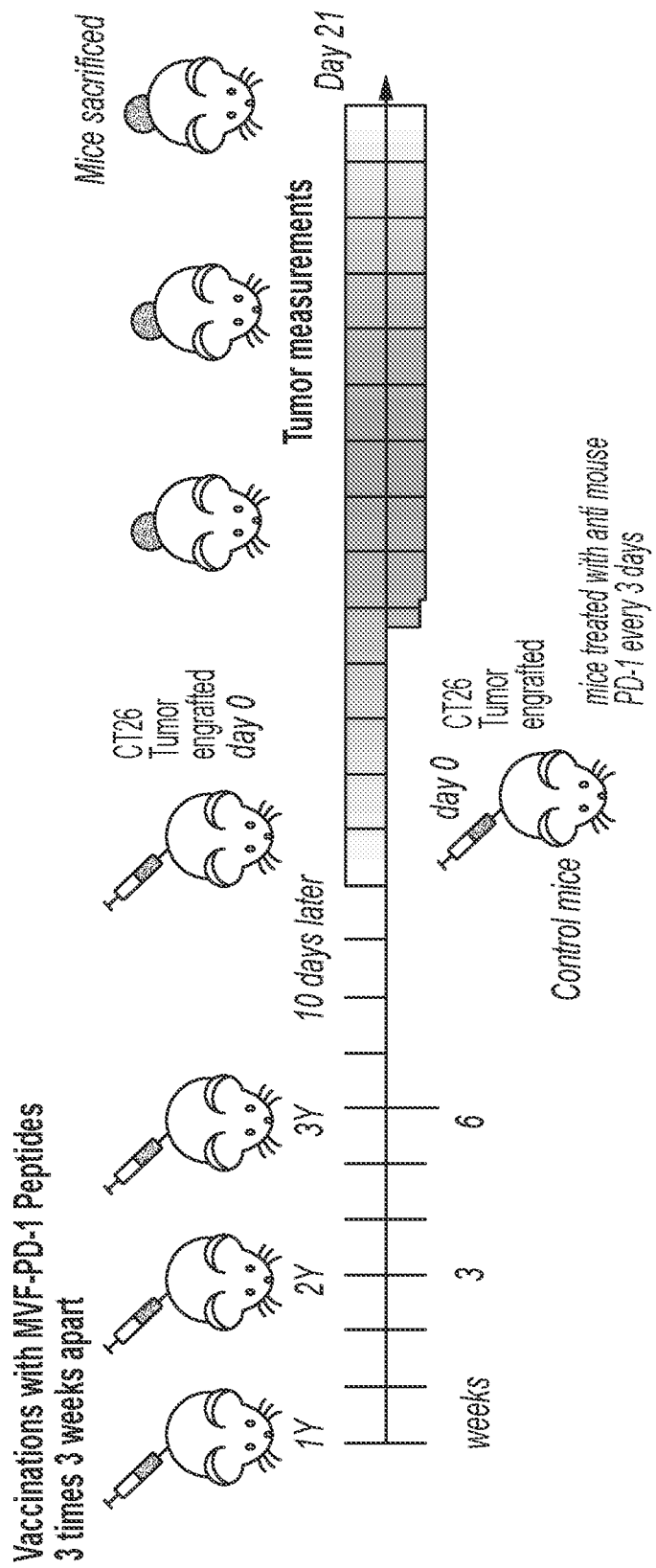

FIG. 8 shows a scheme of mice vaccination and tumor engraftment. Mice received a total of 3 vaccinations at 3 weeks interval. 10 days after the 3rd vaccination mouse were challenged $1\times10^5$ murine colon carcinoma CT26 tumor cells subcutaneous on the right flank. Control mice were inoculated with CT26 cell line and treated every 3 days with a mouse pD-1 monoclonal antibody.

Figure 9:
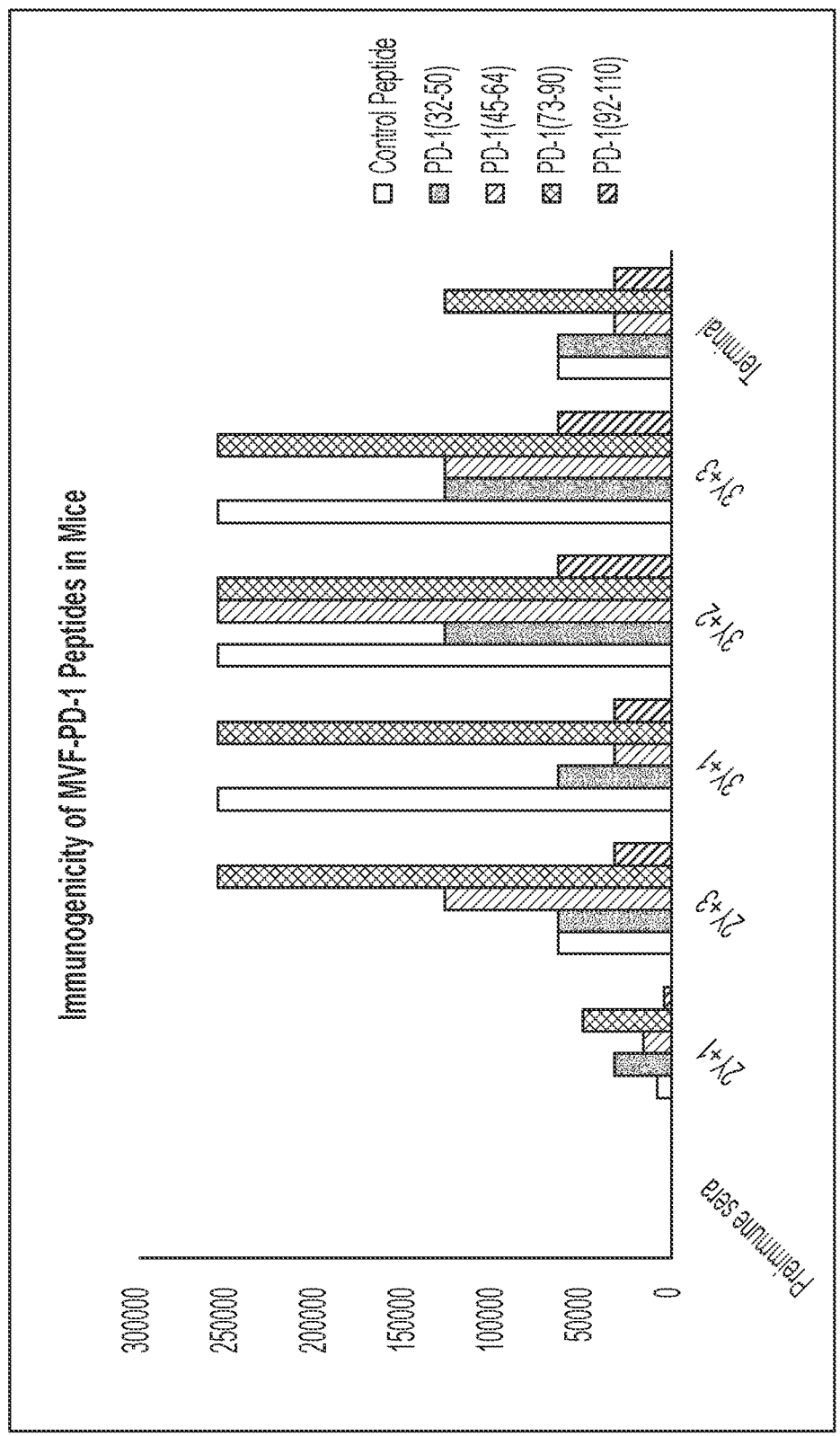

FIG. 9 shows the immunogenicity of PD-1 vaccines. Sera pools were tested by ELISA on 200 ng/well of MVF-peptide. Sera concentrations from 1:100-1:250,000 were tested. ABTS was used as a substrate in the assay. Titers were defined as the final dilution that still had an absorbance >than 0.200 when read at 415λ.

Figure 10A:
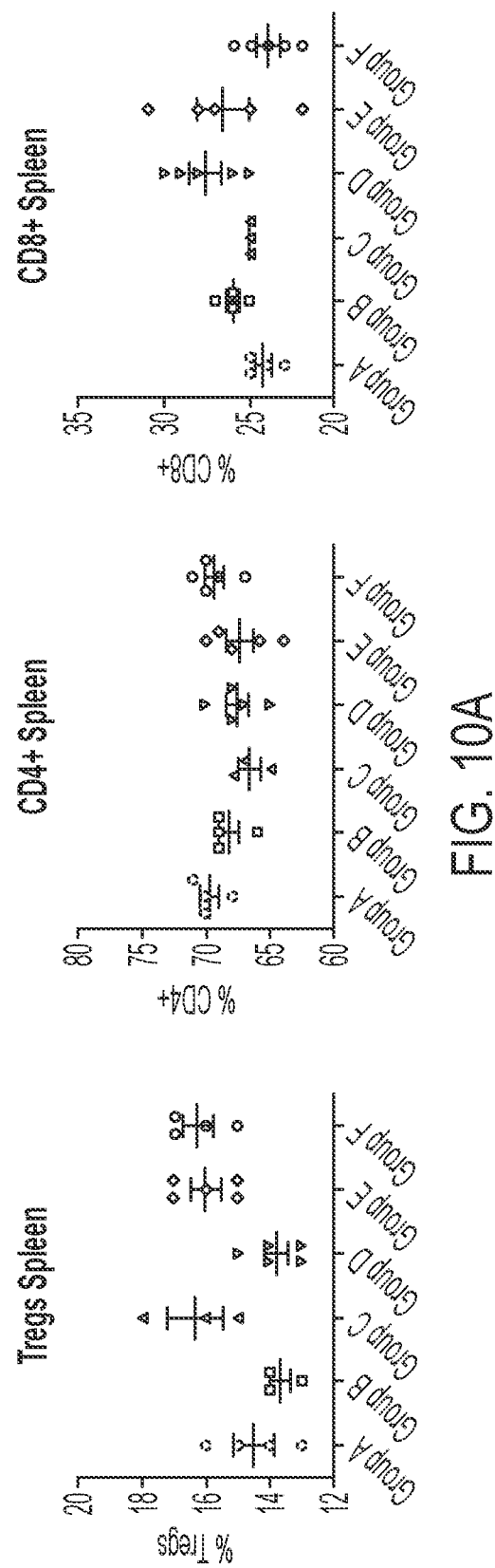
Figure 10B:
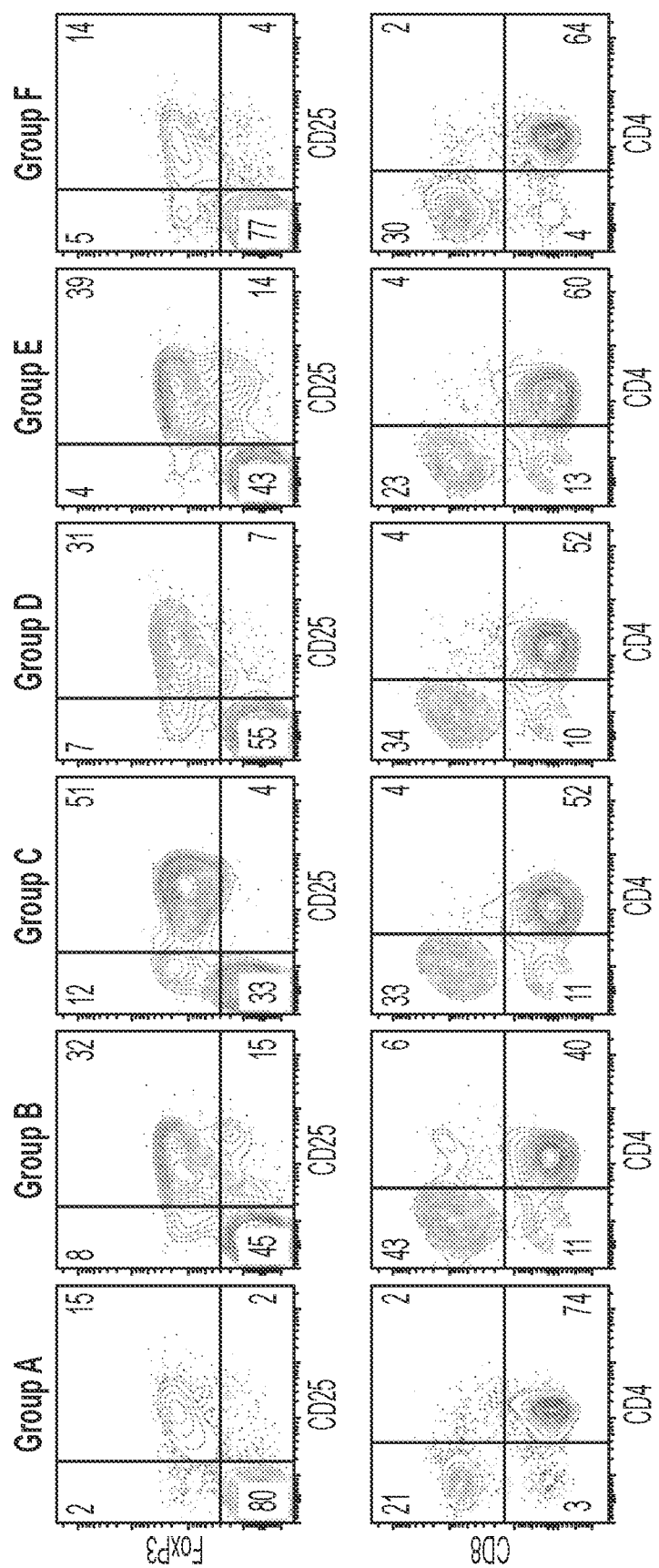

FIG. 10 shows splenocytes (A) and tumor infiltrating cells (B) were isolated from all 5 groups of treated mice. CD4 and CD8 cells were determined by flow cytometry (gated on CD45+CD3+ cells). Foxp3+CD25+CD4 T regulatory cells were determined by intracellular staining. All CD4 and CD8 T cells were gated on CD45+CD3+ cells. Tregs were gated on CD45+CD3+CD4+ cells. Group A=control peptide, Group B=32-50; Group C=45-64; Group D=73-90; Group E=92-110; Group F=α-mouse PD-1 (positive control).

Figure 11A:
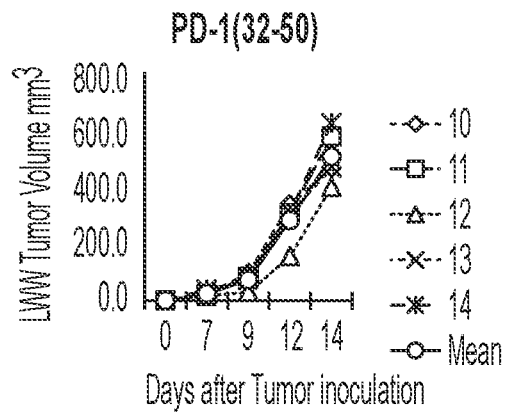
Figure 11B:
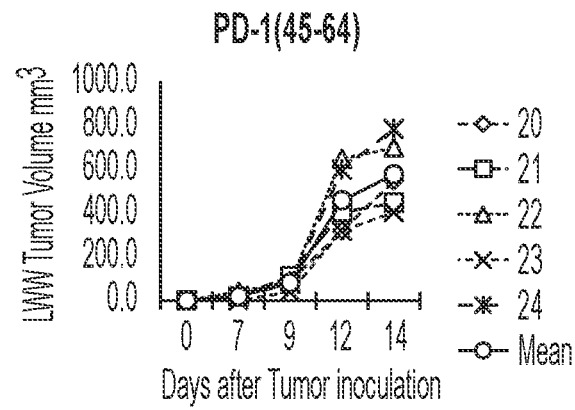
Figure 11C:
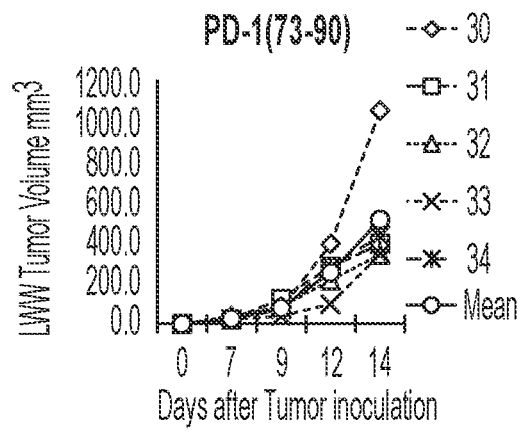
Figure 11D:
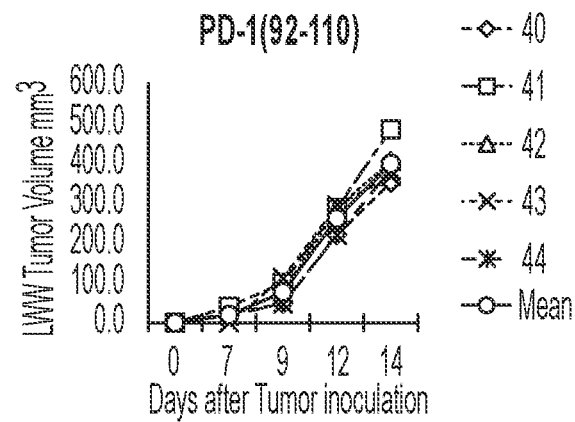
Figure 11E:
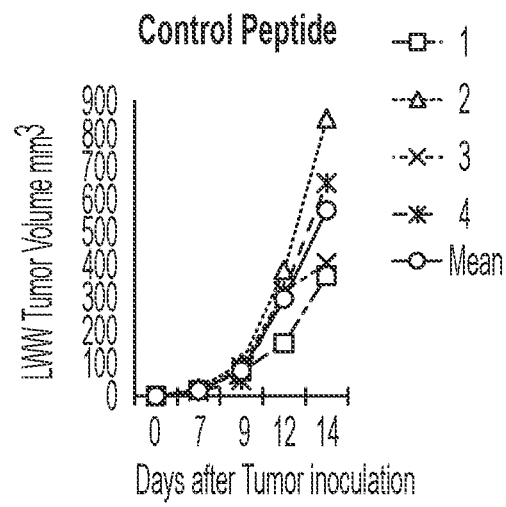
Figure 11F:
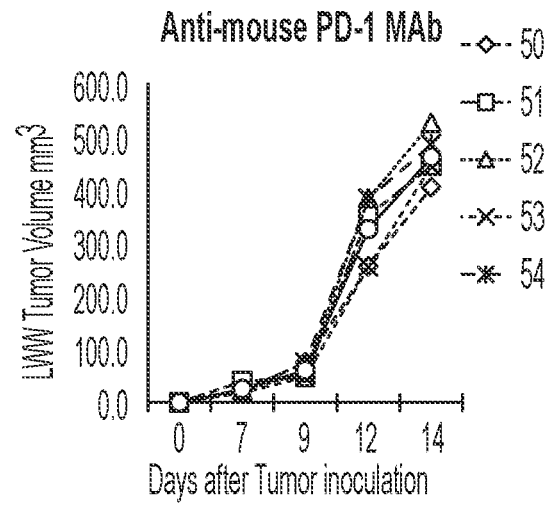
Figure 11G:
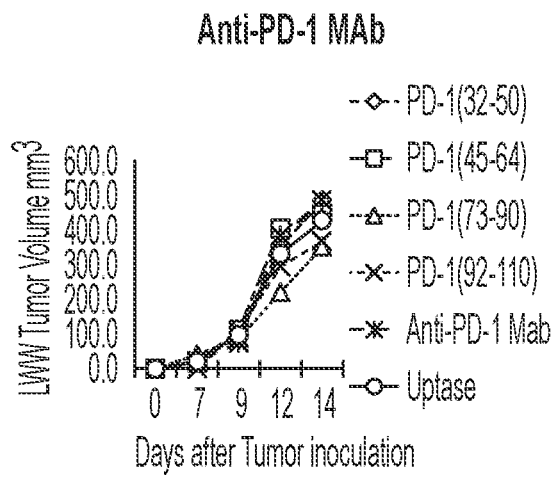
Figure 11H:
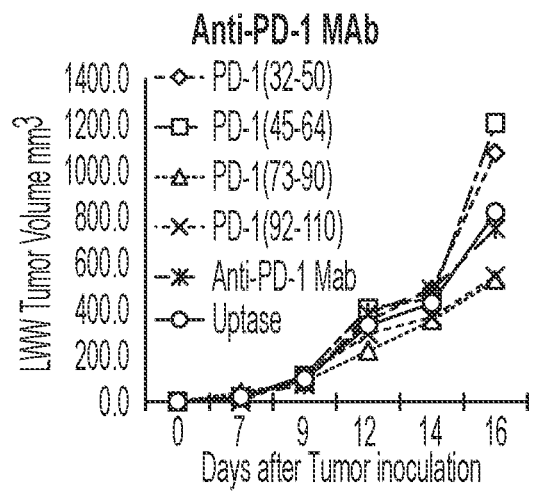

FIGS. 11A, 11B, 11C, 11D, 11E, 11F, 11G, and 11H shows the individual Plots of tumor growth in Balb/c mice (5/group) immunized for each of the four PD-1 constructs A: (PD-1(32-50), B: PD-1 (45-64), C: PD-1 (73-90) and D: PD-1 (92-110), control peptide (E: irrelevant peptide) and a positive control group (F) treated with anti-mouse PD-1 monoclonal antibody. FIGS. 11G and 11H show individual Plots in syngeneic Balb/c immunized with PD-1 vaccine constructs and challenged 10 days after 3rd vaccination with CT26 carcinoma cells ($1\times10^5$). Tumor Mice were monitored and scored for the formation of palpable tumors twice weekly and sacrificed on day 19.

Figure 12A:
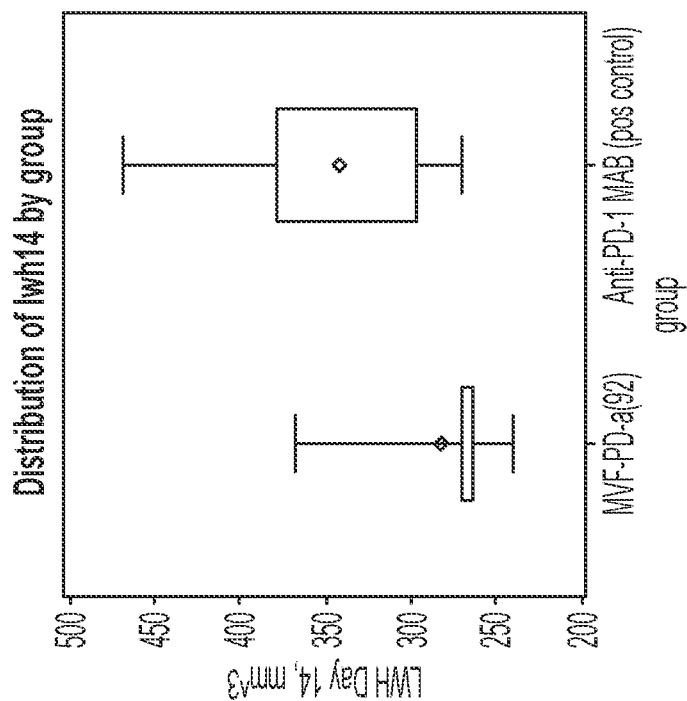
Figure 12B:
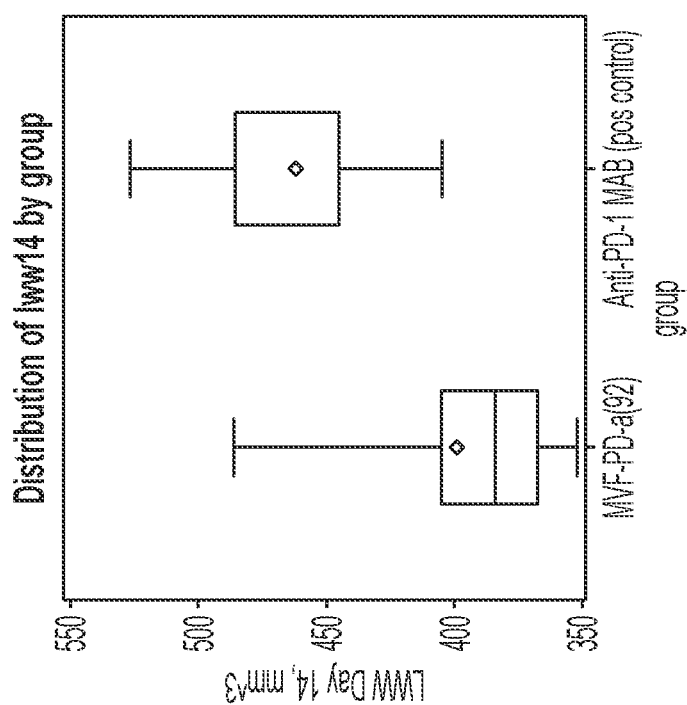
Figure 12C:
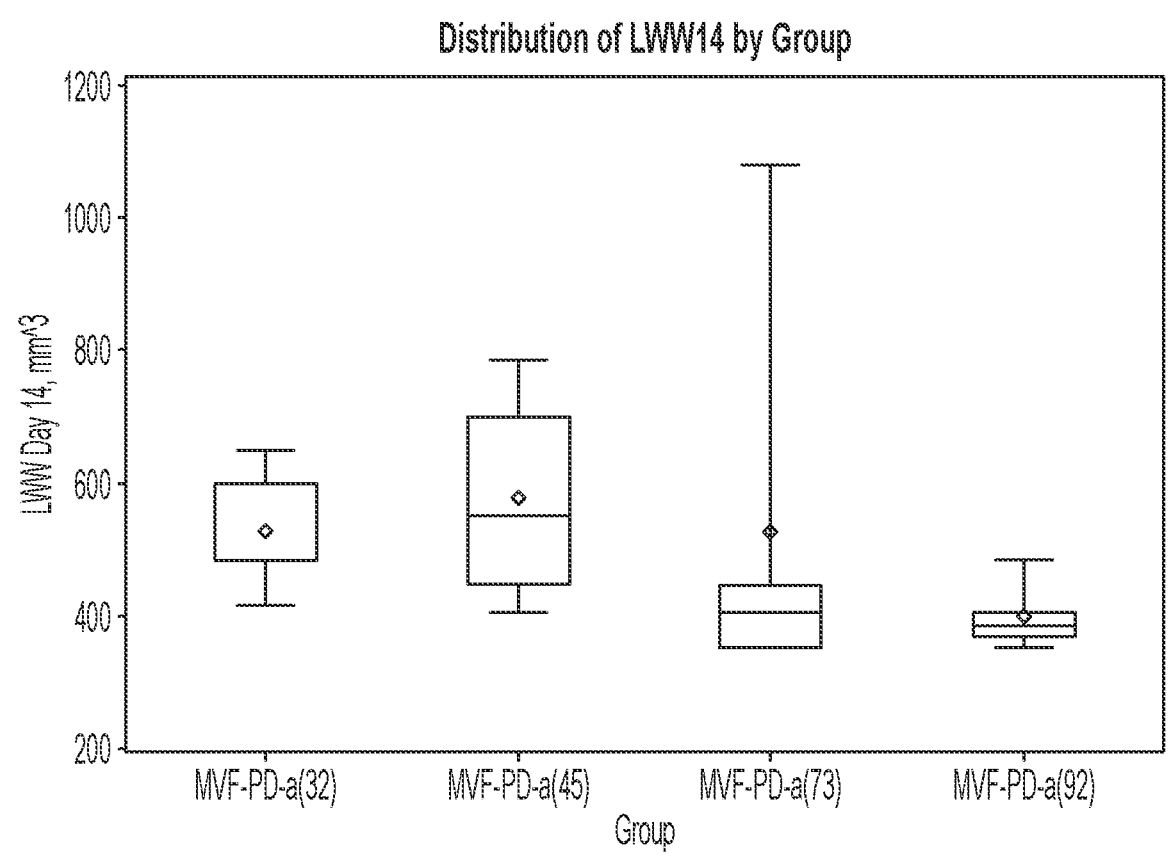
Figure 12D:
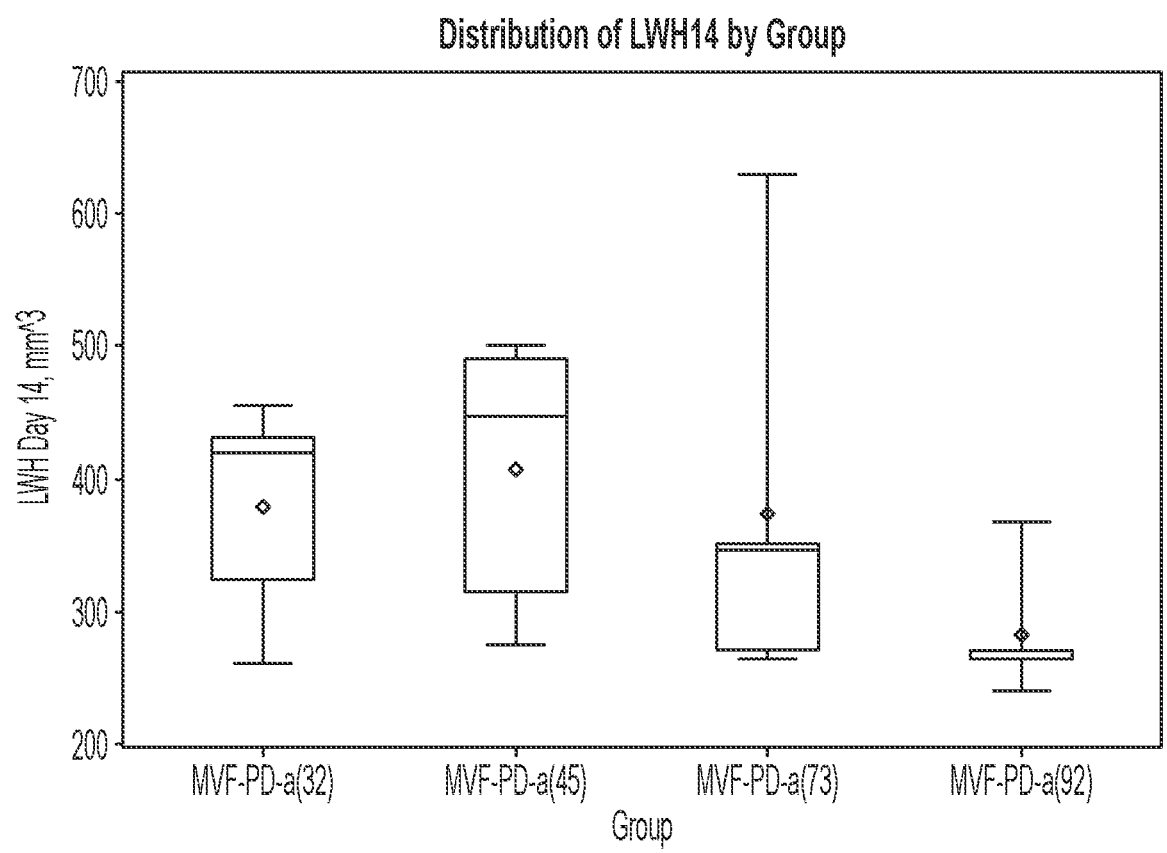

FIGS. 12A, 12B, 12C, and 12D show distribution of LWW and LWH measures at day 14 for MVF-PD-1(32-50), MVF-PD-1(45-64), MVF-PD-1(73-90), and MVF-PD-1 (92-110). LWW (12A) and LWH (12B) for MVF-PD-1(92-110) are shown. FIG. 12C shows distribution of LWW14 by each of MVF-PD-1(32-50), MVF-PD-1(45-64), MVF-PD-1(73-90), and MVF-PD-1(92-110). FIG. 12D shows distribution of LWH14 by each of MVF-PD-1(32-50), MVF-PD-1(45-64), MVF-PD-1(73-90), and MVF-PD-1(92-110).

FIGS. 13A and 13B show αhPD1-45 and αhPD1-73 suppress myelin-specific proliferation. CFSE labeled splenocytes from naïve Vα2.3/Vβ8.2 TCR transgenic mice that are specific for MBP Act-11 were activated with MBP Ac1-11 in the presence of 50 µg/ml of αhPD-1 antibodies or control rabvvit IgG. CFSE was analyzed by flow cytometry (13A). Cells were gated on CD4+ cells. The amount of cells per generation of proliferation was summarized in 13B.

Figure 14:
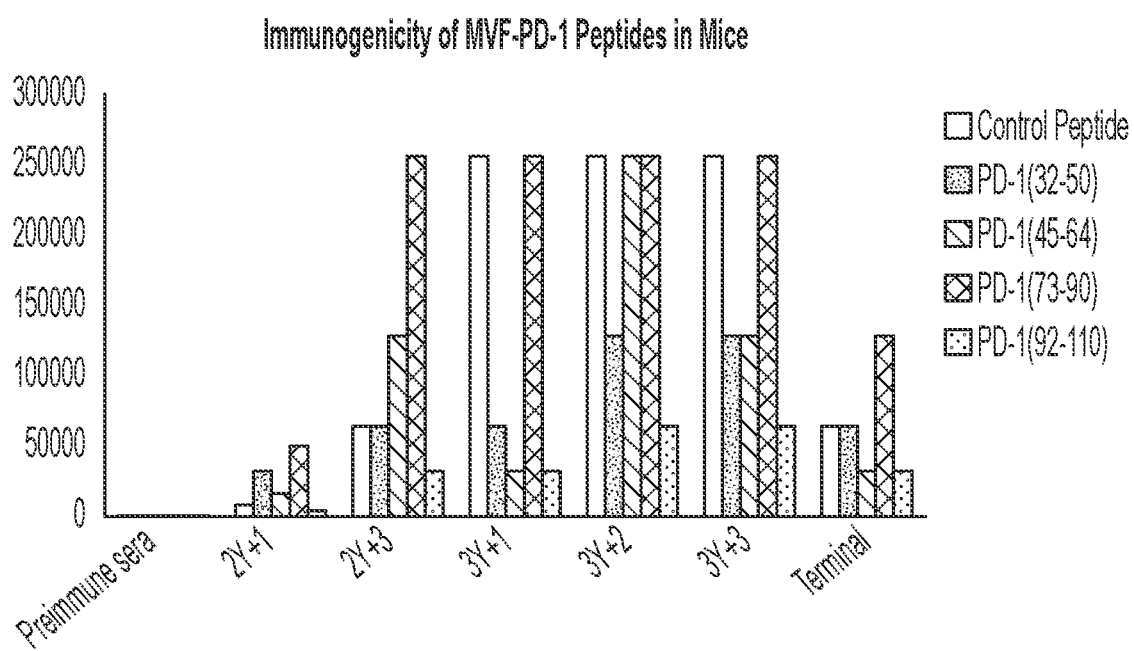

FIG. 14 shows the immunogenicity of PD-1 vaccines. Pooled Sera were tested by ELISA on 200 ng/well of MVF-peptide. Sera concentrations from 1:100-1:250,000 were tested. Titers were defined as the final dilution that still had an absorbance >than 0.200 read at 415λ

Figure 15:
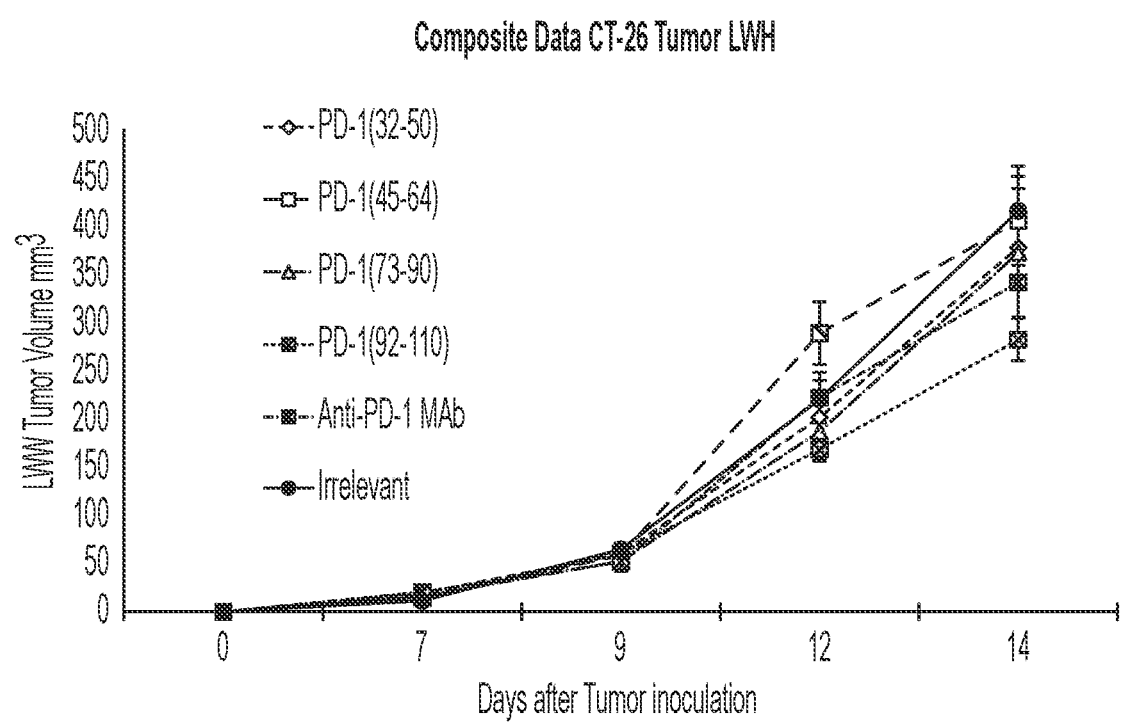

FIG. 15 shows mean plots of tumor growth in syngeneic Balb/c mice (5/gps) immunized with four PD-1 MVF-vaccine constructs A: (PD-1(32-50), B: PD-1 (45-64), C: PD-1 (73-90) and D: PD-1 (92-110), E: −ve control (irrelevant peptide); F: +ve control anti-mouse PD-1 monoclonal antibody (29F.1A12). Mice were challenged 15 days after 3rd vaccination with CT26 carcinoma cells (1×105). Mice were monitored and scored for the formation of palpable tumors, twice weekly tumors were measured using calipers. Animals were sacrificed on day 19.

Figure 16:
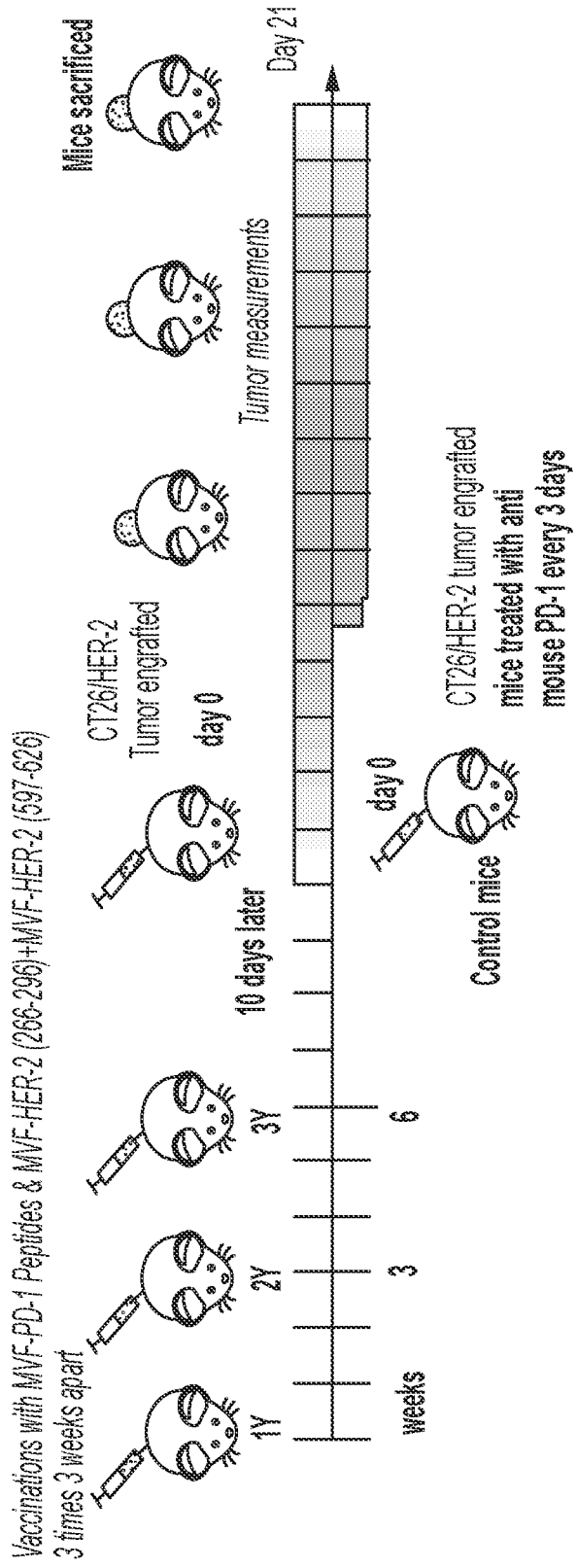

FIG. 16 shows the schedule of combination vaccination in BALB/c followed by challenge with CT26/HER-2 carcinoma cell. The CT-26-HER-2 tumor model in Balb/c was used to test for synergistic effects of anti-PD1 immunization therapy in combination with anti-HER2 immunization therapy. The peptide vaccines were given alone or in combination as noted. Vaccines were dissolved in water and emulsified in Montanide ISA 720 (1:1) and 50 µg nor-MDP (N-acetylglucosamine-3yl-acetyl-1-alanyl-d-isoglutamine). Mice received a total of 3 vaccinations at 3 weeks interval. Female Balb/c mice (Charles River Laboratories) at the age of 5 to 6 wk were immunized three times at 3-wk intervals with 100 µg of each peptide vaccine, and 2 weeks after the third immunization, the mice were challenged subcutaneously (s.c) in the right flank with CT-26-HER-2 neu tumor cells (lx $10^5$ cells/per mouse). Balb/c mice were treated twice a week with anti-mouse PD-1 MAb 29F.1A12 (Bio X Cell, West Lebanon, N.H.) 200 ug/dose was used as a positive control or pbs as a negative control. Mice were monitored and scored for the formation of palpable tumors twice weekly for up to 21 days and sacrificed if tumors became necrotic or exceeded the predetermined size of 2,000 mm3. Tumor volumes were measured in cubic millimeters with calipers and calculated with the following formula: A×B2×0.5, where A is the largest diameter, and B is the smallest diameter.

$$V=[(\text{length}\times\text{width}2)/2].$$

Figure 17:
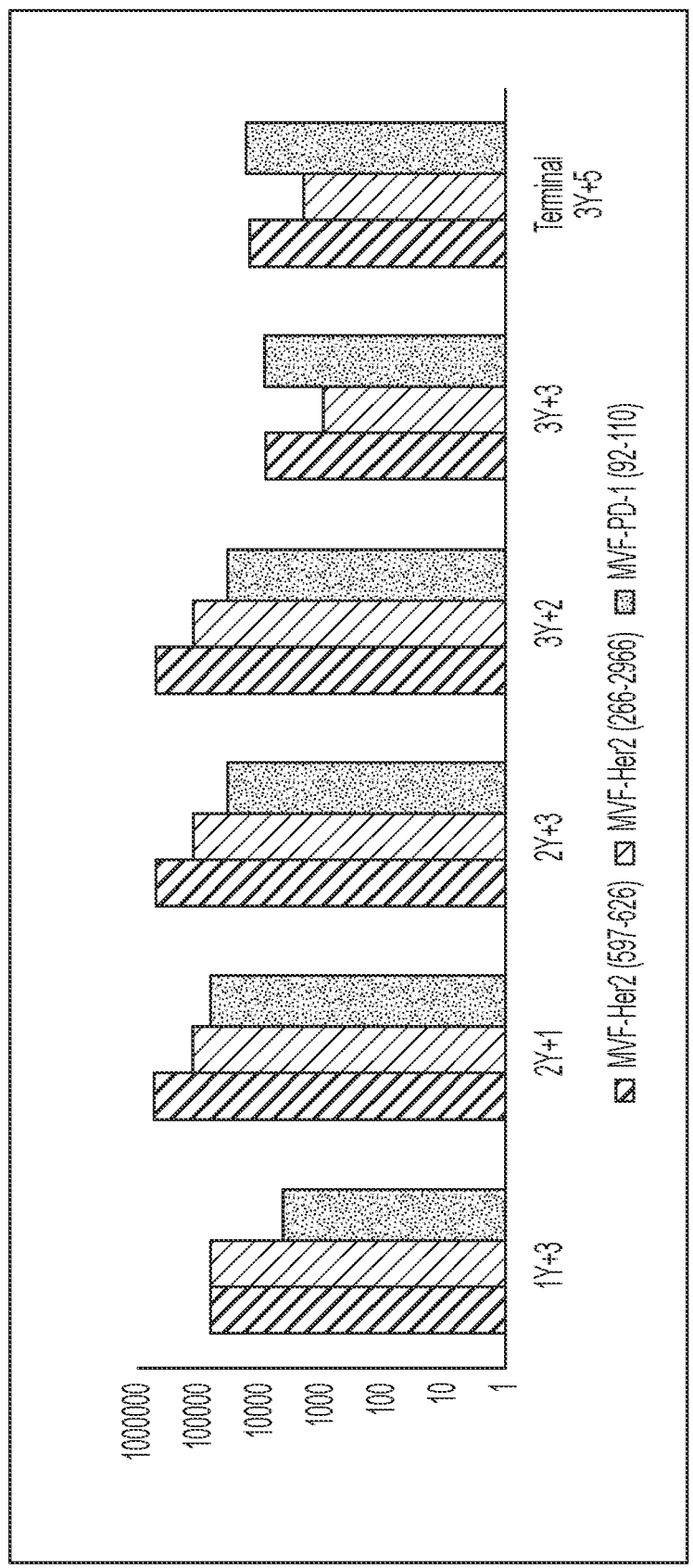

During immunization, blood was drawn biweekly and used in ELISA to monitor Ab titers. The mice were euthanized at the end of treatment and tumors extracted and weighed samples of the tumors were saved for further study and for histological examination. The spleens were also collected for further examination. All experiments were performed in accordance with the U.S. Public Health Service Policy on Humane Care and Use of Laboratory Animals and approved by the Ohio State University Institutional Animals Care and Use Committee and detailed in the accepted protocol FIG. 17 shows the immunogenicity individual antigens in triple vaccine treated mice. Sera pools from mice immunized with 3 peptides (HER-2(266-296), HER-2(597-626), and PD-1(92-110)) were tested by ELISA on 200 ng/well of MVF-peptide. Sera concentrations from 1:100-1:512,000 were tested. ABTS was used as a substrate in the assay the enzyme reaction was stopped after 10 minutes with a 0.1% SDS solution. Titers were defined as the final dilution that still had an absorbance >than 0.200 when read at 415 nm. Sera samples 1Y+3, 2Y+1, 2Y+3, and 3Y+2 were taken before CT-26 HER-2 neu tumor challenge. Samples 3Y+3 and 3Y+5 were taken at 1 week and 3 weeks post challenge respectively.

Figure 18:
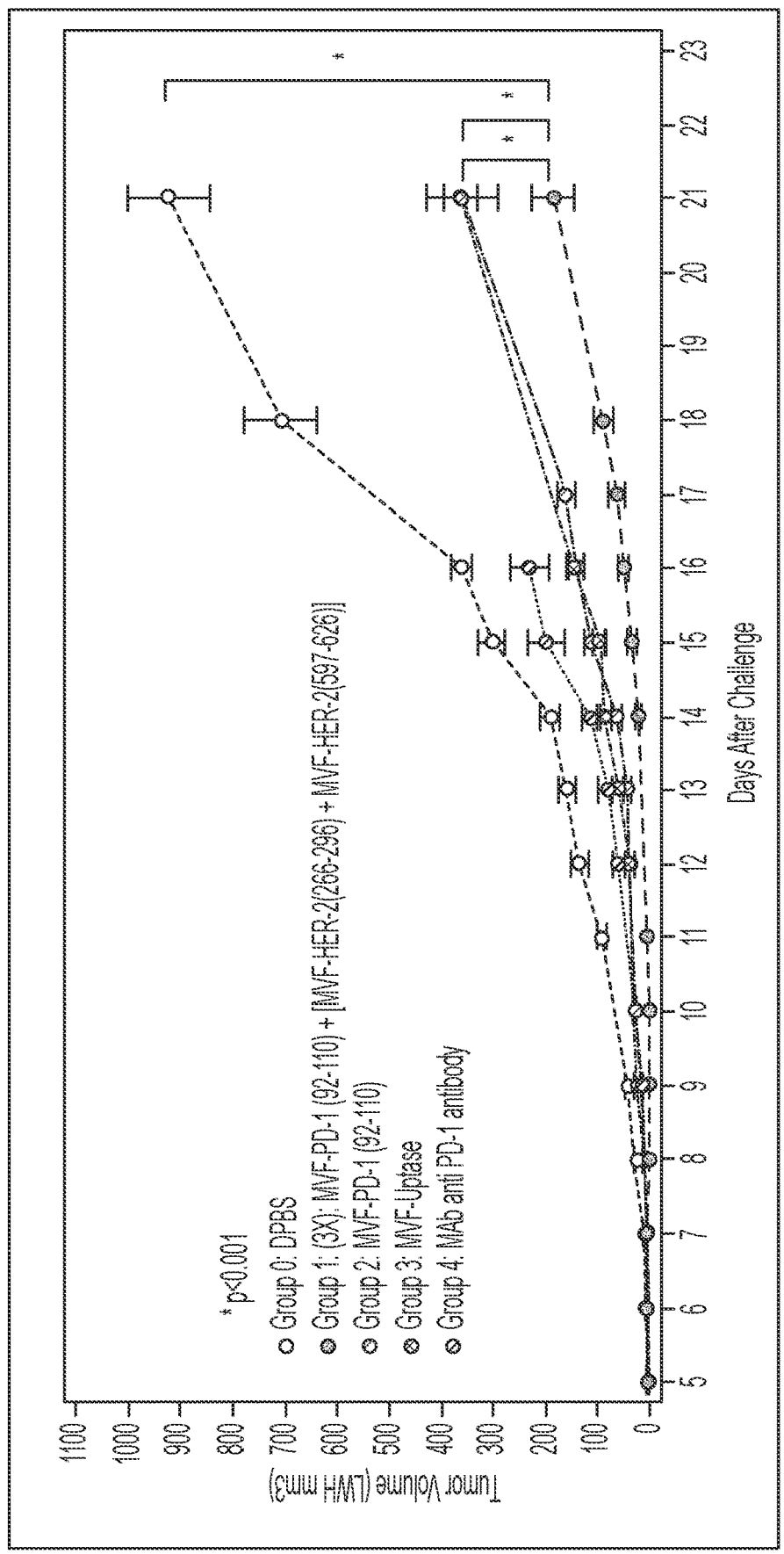

FIG. 18 shows that Triple HER-2 (266)+HER-2(597)+PD-1 (92) vaccination causes significant (p<0.001) inhibition of tumor growth in BALB/c challenged with colon carcinoma cell line CT26/HER-2 compared to positive control α-mouse PD-1 mAb (29F.1A12), MVF-PD-1 (92-110), negative control PBS or irrelevant peptide.

Figure 19A:
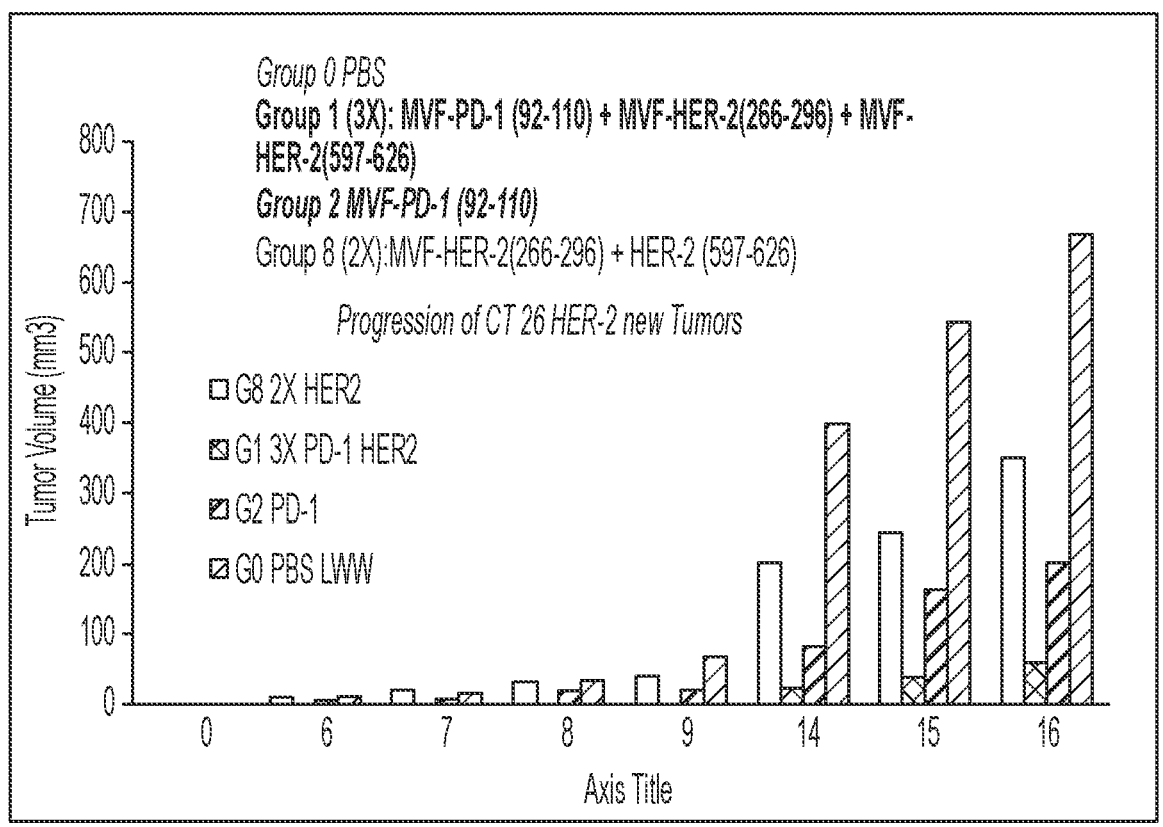
Figure 19B:
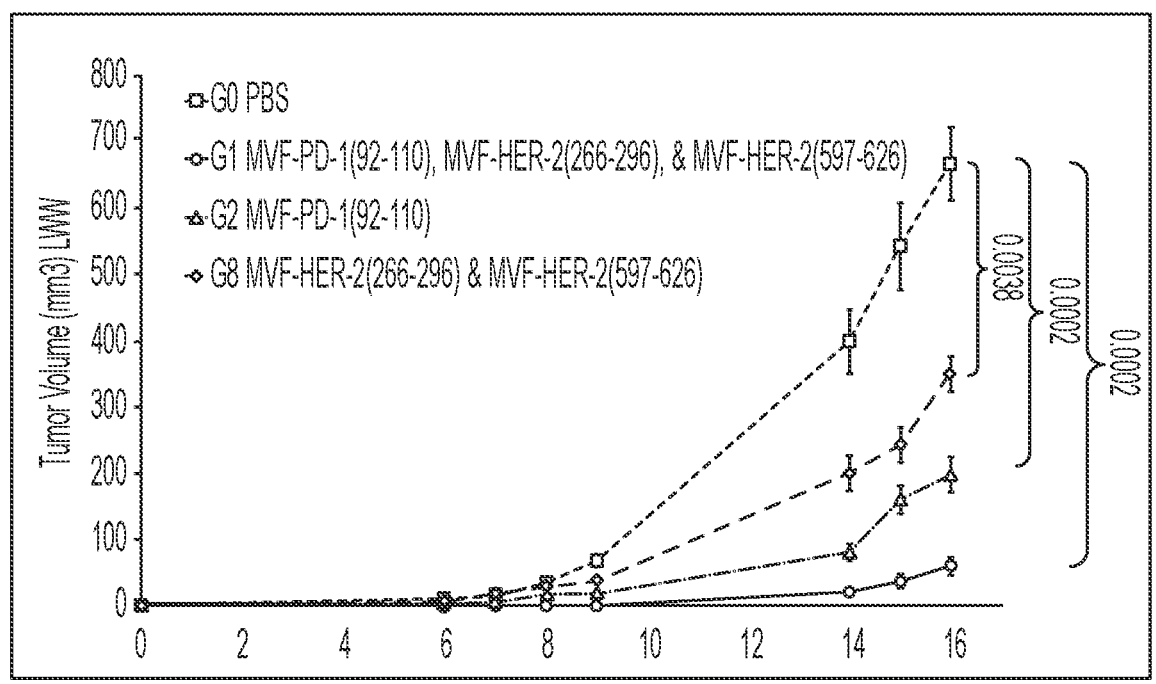

FIGS. 19A and 19B show that the combination HER-2 and PD-1 Vaccines show enhanced immunogenicity and inhibition of tumor growth. Plots of tumor growth in syngeneic Balb/c mice (10/gps) immunized 3 times at 3 week intervals with PD-1 (92-110) alone, in combination with immunization two HER-2 peptide immunogens, or with HER-2 immunogens alone. Mice were challenged 15-18 days after 3rd vaccination with CT-26 HER-2 carcinoma cells ($1\times10^5$). PBS (Negative control) were challenged with tumors and then treated twice a week with IP injections of PBS. Mice were monitored and scored for the formation of palpable tumors, then measured regularly using calipers. Error bars are a representation of Standard Error for the group of mice and p-values compare various groups to Negative control PBS treated mice.

Figure 20A:
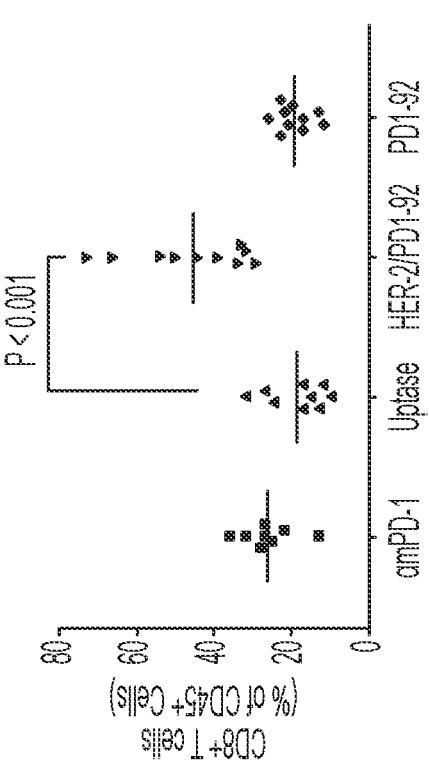
Figure 20B:
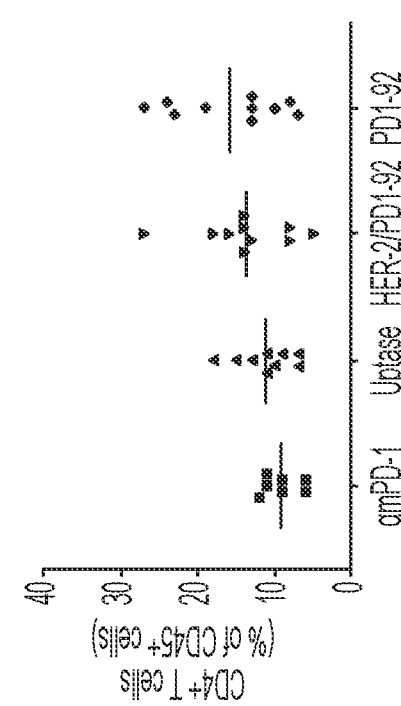
Figure 20C:
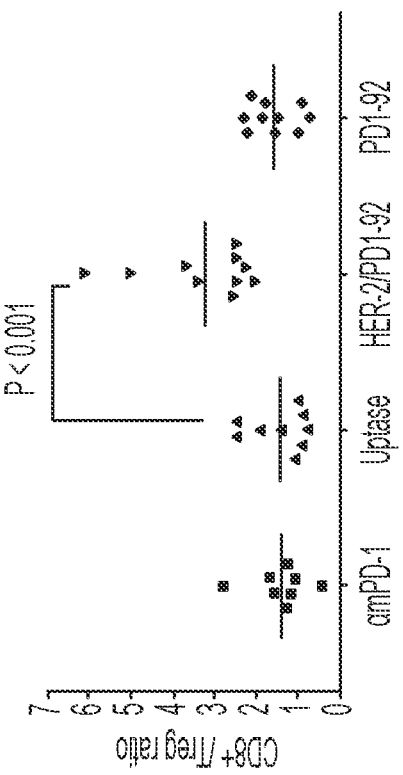
Figure 20D:
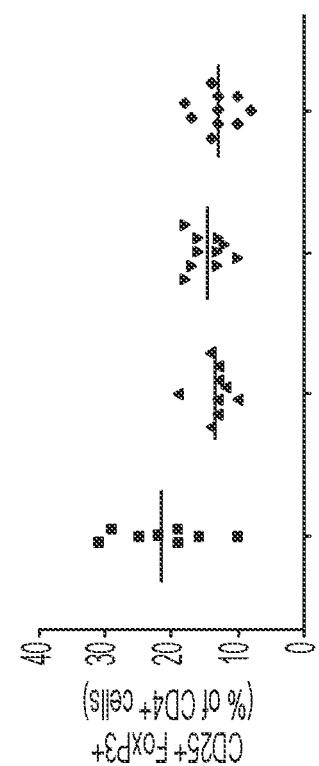
Figure 21A:
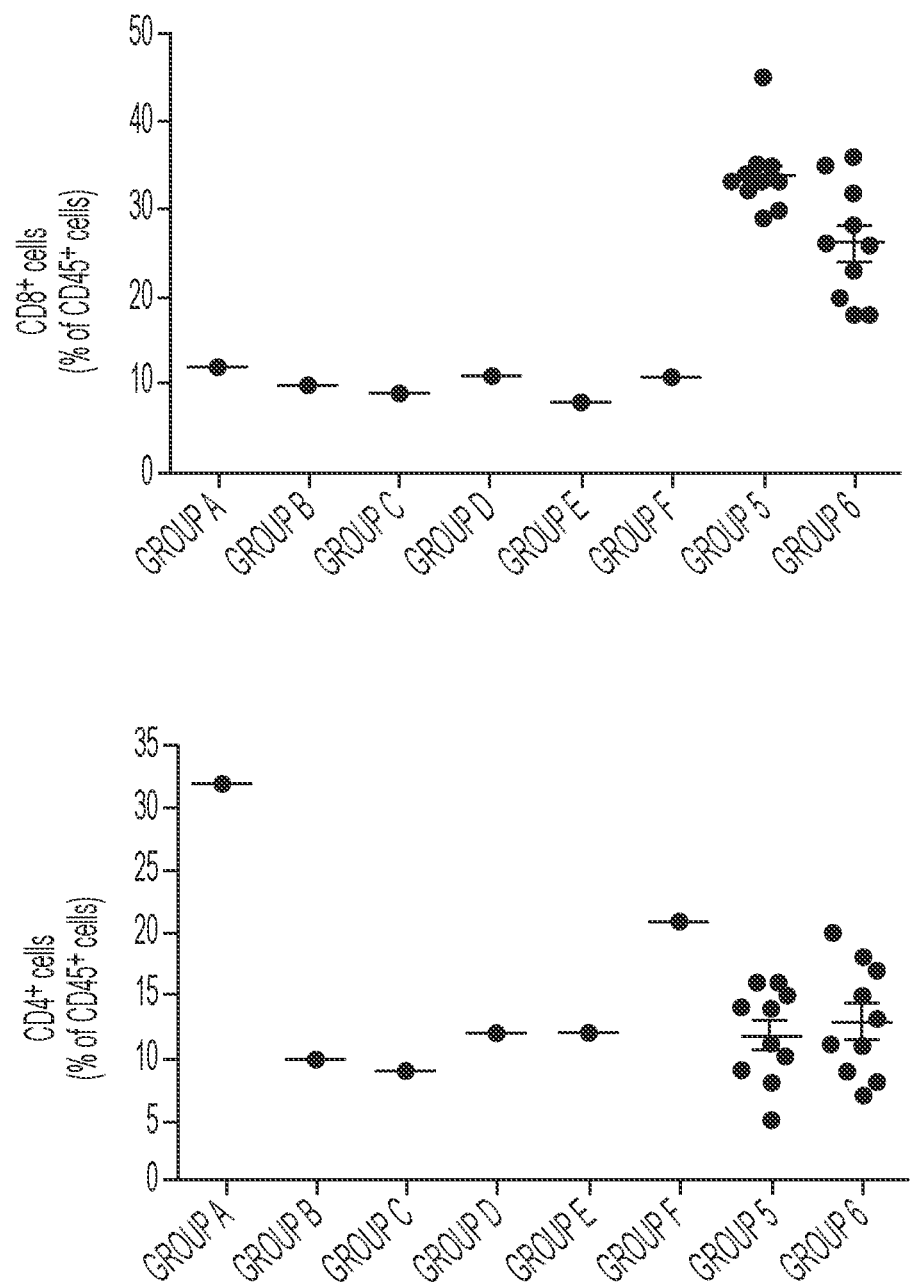
Figure 21A:
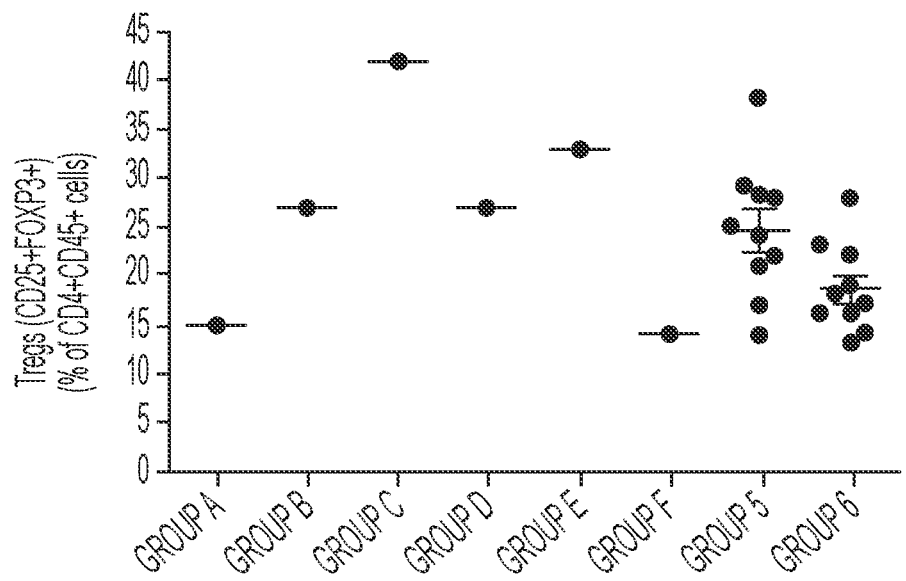
Figure 21B:
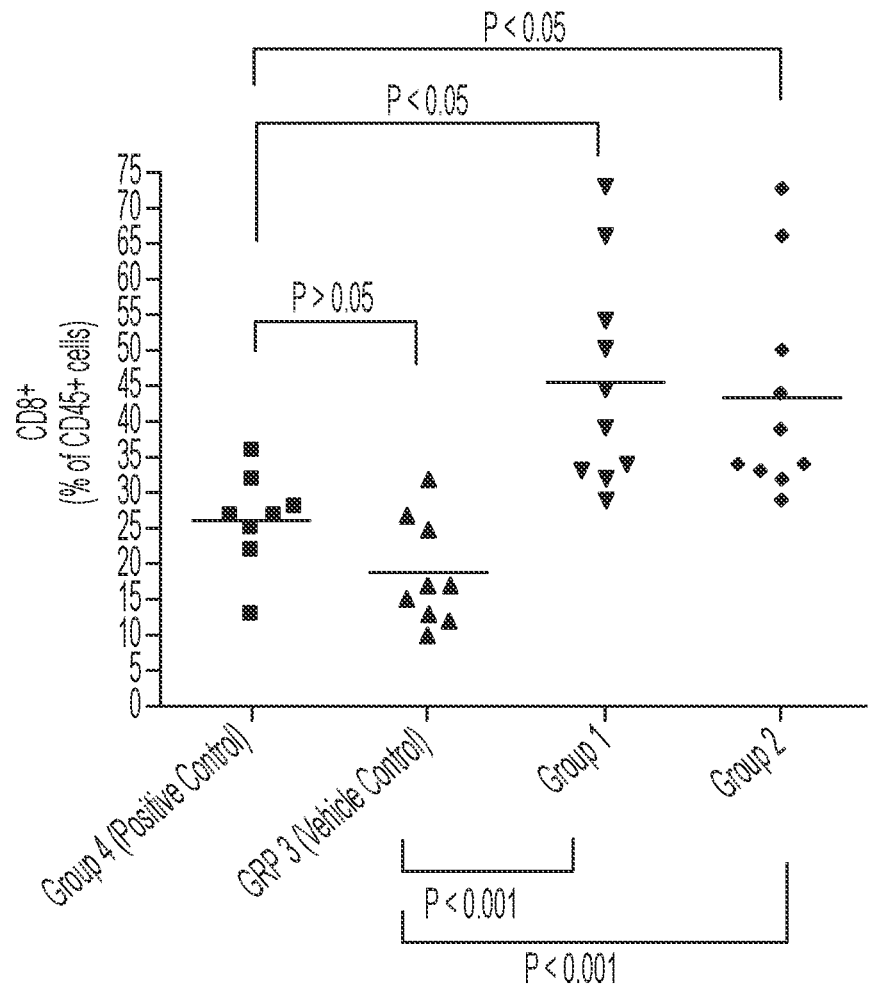
Figure 21B:
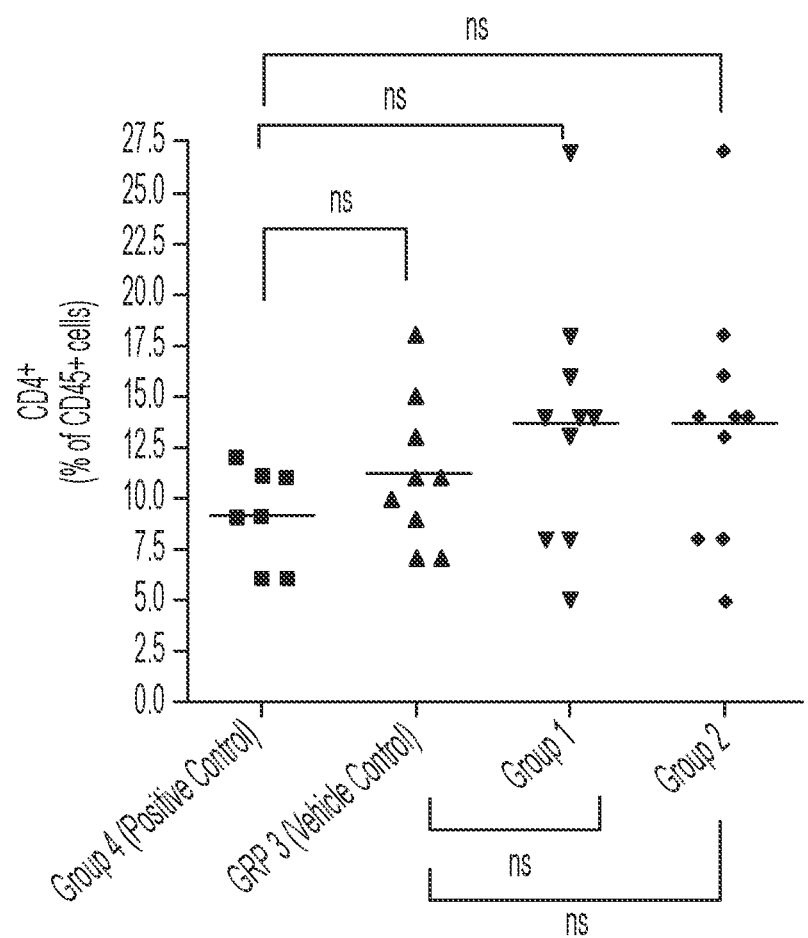
Figure 21B:
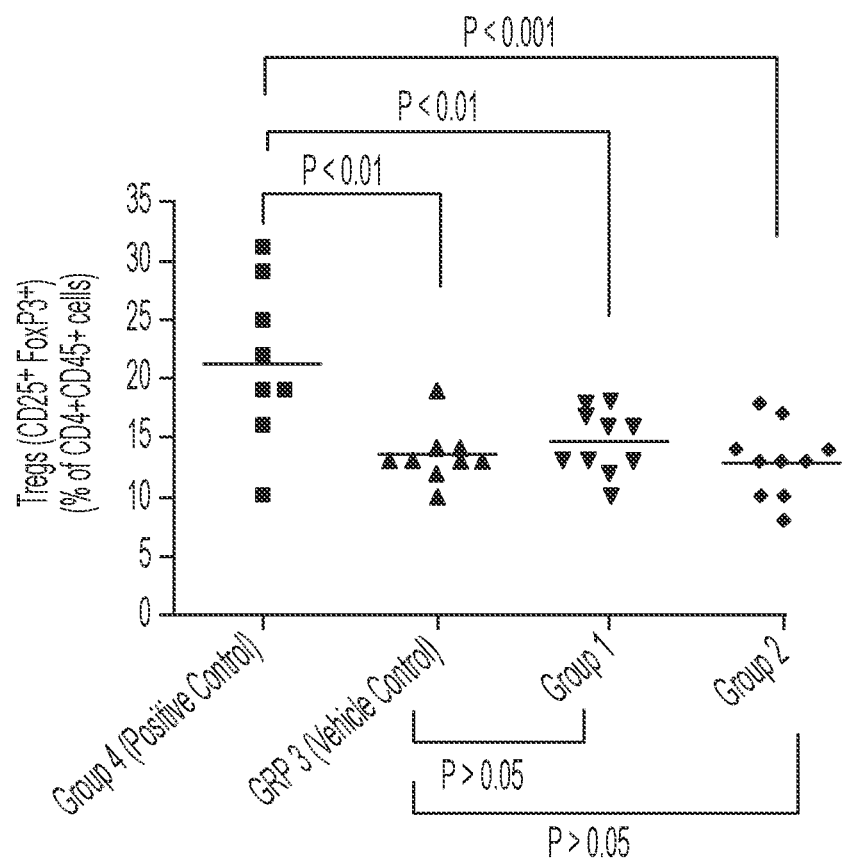

FIGS. 20A, 20B, 20C, and 20D show that TILs were isolated from each mouse in 4 groups. CD4 (20A) and CD8 (20B) T cells were determined by flow cytometry (gated on CD45+ cells). Foxp3+CD25+CD4 Tregs (0 C) were determined by intracellular staining (gated on CD45+CD4+ cells). FIG. 20D shows the ration of $CD8^+$ T cells to T reg. Group means were calculated and compared with Anova FIGS. 21A and 21B show Analysis of tumor infiltrating lymphocytes from peptide-vaccinated mice. FIG. 21A shows combined data from 1st in vivo experiment and group 5 and 6 from 2nd in vivo experiment. Tumor infiltrating cells were isolated from combined tumor tissue from 5 groups (group A to F) of treated mice in first in vivo experiment. Tumor infiltrating cells were isolated from each mouse in group 5 and 6 from second in vivo experiment. CD4 and CD8 cells were determined by flow cytometry (gated on CD45+ infiltrating cells). FoxP3 expression on CD25+ CD4+ T cells were determined by intracellular staining (gated on CD45+CD4+ cells). FIG. 21B shows that tumor infiltrating cells were isolated from each mouse in group 1-4 from second in vivo experiment. CD4 and CD8 cells were determined by flow cytometry (gated on CD45+ infiltrating cells). FoxP3 expression on CD25+CD4+ T cells were determined by intracellular staining (gated on CD45+CD4+ cells). Group means were calculated and compared with Anova. Error bars denote s.e.m.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The term "administering" refers to an administration that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. Embodiments defined by each of these transition terms are within the scope of this invention.

An "effective amount" is an amount sufficient to effect beneficial or desired results. An effective amount can be administered in one or more administrations, applications or dosages.

The terms "treat", "treating", "treatment" and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. In some instances, the terms "treat", "treating", "treatment" and grammatical variations thereof, include partially or completely reducing the size of a tumor, reducing the number of tumors, and reducing the severity/metastatic ability of a tumor as compared with prior to treatment of the subject or as compared with the incidence of such symptom in a general or study population.

The term "inhibit" refers to a decrease in an activity, response, condition, disease, or other biological parameter. This can include but is not limited to the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound. As used herein, a "wt. %" or "weight percent" or "percent by weight" of a component, unless specifically stated to the contrary, refers to the ratio of the weight of the component to the total weight of the composition in which the component is included, expressed as a percentage.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular synthetic or chimeric PD-1 peptide is disclosed and discussed and a number of modifications that can be made to a number of molecules including the synthetic or chimeric PD-1 peptide are discussed, specifically contemplated is each and every combination and permutation of the synthetic or chimeric PD-1 peptide and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The PD-1 gene, which belongs to the immunoglobulin super family, encodes a 55 kDa type I transmembrane protein. Both mouse PD-1 and human PD-1 consist of 288 amino acids, and have signal peptide at N terminal (20 amino acid) and hydrophobic region in the middle part, which is a transmembrane region. Human and murine PD-1 proteins share about 60%-80% amino acid identity with conservation of four potential N-glycosylation sites, and residues that define the Ig-V domain. PD-1 is expressed on T cells, B cells, and macrophages. The ligands for PD-1 are the B7 family members PD-L1 (B7-H1) and PD-L2 (B7-DC). Signaling through the immune checkpoint programmed cell death protein-1 (PD-1) enables tumor progression by dampening antitumor immune responses. Therapeutic blockade of the signaling axis between PD-1 and its ligand programmed cell death ligand-1 (PD-L1) with monoclonal antibodies has shown remarkable clinical success in the treatment of cancer and demonstrated impressive activity across a broad set of cancer subtypes. Disclosed herein, are improvements on traditional PD-1/PD-L1 blockades using smaller, non-antibody peptide therapeutics and peptide vaccines which directly block the interaction of PD-1 and PD-L1 or can stimulate host immune responses to generate antibodies to PD-1 that block the PD-1/PD-L1 interaction.

Using computer aided analysis of PD-1 B cell epitopes, sequences corresponding to PD-1 (SEQ ID NO: 1) residues 32-50, 45-64, 73-90, and 92-110 were derived. Thus, in one aspect, disclosed herein are synthetic PD-1 peptides for stimulating an immune response to a PD-1 protein comprising residues 32-50, 45-64, 73-90 and/or 92-100 of PD-1. For example, disclosed herein are synthetic PD-1 peptides for stimulating an immune response to a PD-1 protein comprising VLNWYRMSPSNQTDKLAAF (SEQ ID NO: 2), KLAAFPEDRSQPGQDCRFR (SEQ ID NO: 3), DFHMSVVRARRNDSGTYL (SEQ ID NO: 4), and/or GAISLAPKAQIKESLRAEL (SEQ ID NO: 5). In one aspect, the peptides can be acylated and/or amidated. Thus, disclosed herein are synthetic PD-1 peptides for stimulating an immune response to a PD-1 protein comprising (SEQ ID NO: 2), (SEQ ID NO: 3), (SEQ ID NO: 4), and/or (SEQ ID NO: 5); wherein the synthetic peptide is acylated and/or amidated.

In some instances uses of an analog of the L-amino sequence can advantages to the base sequence such as resistance to degradation, stability, ease of synthesis, or have greater efficacy. In one aspect, it is understood and herein contemplated that the disclosed synthetic sequences can be comprise the L-amino sequence in reverse order from amino to carboxy end. For example, the retro sequence of SEQ ID NO: 2, SEQ ID NO: 3, SEQ ID NO: 4, and SEQ ID NO: 5, are FAALKDTQNSPSMRYWNLV (SEQ ID NO: 12), RFRCDQGPQSRDEPFAALK (SEQ ID NO: 13), LYTGSDNRRARVVSMHFD (SEQ ID NO: 14), and LEARLSEKIQAKPALSIAG (SEQ ID NO: 15), respectively. These retro sequences can also have the mirror conformation of the base sequence. Thus, disclosed herein are synthetic PD-1 peptides comprising one or more of the sequences as set forth in SEQ ID NO: 12, SEQ ID NO: 13, SEQ ID NO: 14, and/or SEQ ID NO: 15. As with SEQ ID NO: 2, SEQ ID NO: 3, SEQ ID NO: 4, and SEQ ID NO: 5; synthetic peptides comprising SEQ ID NO 12, SEQ ID NO: 13, SEQ ID NO: 14 and/or SEQ ID NO: 15 can be acetylated and/or amidated.

In addition to retro analogs of the L-amino acid sequence set forth in SEQ ID NO: 2, SEQ ID NO: 3, SEQ ID NO: 4, and SEQ ID NO: 5 which are set forth in SEQ ID NO 12, SEQ ID NO: 13, SEQ ID NO: 14 and SEQ ID NO: 15 are D enantiomer analogs of the forward L-amino (SEQ ID NO: 2, SEQ ID NO: 3, SEQ ID NO: 4, and SEQ ID NO: 5) and retro L-amino sequence (SEQ ID NO 12, SEQ ID NO: 13, SEQ ID NO: 14 and SEQ ID NO: 15) which can possess increased resistance to degradation and proteolysis allowing for better oral administration, extended efficacy, and increased ease of synthesis. Accordingly, in one aspect, disclosed herein are synthetic PD-1 peptides comprising one or more of SEQ ID NO: 2, SEQ ID NO: 3, SEQ ID NO: 4, SEQ ID NO: 5, SEQ ID NO 12, SEQ ID NO: 13, SEQ ID NO: 14 and/or SEQ ID NO: 15; wherein the amino acids comprising the sequence are D amino acids.

In one aspect, it is understood and herein contemplated that the disclosed synthetic PD-1 peptides can have increased B cell stimulation by linking the synthetic PD-1 peptides to a helper T (Th) cell epitope that promotes the release of cytokines that assist in bypassing MHC restriction (i.e., a promiscuous Th cell epitope) to form a chimeric PD-1 peptide. For example, disclosed herein, in one aspect are PD-1 chimeric peptides for stimulating an immune response to a PD-1 protein comprising one or more PD-1 B cell epitopes further comprising a T helper (Th) epitope (for example, a measles virus fusion protein peptide such as SEQ ID NO: 6), wherein the one or more PD-1 B cell epitopes consist of a sequence selected from the group consisting of SEQ ID NO:2, SEQ ID NO:3, SEQ ID NO:4, SEQ ID NO:5, SEQ ID NO: 12, SEQ ID NO: 13, SEQ ID NO: 14, and/or SEQ ID NO: 15. It is understood and herein contemplated that the B cell epitope (i.e., the PD-1 synthetic peptide) can comprise D amino acids.

The Th epitope can be from about 14 to about 22, more preferably about 15 to 21, most preferably 16 amino acids in length. Preferably, the Th cell epitope has one of the following amino acid sequences provided in Table 1.

TABLE 1

| Peptide Designation | Sequence | SEQ ID NO: |
|---|---|---|
| MVF | KLLSLIKGVIVHRLEGVE | 6 |
| TT | NSVDDALINSTIYSYFPSV | 20 |
| TT1 | PGINGKAIHLVNNQSSE | 21 |
| P2 | QYIKANSKFIGITEL | 22 |
| P30 | FNNFTVSFWLRVPKVSASHLE | 23 |
| MVF (natural) | LSEIKGVIVHRLEGV | 24 |
| HBV | FFLLTRILTIPQSLN | 25 |
| CSP | TCGVGVRVRSRVNAANKKPE | 26 |

To join the synthetic PD-1 peptide and the Th cell epitope, an amino acid linker can be used. Preferably the linker is a peptide of from about 2 to about 15 amino acids, more preferably from about 2 to about 10 amino acids, most preferably from about 2 to about 6 amino acids in length. The most preferred linker comprises the amino acid sequence Gly-Pro-Ser-Leu (SEQ ID NO: 7). Thus, in one aspect, also disclosed herein are chimeric peptides comprising the synthetic peptide of any preceding aspect, further comprising a Th epitope (for example, a measles virus fusion protein peptide such as SEQ ID NO: 6), and a linker (such as, for example, SEQ ID NO: 7) joining the synthetic PD-1 peptide to the Th epitope. For example, disclosed herein, in one aspect, are chimeric PD-1 peptides for stimulating an immune response to a PD-1 protein comprising one or more PD-1 B cell epitopes, a T helper (Th) epitope (for example, a measles virus fusion protein peptide such as SEQ ID NO: 6), and a linker (such as, for example, SEQ ID NO: 7) joining the PD-1 B cell epitope to the Th epitope; wherein the chimeric PD-1 peptide comprises the amino acid sequence as set forth in (SEQ ID NO: 8)
KLLSLIKGVIVHRLEGVEGPSLVLNWYRMSPSNQTDKLAAF, (SEQ ID NO: 9)
KLLSLIKGVIVHRLEGVEGPSLKLAAFPEDRSQPGQDCRFR, (SEQ ID NO: 10)
KLLSLIKGVIVHRLEGVEGPSLDFHMSVVRARRNDSGTYL, (SEQ ID NO: 11)
KLLSLIKGVIVHRLEGVEGPSLGAISLAPKAQIKESLRAEL, (SEQ ID NO: 16)
KLLSLIKGVIVHRLEGVEGPSLFAALKDTQNSPSMRYWNLV, (SEQ ID NO: 17)
KLLSLIKGVIVHRLEGVEGPSLRFRCDQGPQSRDEPFAALK, (SEQ ID NO: 18)
KLLSLIKGVIVHRLEGVEGPSLLYTGSDNRRARVVSMHFD,
and/or (SEQ ID NO: 19)
KLLSLIKGVIVHRLEGVEGPSLLEARLSEKIQAKPALSIAG.

As with the synthetic peptides, it is understood and herein contemplated that the amino acids of the synthetic PD-1 peptides comprised within the chimeric PD-1 peptides can be a D amino acid analogs of the L-amino acids in the sequence. Accordingly, in one aspect, disclosed herein are chimeric peptides comprising any of the synthetic PD-1 peptides disclosed herein, further comprising a Th epitope (for example, a measles virus fusion protein peptide such as SEQ ID NO: 6), and a linker (such as, for example, SEQ ID NO: 7) joining the synthetic PD-1 peptide to the Th epitope. For example, disclosed herein, in one aspect, are chimeric PD-1 peptides comprising the amino acid sequence as set forth in SEQ ID NO: 8, SEQI DNO: 9, SEQ ID NO: 10, SEQ ID NO: 11, SEQ ID NO: 16, SEQ ID NO: 17, SEQ ID NO: 18, and/or SEQ ID NO: 19; wherein the synthetic PD-1 peptide sequence (i.e., the B cell epitope) comprises D amino acids.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Peptides a) Protein and Peptide Variants

As discussed herein there are numerous variants of the synthetic PD-1 peptides and chimeric PD-1 peptides that are known and herein contemplated. In addition, to the known functional PD-1 strain variants there are derivatives of the synthetic PD-1 peptides and chimeric PD-1 peptides which also function in the dis Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 2 and 3 and are referred to as conservative substitutions.

TABLE 2

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 3

Amino Acid Substitutions
Original Residue Exemplary Conservative
Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 3, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/ identity to specific known sequences. Specifically disclosed are variants of these and other proteins herein disclosed which have at least, 70% or 75% or 80% or 85% or 90% or 95% identity to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that peptide or protein is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 2 and Table 3. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—$CH$=$CH$— (cis and trans), —$COCH_2$—, —$CH(OH)CH_2$—, and —$CHH_2SO$— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., Int J Pept Prot Res 14:177-185 (1979) (—$CH_2NH$—, $CH_2CH_2$—); Spatola et al. *Life Sci* 38:1243-1249 (1986) (—CH $H_2$—S); Hann *J. Chem. Soc Perkin Trans.* I 307-314 (1982) (—CH—CH—, cis and trans); Almquist et al. *J. Med. Chem.* 23:1392-1398 (1980) (—$COCH_2$—); Jennings-White et al. *Tetrahedron Lett* 23:2533 (1982) (—$COCH_2$—); Szelke et al. European Appln, EP 45665 CA (1982): 97:39405 (1982) (—$CH(OH)$ $CH_2$—); Holladay et al. *Tetrahedron. Lett* 24:4401-4404 (1983) (—$C(OH)CH_2$—); and Hruby *Life Sci* 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. In other words, contemplated herein is the inverso (i.e., the D-amino acid substitution) of any disclosed sequence. Cysteine residues can be used to cyclize or attach two or more peptides together. This can be beneficial to constrain peptides into particular conformations. In one aspect, disclosed herein are synthetic PD-1 peptides comprising one or more of the sequences as set forth in SEQ ID NO:2, SEQ ID NO:3, SEQ ID NO:4, or SEQ ID NO:5; wherein the amino acids of the peptide are the D enantiomer.

In one aspect, the disclosed synthetic peptides can be in reverse order such that the amino to carboxy end of the peptide is reversed (i.e., the retro sequence). In one aspect, disclosed herein are the retro sequences of SEQ ID NO: 2, SEQ ID NO: 3, SEQ ID NO: 4, and SEQ ID NO: 5, which comprises, SEQ ID NO: 12, SEQ ID NO: 13, SEQ ID NO: 14, and SEQ ID NO: 15, respectively. These retro sequences can also have the mirror conformation of the base sequence. In one aspect, the retro sequence can also comprise a D amino acid substitution (i.e., the retro-inverso) sequence. Thus, disclosed herein are synthetic PD-1 peptides comprising one or more of the sequences as set forth in SEQ ID NO: 12, SEQ ID NO: 13, SEQ ID NO: 14, and SEQ ID NO: 15; wherein the amino acids of the peptide are the D enantiomer.

It is understood that any of the D amino acid substituted synthetic peptides disclosed herein can be used in as the PD-1 epitope in the disclosed PD-1 chimeric peptides. For example, disclosed herein are chimeric PD-1 peptides comprising one or more PD-1 B cell epitopes, a T helper (Th) epitope, and a linker joining the PD-1 B cell epitope to the Th epitope, wherein the one or more PD-1 B cell epitopes consist of a sequence selected from the group consisting of SEQ ID NO: 2, SEQ ID NO: 3, SEQ ID NO: 4, SEQ ID NO: 12, SEQ ID NO: 13, SEQ ID NO: 14, and SEQ ID NO: 15; and wherein the amino acids of the peptide are the D enantiomer. In one aspect, disclosed herein are chimeric PD-1 peptides, wherein the peptide comprises the amino acid sequence as set forth in SEQ ID NO: 8, SEQI DNO: 9, SEQ ID NO: 10 SEQ ID NO: 11, SEQ ID NO: 16, SEQ ID NO: 17, SEQ ID NO: 18, or SEQ ID NO: 19; and wherein the amino acids of the synthetic PD-1 peptide are the D enantiomer.

3. Pharmaceutical Carriers/Delivery of Pharmaceutical Products

As described above, the synthetic PD-1 peptides and chimeric PD-1 peptides disclosed herein can also be administered in vivo in a pharmaceutically acceptable carrier. Thus, in one aspect, disclosed herein are pharmaceutical composition comprising any one or more of the PD-1 peptides as set forth in SEQ ID NO: 2, SEQID NO: 3, SEQ ID NO: 4, SEQID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and/or SEQ ID NO: 19.

By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

It is understood and herein contemplated that the disclosed PD-1 peptides comprising pharmaceutical compositions are particularly useful in the treatment of diseases or conditions where PD-1 mediated immune suppression occurs. Thus, in one aspect, the disclosed pharmaceutical composition comprising one or more of the PD-1 peptides disclosed herein can be combined with a disease-specific treatment or vaccine to further increase the efficacy of the PD-1 peptides. For example, a pharmaceutical composition comprising one or more of the PD-1 peptides can be combined with anti-HER2 antibodies or HER-2 B cell epitopes for use in treating, inhibiting, and/or preventing breast cancer. Accordingly, in one aspect, disclosed herein are pharmaceutical compositions comprising one or more of the PD-1 peptide, synthetic peptides, or chimeric peptides disclosed herein (for example, SEQ ID NO: 2, SEQID NO: 3, SEQ ID NO: 4, SEQID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and/or SEQ ID NO: 19) further comprising one or more HER-2 B cell epitopes (for example SEQ ID NO: 27 or 29 or chimeric epitopes SEQ ID NO: 28 or 30) and/or anti-Her-2 antibodies. In one aspect, specifically disclosed herein are pharmaceutic compositions comprising MVF-PD1 (92-110) as set forth in SEQ ID NO: 11; a MVF-HER-2 (266-296) peptide (for example as set forth in SEQ ID NO: 28), and a MVF-HER-2 (597-626) peptide (for example as set forth in SEQ ID NO: 30).

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

Molecular and cellular mechanisms of receptor-mediated endocytosis has been reviewed (Brown and Greene, DNA and Cell Biology 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

The synthetic PD-1 peptides, chimeras, and antibodies disclosed herein that inhibit the interaction of PD-1 and PD-L1 can be administered prophylactically to patients or subjects who are at risk for developing a cancer, autoimmune disease, of Alzheimer's disease or therapeutically (i.e., after diagnosis of a disease or onset of symptoms) for treatment of a cancer, autoimmune disease, of Alzheimer's disease.

Other molecules or antibodies that interact with PD-1 or PD-L1 to inhibit PD-1/PD-L1 interactions (for example, Pembrolixumab and nivolumab) can be used in combination with the disclosed synthetic PD-1 peptides, chimeric PD-1 peptides, or anti-PD-1 antibodies to treat a cancer, autoimmune disease or Alzheimer's disease in a subject.

4. Antibodies 1

(1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with PD-1 such that PD-1 is inhibited from interacting with PD-L1. Antibodies that bind SEQ ID NO: 1, SEQ ID NO: 2, SEQID NO: 3, SEQ ID NO: 4, SEQID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and/or SEQ ID NO: 19 involved in the interaction between PD-1 and PD-L1 are also disclosed. The antibodies can be tested for their desired activity using the in vitro assays described herein, or by analogous methods, after which their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces mono clonal antibodies. For example, disclosed monoclonal antibodies can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or fragments thereof" encompasses chimeric antibodies and hybrid antibodies, with dual or multiple antigen or epitope specificities, and fragments, such as F(ab')2, Fab', Fab, Fv, sFv, and the like, including hybrid fragments. Thus, fragments of the antibodies that retain the ability to bind their specific antigens are provided. For example, fragments of antibodies which maintain PD-1 binding activity or bind SEQ ID NO: 1, SEQ ID NO: 2, SEQID NO: 3, SEQ ID NO: 4, SEQID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and/or SEQ ID NO: 19 are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual*. Cold Spring Harbor Publications, New York, (1988)).

Also included within the meaning of "antibody or fragments thereof" are conjugates of antibody fragments and antigen binding proteins (single chain antibodies).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The disclosed human antibodies can be prepared using any technique. The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad.*

Sci. USA, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an sFv, Fv, Fab, Fab', F(ab')2, or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody.

(4) Administration of Antibodies

Administration of the antibodies can be done as disclosed herein. Nucleic acid approaches for antibody delivery also exist. The broadly neutralizing anti-PD1 antibodies and antibody fragments (including any antibody that binds to SEQ ID NO: 1, SEQ ID NO: 2, SEQID NO: 3, SEQ ID NO: 4, SEQID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and/or SEQ ID NO: 19) can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

C. METHOD OF TREATING DISEASE

It is understood and herein contemplated that the disclosed compositions, synthetic PD-1 peptides, and chimeric PD-1 peptides can be used to treat any disease where immune suppression and prevention of programmed cell death is advantageous to the disease, such as Alzheimer's disease, autoimmune diseases, or any disease where uncontrolled cellular proliferation occurs such as cancers.

A non-limiting list of different types of autoimmune disease that can be treated using the chimeric or synthetic peptides or pharmaceutical compositions disclosed herein includes, but is not limited to, Psoriasis, Alopecia Areata, Primary biliary cirrhosis, Autoimmune polyendocrine syndrome, Diabetes mellitus type 1, autoimmune thyroiditis, Systemic Lupus Erythematosus, Multiple sclerosis, Guillain-Barré syndrome, Grave's disease, Sjogren's syndrome, ulcerative colitis, Autoimmune hemolytic anemia, Pernicious anemia, Psoriatic arthritis, rheumatoid arthritis, relapsing polychondritis, myasthenia gravis, Acute disseminated encephalomyelitis, and Granulomatosis with polyangiitis.

A non-limiting list of different types of cancers that can be treated using the chimeric or synthetic peptides or pharmaceutical compositions disclosed herein includes, but is not limited to, lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions, chimeric peptides, and synthetic peptides can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, ipilimumab-refractory melanoma, or pancreatic cancer.

Accordingly, in one aspect, disclosed herein are methods of treating a cancer, Alzheimer's disease, or an autoimmune disease in a subject comprising administering to a subject a PD-1 synthetic peptide, wherein the PD-1 synthetic peptide comprises one or more of the sequences as set forth in SEQ ID NO:2, SEQ ID NO:3, SEQ ID NO:4, SEQ ID NO:5, SEQ ID NO: 12, SEQ ID NO: 13, SEQ ID NO: 14, or SEQ ID NO: 15. It is understood and herein contemplated that the synthetic peptides can comprise be acetylated, amidated, and/or the D enantiomer. Accordingly, in one aspect, disclosed herein are methods of treating a cancer, Alzheimer's disease, or an autoimmune disease in a subject comprising administering to a subject a PD-1 synthetic peptide wherein the PD-1 synthetic peptide comprises the D enantiomer and or D enantiomer retro inverso of SEQ ID NO: 2, SEQ ID NO: 3, SEQ ID NO: 4, SEQ ID NO: 5, SEQ ID NO: 18, SEQ ID NO: 9, SEQ ID NO: 10, or SEQ ID NO: 11 as set forth in SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19, respectively.

In one aspect, it is understood that the disclosed compositions can be combined with other treatments for a given disease or condition. For example, in one aspect, disclosed herein are methods of treating a cancer comprising administering to a subject a PD-1 peptide, PD-1 synthetic peptide, or PD-1 chimeric peptide; wherein the disease or condition is breast cancer, and wherein the method further comprises administering to the subject one or more HER-2 B cell epitopes (for example, one or more of the HER-2 peptides as set forth in SEQ ID NO: 27 or 29 or chimeric MVF-HER-2 peptides as set forth in SEQ ID NO: 28 or 30) and/or one or more anti-HER-2 antibodies. It is understood that where a HER-2 B cell epitope or anti-HER-2 antibody is administered to the subject, the administration can be as a separate concurrent administration, prior administration of the HER-2 B cell epitope or anti-HER-2 antibody, subsequent administration of the HER-2 B cell epitope or anti-HER-2 antibody, or a HER-2 B cell epitope or anti-HER-2 antibody that is a component in the same pharmaceutical formulation as the PD-1 peptide, PD-1 synthetic peptide, or PD-1 chimeric peptide. For example, a method of treating breast cancer can comprise administering to a subject a pharmaceutical composition comprising one or more of the PD-1 peptides set forth in SEQ ID NO: 2, SEQ ID NO: 3, SEQ ID NO: 4, and SEQ ID NO: 5; chimeric PD-1 peptides as set forth in SEQ ID NO: 8, SEQ ID NO: 9, SEQ ID NO: 10 and SEQ ID NO: 11; and/or retro inverso PD-1 peptide as set forth in SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19; the method further comprising administering to the subject one or more HER-2 B cell epitopes HER-2(266-296) as set forth in SEQ ID NO: 27 and/or HER-2 (597-626) as set forth in SEQ ID NO: 29 and/or chimeric epitopes MVF-HER-2 (266-296) peptide (for example as set forth in SEQ ID NO: 28, and a MVF-HER-2 (597-626) peptide (for example as set forth in SEQ ID NO: 30). Accordingly, in one aspect, disclosed herein is a method of treating breast cancer comprising administering to a subject with a breast cancer a pharmaceutical composition comprising an MVF-PD1 (92-110) as set forth in SEQ ID NO: 11; a MVF-HER-2 (266-296) peptide (for example as set forth in SEQ ID NO: 28), and a MVF-HER-2 (597-626) peptide (for example as set forth in SEQ ID NO: 30).

It is further understood and herein contemplated that the synthetic peptides for use in treating a cancer, autoimmune disease or Alzheimer's disease can be a component of a chimeric peptide. Thus, in one aspect, disclosed herein are methods of treating a cancer, Alzheimer's disease, or an autoimmune disease in a subject comprising administering to a subject a PD-1 chimeric peptide wherein the chimeric peptide comprises one or more PD-1 B cell epitopes, a T helper (Th) epitope, and a linker joining the PD-1 B cell epitope to the Th epitope, wherein the one or more PD-1 B cell epitopes consist of a sequence selected from the group consisting of SEQ ID NO:2, SEQ ID NO:3, SEQ ID NO:4, SEQ ID NO:5, SEQ ID NO: 12, SEQ ID NO: 13, SEQ ID NO: 14, and SEQ ID NO: 15. It is understood and herein contemplated that the synthetic PD-1 peptides (i.e., the PD-1 B cell epitopes) used in the chimeric peptides can comprise be acetylated, amidated, and/or the D enantiomer. In one aspect, for example, disclosed herein are methods of treating a cancer, Alzheimer's disease, or an autoimmune disease in a subject comprising administering to a subject a PD-1 chimeric peptide wherein the chimeric peptide comprises SEQ ID NO: 8, SEQ ID NO: 9, SEQ ID NO: 10, SEQ ID NO: 11, SEQ ID NO: 16, SEQ ID NO: 17, SEQ ID NO: 18, or SEQ ID NO: 19.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Selection, Design, and Modeling of Peptide Epitopes for PD-1

The selection of candidate B-cell epitopes expressed on the surface of PD-1 was accomplished by an in-house (Peptide Companion™, 5x.com) computer-aided analysis using six correlates of antigenicity reviewed by Kaumaya et al: (a) The profiles of chain flexibility and mobility of individual sequences were calculated according to Karplus and Schultz; (b) Hydropathy profiles were generated over a seven residue span setting and then smoothed with a three-residue span using the scale of Kyte and Doolittle; (c) Hydrophilicity profiles over a six-residue window were generated using the program of Hopp and Woods; (d) Analysis of the exposure of an amino acid residue to water (1.4 Å probe) was carried out by the solvent exposure algorithm of Rose et al.; (e) Protrusion indices were calculated by the method of Thornton et al. that predicts portions of proteins that are accessible and protrude into the solvent; (f) The probability that a five-residue sequence is antigenic was determined by the method of Welling et al.; Sequences were given a score of 1 to 6 based on their respective index values and were ranked: the highest ranking sequences had the highest individual score for the analyses examined (6/6), and successive candidates had the next highest score (5/6), etc. The best scoring epitopes were further ranked by correlation with their secondary structural attributes; e.g., an amphiphilic α-helical sequence or a β-turn loop regions are preferred over a random coil fragments. Computer programs by Chou and Fasman and Novotny et al. were used to predict the secondary structure (α-helix, β-strand/sheet, (3-turn/loop, random coil) and α-helical amphiphilic moment. Finally, consideration was given to the individual amino acid sequence. Electrostatic ion pairs and helix dipole interaction in helical segment were also considered (e.g., hydrophobic/hydrophilic balance). The sequences receiving the highest scores are displayed in Table 4. Employing this method, four of the twelve highest scoring B-cell epitope sequences of human PD-1 were prioritized. Amino acid 32-50, 45-64, 73-90 and 92-110 were chosen for evaluation in combination with information from the crystal structure of PD-1:PDL1 (20). The structures of human PD-1 (PDB 3RRQ) and human PD-L1 (PDB 3BIS, 3FN3, 4Z18, 5C3T) have been determined, but those in turn did not account for significant plasticity within the human PD-1 upon complex formation demonstrated only very recently by the structure of the fully human PD-1/PD-L1 complex (20). Although the above structures provided a complete description of the interaction, the flat surface of the protein-protein interface still complicates drug design efforts in the absence of structural information on the small-molecule inhibitors in complex with either PD-1 or PD-L1 to guide further rational drug development. The crystal structure demonstrates that the receptor-ligand interaction is mediated in its major part by residues of C0CFG strands within both PD-1 and PDL1 (FIG. 1). The protein-protein contacts involve both hydrophobic interactions and polar interactions, and bury a total surface area of 1,970 Å₂. The interaction is constructed around a central hydrophobic core contributed by both partners and constituted by nonpolar residues in the front sheet of PD-1 (Val64, Ile126, Leu128, Ala132, Ile134) and those of the front sheet of PD-L1 (LIle54, LTyr56, LMet115, LAla121, LTyr123), including a characteristic alkyl-p interaction of the side chains of Ile134 and LTyr123. This hydrophobic region is open to the solvent on the would-be antigen-binding site, and is neighbored by a buried region of mixed polar/nonpolar interactions on the opposite side of the molecule. Both these regions are surrounded by a peripheral network of polar residues (safe on the CDR loop side) providing additional hydrogen bond-mediated interactions between the receptor and the ligand. The structure shows that hPD-1, comprising residues 16-127 of the mature polypeptide, consists of a two-layer sandwich with the topology of IgSF domains (i.e. two β sheets (GFCC and ABED) stabilized by a disulfide bond (Cys34-Cys103). FIGS. 2A, 2B, and 2C show modeling of the PD-1 Peptides as conformation epitopes.

TABLE 4 human PD-1 predicted B-cell epitopes

| Residue | Sequence | Secondary Structure |
|---|---|---|
| 32-50 | VLNWYRMSPSNQTDKLAAF (SEQ ID NO: 2) | Anti-parallel β-sheet/loop |
| 45-64 | KLAAFPEDRSQPGQDCRFR (SEQ ID NO: 3) | |
| 73-90 | DFHMSVVRARRNDSGTYL (SEQ ID NO: 4) | |
| 92-110 | GAISLAPKAQIKESLRAEL (SEQ ID NO: 5) | |

FIGS. 2A, 2B, and 2C show modeling of the PD-1 Peptides as conformation epitopes.

2. Example 2: Synthesis, Purification, and Characterization of PD-1 Peptides and MVF-PD-1 Peptides Peptide synthesis was performed using 9600 Milligen/Biosearch solid-phase peptide synthesizer (Millipore, Bedford, Mass.) using Fmoc/Boc chemistry. Clear amide resin (0.50 mmol/gm) (Peptide International, Louisville, Ky.) and Fmoc protected amino acids (P3BioSystems, Louisville, Ky.) were used for synthesis of all of the peptides. In the case of the chimeric peptides, the B cell epitopes were colinearly synthesized with the promiscuous Th MVF (residues 288-302) epitope using regioselective side chain protections and a GPSL linker. Some of the B cell epitopes were acetylated using Acetylimidazole (Sigma-Aldrich St. Louis, Mo.) in DMF. The peptides were reacted overnight then washed with DMF before cleavage. Peptides were cleaved using reagent R (trifluoroacetic acid:TFA:Thiansole:EDT:Anisole, 90:5:3:2)(Sigma-Aldrich, St. Louis, Mo.). The crude peptides were purified by reverse-phase HPLC in a gradient system using a C-4 vydac column in water/acetonitrile (0.1% trifluoroacetic acid) on a Waters system. At the end of purification, the pure fractions were then analyzed in analytical HPLC, and fractions of interest were pooled together and lyophilized in 10% acetic acid solution. The final purified peptides listed in Table 5 were then identified using mass spectrometry (Campus Chemical Instrumentation Center, The Ohio State University, Columbus, Ohio).

TABLE 5

Peptide Sequences of PD-1

| Peptides | Amino Acid Sequence of PD-1 Peptides |
|---|---|
| PD-1 (32-50) | H₂N-VLNWYRMSPSNQTDKLAAF-CONH₂ (SEQ ID NO: 2) |
| AC-PD-1 (32-50) | CH₃CONH-VLNWYRMSPSNQTDKLAAF-CONH₂ (SEQ ID NO: 2) |
| MVF-PD-1 (32-50) | KLLSLIKGVIVHRLEGVE-GPSL-VLNWYRMSPSNQTDKLAAF-CONH₂ (SEQ ID NO: 8) |
| PD-1 (45-64) | H₂N-KLAAFPEDRSQPGQDCRFR-CONH₂ (SEQ ID NO: 3) |
| AC-PD-1 (45-64) | CH₃CONH-KLAAFPEDRSQPGQDCRFR-CONH₂ (SEQ ID NO: 2) |
| MVF-PD-1 (45-64) | KLLSLIKGVIVHRLEGVE-GPSL-KLAAFPEDRSQPGQDCRFR-CONH₂ (SEQ ID NO: 9) |
| PD-1 (73-90) | H₂N-DFHMSVVRARRNDSGTYL-CONH₂ (SEQ ID NO: 4) |
| AC-PD-1 (73-90) | CH₃CONH-DFHMSVVRARRNDSGTYL-CONH₂ (SEQ ID NO: 4) |
| MVF-PD-1 (73-90) | KLLSLIKGVIVHRLEGVE-GPSL-DFHMSVVRARRNDSGTYL-CONH₂ (SEQ ID NO: 10) |
| PD-1 (92-110) | H₂N-GAISLAPKAQIKESLRAEL-CONH₂ (SEQ ID NO: 5) |

TABLE 5-continued

Peptide Sequences of PD-1

| Peptides | Amino Acid Sequence of PD-1 Peptides |
|---|---|
| AC-PD-1 (92-110) | $CH_3CONH$-GAISLAPKAQIKESLRAEL-$CONH_2$ (SEQ ID NO: 5) |
| MVF-PD-1 (92-110) | KLLSLIKGVIVHRLEGVE-GPSL-GAISLAPKAQIKESLRAEL-$CONH_2$ (SEQ ID NO: 11) |

3. Example 3: Binding Specificity of PD-1 Peptides by BIACORE™ a) BIACORE™ Immobilization

To test the activity of all the selected peptides, surface plasmon resonance (SPR) spectroscopy (BIACORE™ T200, at 258C) was used to measure their binding affinities to the extracellular domain of human PD-L1 (hPD-L1). Recombinant hPD-L1 ectodomain was immobilized onto the gold surface of a CM5 sensor chip by direct amine coupling. To confirm that the immobilized hPD-L1 ectodomain was functional, its affinity to the recombinant human PD-1 (hPD-1) ectodomain was checked.

To obtain theoretical maximum response upon peptide binding, calculated immobilization amount of rhPD-L1, Nivolumab and human IgG is 9790 RU, 14286 RU and 14286 RU respectively. 20 µg/ml of rhPD-L1 at 10 mM NaAc pH 5.5, Nivolumab at 10 mM HEPES, pH 7.5 and human IgG at 10 mM HEPES, pH 7.0 was injected over chip after activation with EDC/NHS for 7 min at 10 µl/min. The resulting immobilization levels for rhPD-L1 (FIG. 3A), Nivolumab (FIG. 3B), Human IgG (FIG. 3C) are 2345 RU, 12264 RU and 11651 RU respectively.

b) Specificity of rhPD-1 and Nivolumab Binding Test

126. To validate prepared sensor chip, 1 µM (17.3 µg/ml) rhPD-1 was injected over the chip for 3 min at 10 µl/min (FIG. 3D). 1 µM BSA was used as the negative control. The chip was regenerated by 10 mM Glycine-HCl, pH 2.5(FIG. 3E). It can be seen upon rhPD-1 injection Nivolumab generated strong signal with response (3740 RU), and rhPD-L1 caused weak signal (461 RU), while human IgG didn't show any binding signal. BSA didn't lead to any binding, indicating PD-1 binding to Nivolumab and rhPD-L1 is specific.

c) Specificity of PD-1 Peptide Binding to rPD-L1 and Nivolumab by BIACORE™

1 µM of various PD-1 peptides were injected over the chip for 1 min at 10 µl/min followed by 1 min dissociation and then 1 min regeneration with 10 mM Glycine-HCl, pH 2.5 for each run. FIG. 4A shows that MVF-PD-1 (45-64), MVF-PD-1 (73-90), MVF-PD-1 (92-110) bind to immobilized rhPD-L1, resulting in around 110 RU. In contrast, MVF-PD-1(32-50) exhibits very weak binding (11 RU), which is similar to the negative control, MVF-HER-2(266-296) (20 RU). The same three positive MVF-peptides revealed stronger binding to Nivolumab, 1030 RU, 1000 RU, 970 RU respectively (FIG. 4B). Again the MVF-PD-1 (32-50) showed negligible binding capacity (20 RU) indicating that this sequence does not represent a viable epitope. It was concluded that MVF-PD-1 (45-64, 73-90 and 92-110) were able to recognize both rhPD-L1 and Nivolumab, while MVF-PD-1(31-49) does not. Additionally, the acetylated peptides also bind to rhPD-L1 and Nivolumab, albeit more weakly than the chimeric MVF peptides (FIG. 4C-4D). The free peptides also bind both PD-L1 and nivolumab, PD-1 (73-90) shows much stronger binding to rhPD-L1 and Nivolumab than PD-1 (45-64) and PD-1 (92-110) (FIG. 4E, 4F). PD-1(45-64) is the second stronger binder. Therefor binding efficiency of free peptides can be ranked as: 73-90>46-64>92-110. From these binding studies, it can be concluded that the PD-1 peptides 46-64, 73-90 and 92-110 can recognize the rPD-L1 and can act as small peptide inhibitors of PD-1:PD-L1 interaction.

4. Example 4: Immunogenecity Testing of PD-1 Peptides in Rabbits a) MVF-PD-1 Peptides Elicit High Tittered Anti-Peptide Antibodies.

The four PD-1 sequences were synthesized as chimeric constructs with a promiscuous T helper epitope derived from the measles virus fusion protein (MVF, amino acids 288-302). The vaccine constructs 1 mg of peptide were emulsified in Montanide ISA 720 (Seppic, Paris, France) and nor-MDP adjuvant (N-acetyl-glucosamine-3 yl-acetyl L-alanyl-D-isoglutamine) and used to immunize New Zealand white rabbits purchased from Charles River Laboratories, Wilmington, Mass. and housed in The Ohio State University's University Laboratory Animal Resources (ULAR) facilitates. Rabbits were vaccinated for a total of three times at three weeks interval. Animals were bled weekly and sacrificed at nine weeks and terminal bled by cardiac puncture at the time of the last test bleed. All experiments were performed in accordance with the U.S. Public Health Service Policy on Humane Care and Use of Laboratory Animals and approved by the Ohio State University Institutional Animals Care and Use Committee and detailed in the accepted protocol. Peptide vaccine antibodies were purified by affinity chromatography using a protein A/G column and the concentration was measured by Coomassie protein assay.

All four epitopes elicited high-titered antibodies >250, 000 against the immunizing vaccine FIG. 5A. The terminal bleed antibodies also recognized the recombinant human PD-1 protein as well as the immunizing peptide MVF-PD-1, acetylated peptide, and free peptide FIG. 5B.

b) (ii) Homology Between Human and Mouse PD-1 Sequence of Chosen Epitopes.

There is 65% overall homology between human and mouse PD-1 sequence. The chosen epitopes show between 67%-74% homology between the human and mouse sequence. Thus, it was important to see whether the chosen human epitopes can bind mouse PD-1 to validate the mice studies.

c) (iii) α-hPD-1 Rabbit Polyclonal Antibodies Bind to Mouse PD-1

To determine whether α-hPD-1 rabbit polyclonal antibodies recognize murine PD-1, splenocytes from naïve myelin basic protein (MBP)-specific TCR transgenic mice were activated with MBP Ac1-11 for 72 h. PD-1 expression was analyzed by flow cytometry. As shown in FIG. 6, all four polyclonal α-hPD-1 antibodies bound to mouse PD-1 validating the use of the human PD-1 in the tumor mouse studies.

d) (iv) The Regulation of T Cell Proliferation by α-Hu PD-1 Antibodies

Antigen specific T cell proliferation reflects important effector function of T effector cells. To determine whether the four α-huPD-1 antibodies alter T effector function by activating or inhibiting PD-1 signaling pathway, CFSE-based proliferation assays were performed (FIG. 7). Briefly, splenocytes from naïve MBP-specific TCR transgenic mice were labeled with CFSE and activated with MBP Ac1-11 in the presence of 50 mg/ml of α-huPD-1 antibodies or control rabbit IgG for 4 days. CFSE expression was analyzed by flow cytometry. The data show that 81% of α-hPD-1-92-110 treated CD4 T cells are highly proliferating compared to only 70% of T cells are highly proliferating in control IgG treated group, indicating α-hPD-1-92-110 blocks PD-1/PD-L1 interaction and leads to enhanced T effector function represented by increased antigen-specific proliferation of myelin-specific CD4 T cells. Contrarily, α-hPD-1(45-64) or α-hPD-1(73-90) treated T cells show decreased proliferation, indicating that they activate PD-1 signaling and inhibit the effector function of myelin-specific CD4 T cells. Additionally, α-hPD-1(32-50) has no effects on T effector function because the cells treated with α-huPD-1(32-50) proliferate at the same level as the cells treated with control IgG. Together, these data indicate α-hPD-1(92-110) enhances T effector function and has therapeutic capability in inhibiting tumor growth in vivo. The 45-64 and 73-90 epitopes by virtue of their property of activating PD-1 signaling can serve as a target for autoimmune diseases.

5. Example 5: Immunogenicity Testing of PD-1 Peptides in Immunocompetent Mice and Tumor Challenge Experiments a) Mice Vaccination and Tumor Challenge Protocols.

Immunocompetent Balb/c mice of 6-8 weeks of age were purchased from Charles River Laboratories, Wilmington, Mass. and housed in The Ohio State University's University Laboratory Animal Resources (ULAR) facilities. Isoflurane was used to anaesthetize the animals before cells injection and termination. Pre-immune sera samples were taken from the mice then they were immunized with 100 μg of peptide emulsified in Montanide ISA 720 (Seppic, Paris, France) and nor-MDP adjuvant (N-acetyl-glucosamine-3 yl-acetyl L-alanyl-D-isoglutamine). Mice received booster immunizations 3 and 6 weeks after the first. Several test sera samples were taken from the mice (FIG. 8).

b) Tumor Challenge:

10 days after the second boost, mice were inoculated with $1 \times 10_5$ murine colon carcinoma CT26 tumor cells subcutaneous on the right flank. Tumor growth was monitored three times a week and sera samples were taken weekly and upon sacrifice of the animal. Control mice on day 0 were engrated with $1 \times 10_5$ CT26 tumor cells subcutaneous and received. The animals received 150 μg injections of anti-mouse antibodies directed against PD-1. Mice were monitored and scored for the formation of palpable tumors twice weekly and sacrificed if tumors became necrotic or exceeded the predetermined size of 2,000 mm3. Tumor diameters were measured twice a week. Tumor size was calculated according to the formula: V=[(length ×width2)/2]. Tumor volumes were measured in cubic millimeters with calipers and calculated with the following formula: A×B2×0.5, where A is the largest diameter, and B is the smallest diameter. All experiments were performed in accordance with the U.S. Public Health Service Policy on Humane Care and Use of Laboratory Animals and approved by the Ohio State University Institutional Animals Care and Use Committee and detailed in the accepted protocol c) Immunogenicity of PD-1 Vaccine Constructs in Mice.

All individual mice mounted a robust antibody response to all 4 vaccines. The immune response (FIG. 9 and Table 6) to pooled sera were monitored at various intervals (2Y+1, 2Y+3, 3Y+1, 3Y+2, 3Y+3) against the vaccine constructs.

TABLE 6

Antigenicity of terminal bleeds in rabbits and mouse against recombinant hu PD-1 protein

|  | Terminal Mouse Sera 1:100 | Terminal Mouse Sera 1:200 | Terminal Rabbit Sera 1:100 | Terminal Rabbit Sera 1:200 | Purified Anti-body 100 μg/ml | Purified Anti-body 50 μg/ml |
|---|---|---|---|---|---|---|
| Control Peptide | − | − | − | − |  |  |
| PD-1 (32-50) | − | − | +++ | ++ |  |  |
| PD-1 (45-64) | +++++ | ++++ | ++++ | +++ |  |  |
| PD-1 (73-90) | +++ | ++ | − | − |  |  |
| PD-1 (93-110) | ++ | ++/− | ++++ | +++ |  |  |
| Erbetux |  |  |  |  | − | − |
| Nivolomab |  |  |  |  | +++ | +++ |
| Pertuzumab |  |  |  |  | ++++ | ++++ |

Terminal Mouse and Rabbit sera were tested for reactivity to recombinant huPD1 protein 600 ng/well. Sera were tested at 1:100 and 1:200 dilutions. ABTS was used as a substrate in the assay. Samples were read at 415λ and scored d) Immune Cell Detection in Mice Tissues The tumor and tumor draining lymph nodes were collected for subsequent FACS analysis to study the immune response in mice. Cells suspensions were prepared from tissues either by mechanistic dissociation or by enzymatic digestion. The stained cells were analyzed with a LSR II flow cytometer (BD Biosciences) equipped with 3 excitation lasers at wavelengths 405, 488 and 633 nm. CD8+ T cells and CD4+CD25+ T cells from tumor leucocytes were purified either on a MACS column or FACSAria.

e) Immune-Profiling of T Cell Responses in Treated Mice

Flow cytometric analysis was performed to evaluate the expression of surface markers (CD45, CD3, CD4, CD8 and CD25) and transcription factor FoxP3 in splenocytes and tumor infiltrating T cells. Briefly, spleens were removed from mice and pressed through cell strainers, followed by a short incubation with red blood cells lysis buffer to lyse the red blood cells. Cells were then collected, washed, and resuspended in staining buffer (1% BSA in PBS). Similarly, tumors were removed from mice and pressed through cell strainers, followed by one wash with 37% percoll. The tumor cells were then washed with PBS and resuspended in staining buffer. The splenocytes and tumor cells were incubated with mAbs to the cell-surface markers for 30 min at 4° C. After washing twice with staining buffer, cells were fixed and permeabilized using Cytofix/Cytoperm solution for 60 min at 4° C. Cells were stained for FoxP3 for 30 min at 4° C. 80,000-100,000 live cell events were acquired on a FACSCanto (BD) and analyzed using FlowJo software (Tree Star, Inc.). To differentiate infiltrating cells from tumor cells, the tumor cells were first gated on CD45+ cells. Then the CD3+CD4+ and CD3+CD8+ cells were analyzed. Tregs were represented by CD4+CD25+FoxP3+ cells. As shown in FIG. 10 A, CD4 and CD8 subsets are at similar levels in spleen, while group C, E and F showed increased Treg population in spleen compared to Group A (negative control). In tumors, Group C has the highest Tregs compared to the other four groups (FIG. 10 B), indicating peptide PD1-45-64 vaccination led to increased Treg development in tumor microenvironment. Group E had the lowest Treg.

f) Efficacy Studies in Syngeneic Balb/c Mice Immunized with PD-1 Constructs and Challenged with $1 \times 10_5$ Murine Colon Carcinoma CT26 Tumor Cells FIG. 11 shows the individual Plots of tumor growth in mice (5/group) for each of the four PD-1 constructs A: (PD-1(32-50), B: PD-1 (45-64), C: PD-1 (73-90) and D: PD-1 (92-110), control peptide (E: irrelevant peptide) and a positive control group (F) treated with anti-mouse PD-1 monoclonal antibody.

g) Mouse Tumor Growth Data Preliminary Statistical Analysis

To assess performance of 4 different vaccine treatments on tumor growth, tumor size was measured periodically in mice, and the results were compared to those of positive and negative controls. There were 5 mice in each treatment group, each receiving the assigned MVF-peptide and then being inoculated with 1e5 CT26 (colon) tumor cells 10 days after the final boost of the treatment. Day 14 was considered the primary time point of interest, as the investigators believed waiting until day 19 allowed the tumors too much time to grow, resulting in similar sizes at that point of the experiment. Tumor size was measured in three ways: LWW (½*length*width*width) at all time points, LWH (½*length*width*height) at all time points, and terminal tumor weight at the end of the study. The mice treated with MVF-PD-a(45), group C, were sacrificed before day 19 due to the death of one mouse, so the comparisons can only be made between tumor size at day 14. Tumor size is in units of mm3 for LWW and LWH and grams for terminal tumor weight.

Due to small sample sizes in each group and inability to assume normality, the exact Wilcoxon rank-sum test was used to check for systematic differences between the distributions of tumor size at times 14 days and 19 days (FIGS. 12A-D and Tables 7-10). P-values given are for test comparing that column's control to the respective treatment, and are two-sided to account for the possibility of tumor size being systematically larger or smaller between treatment and control. As this is preliminary data, the p-values are not adjusted for multiple comparisons. Overall, there were few instances of significant differences between the distributions of a control and a treatment.

TABLE 7

Comparison of MVF-PD-1 (32-50) median size to control sizes

| Measure | MVF-PD (32-50) | MVF Uptase (control) | Anti-PD-1 Mab (+ control) |
| --- | --- | --- | --- |
| LWW, Day 14 | 486 | 405 (p = 0.5873) | 445.5 (p = 0.2698) |
| LWH, Day 14 | 420 | 367.5 (p = 1.0000) | 297 (p = 0.6429) |
| LWW, Day 19 | 1080 | 850.5 (p = 0.2381) | 1183 (p = 1.0000) |
| LWH, Day 19 | 900 | 850.5 (p = 0.3095) | 1056 (p = 1.0000) |
| Terminal wt. | 0.92 | 1.4 (p = 0.3095) | 1.04 (p = 0.4524) |

For MVF-PD-a(32), there were no significant differences in the distributions of tumor size between the treatment and either the positive or negative controls.

TABLE 8

Comparison of MVF-PD-1 (45-64) median size to control sizes

| Measure | MVF-PD (45-64) | MVF Uptase (control) | Anti-PD-1 Mab (+ control) |
| --- | --- | --- | --- |
| LWW, Day 14 | 550 | 405 (p = 0.4524) | 445.5 (p = 0.2619) |
| LWH, Day 14 | 448 | 367.5 (p = 0.8889) | 297 (p = 0.2857) |

For MVF-PD-1(45-64), as noted before comparisons could only be done for data at day 14. Here, there were no significant differences in tumor size distribution found between this treatment and either of the controls.

TABLE 9

Comparison of MVF-PD-1 (73-90) median size to control sizes

| Measure | MVF-PD (73-90) | MVF Uptase (control) | Anti-PD-1 Mab (+ control) |
| --- | --- | --- | --- |
| LWW, Day 14 | 405 | 405 (p = 1.0000) | 445.5 (p = 0.3413) |
| LWH, Day 14 | 346.5 | 367.5 (p = 0.8413) | 297 (p = 0.8968) |
| LWW, Day 19 | 968 | 850.5 (p = 0.8889) | 1183 (p = 0.1746) |
| LWH, Day 19 | 768 | 850.5 (p = 1.0000) | 1056 (p = 0.0556) |
| Terminal wt. | 0.93 | 1.4 (p = 0.3095) | 1.04 (p = 0.4206) |

For MVF-PD-1(73-90), there were no significant differences between tumor size distributions between this treatment and either control at day 14. There was a noticeably small p-value (<0.1) for LWH at day 19 when comparing the treatment to the positive control, indicating a possible difference in tumor size distributions.

TABLE 10

Comparison of MVF-PD-1 (92-110) median size to control sizes

| Measure | MVF-PD (92-110) | MVF Uptase (control) | Anti-PD-1 Mab (+ control) |
|---|---|---|---|
| LWW, Day 14 | 384 | 405 (p = 0.6667) | 445.5 (p = 0.0952) |
| LWH, Day 14 | 270 | 367.5 (p = 0.2302) | 297 (p = 0.0794) |
| LWW, Day 19 | 1080 | 850.5 (p = 0.4603) | 1183 (p = 0.3333) |
| LWH, Day 19 | 819 | 850.5 (p = 1.0000) | 1056 (p = 0.2222) |
| Terminal wt. | 1.1 | 1.4 (p = 0.4127) | 1.04 (p = 0.9841) |

For MVF-PD-1(92-110), there were also noticeably small p-values when comparing this treatment to the positive control using both LWW and LWH measures. The treatment appeared to have a distribution of systematically smaller tumor sizes than the positive control.

6. Example 6: PD-1 Peptide Antibodies are Inhibitory or Activating

Antigen specific T cell proliferation reflects important effector function of T effector cells. To determine whether the four α-huPD-1 antibodies alter T effector function by activating or inhibiting PD-1 signaling pathway, a CFSE-based proliferation assay was performed. In Proliferation assay splenocytes from naïve MBP-specific TCR transgenic mice were labeled with CFSE and activated with MBP Ac1-11 in the presence of 50 mg/ml of α-huPD-1 antibodies or control rabbit IgG for 4 days. CFSE expression was analyzed by flow cytometry (FIG. 13). The data show that 81% of α-hPD-1-92-110 treated CD4 T cells are highly proliferating compared to only 70% of T cells are highly proliferating in control IgG treated group, indicating α-hPD-1-92-110 blocks PD-1/PD-L1 interaction and leads to enhanced T effector function represented by increased antigen-specific proliferation of myelin-specific CD4 T cells. Contrarily, α-hPD-1(45-64) or α-hPD-1(73-90) treated T cells show decreased proliferation, indicating they activate PD-1 signaling and inhibit the effector function of myelin-specific CD4 T cells. Together, these data indicate α-hPD-1(92-110) enhances T effector function and can have therapeutic potential in inhibiting tumor growth in vivo. The 45-64 and 73-90 epitopes by virtue of their property of activating PD-1 signaling can serve as a target for autoimmune diseases.

7. Example 7: Preliminary Screening Efficacy Studies in Syngeneic Balb/c Mice Immunized with Different PD-1 Constructs and Challenged with 1×10$^5$ Murine Colon Carcinoma CT26 Tumor Cells Immunocompetent Balb/c mice (5 mice/gp) of 6-8 weeks of age were immunized with 100 µg of peptide emulsified in Montanide ISA 720 (Seppic, Paris, France) and nor-MDP adjuvant (N-acetyl-glucosamine-3 yl-acetyl L-alanyl-D-isoglutamine). Mice received booster immunizations 3 and 6 weeks Tumor Challenge: 10 days after the second boost, mice were inoculated with 1×10$^5$ murine colon carcinoma CT26 tumor cells subcutaneous and tumor growth was monitored three times a week. Control mice on day 0 were engrafted with 1×10$^5$ CT26 tumor cells subcutaneous and received 150 µg injections of anti-mouse antibodies directed against PD-1. The immune response (FIG. 14) to pooled sera were monitored at various intervals. (2Y+1, 2Y+3, 3Y+1, 3Y+2, 3Y+3) against the vaccine constructs and against the recombinant PD-1 protein (Table 11). All individual mice mounted a robust antibody response to all 4 vaccines.

TABLE 11

| Mouse/rabbit sera | Mouse 1:100 | Mouse 1:200 | Rabbit 1:100 | Rabbit 1:200 |
|---|---|---|---|---|
| Control Peptide | − | − | − | − |
| PD-1(32-50) | − | − | +++ | ++ |
| PD-1(45-64) | +++++ | ++++ | ++++ | +++ |
| PD-1(73-90) | +++ | ++ | − | − |
| PD-1(92-110) | ++ | ++/− | ++++ | +++ |

Terminal Mouse and Rabbit sera were tested for reactivity to recombinant huPD1 protein 600 ng/well. Sera were tested at 1:100 and 1:200 dilutions. ABTS was used as a substrate in the assay.
Samples were read at 415λ and scored

8. Example 8: Validation of PD-1 (92-110) Epitope as a Vaccine Candidate

All vaccinated mice showed high immunogenicity developing high titers of antibodies to the respective immunogens. Only mice vaccinated with MVF-PD-1(92-110) showed significant inhibition of tumor growth at Day 14 (FIG. 15) indicating that this epitope is a useful inhibitory vaccine. This conclusion is further validated by the studies that showed that epitope 45-64 and 73-90 are not inhibitory and therefore enhance tumor growth. On the other hand the mouse PD1 mAb (29F.1A12) which is a positive control should have inhibited tumor growth. It was conclude that only the PD-1 (92-110) epitope is a prime candidate for a vaccine as that epitope was designed based on binding properties to Nivolumab.

9. Example 9: Efficacy of Combination PD-1 and HER-2 Vaccine Constructs in Syngeneic Balb/c Mice Challenged with 1×10$^5$ Murine Colon Carcinoma CT26/HER-2 Tumor Cells (Scheme FIG. 16)

The rationale for this study is whether the well-established HER-2 vaccine in combination with a PD-1(92-110) vaccine can potentiate/increase immunogenicity, enhance anti-tumor responses and provide synergistic benefit in inhibiting tumor growth in a syngeneic cancer model. Balb/c mice (10 mice/gp) were immunized with combination of MVF-PD-1 (92-110), MVF-HER-2 (266-296), and MVF-HER-2 (597-626) peptide vaccine constructs emulsified with nor-MDP and ISA 720. Animals were boosted twice at 3 weeks interval. Antibody titers were determined by ELISA. on 200 ng/well of MVF-peptide.

Two weeks after the final boost 1×10$^5$ tumor cells from CT26/HER-2 tumor lines were transplanted s.c. Control mice either were challenged with 1×10$^5$ tumor cells and treated with anti-PD-1 antibody (29F.1A12) twice a week for the duration of the experiment. Tumor burden was determined by measuring the tumors once they had reached a palpable size using calipers. CT-26/HER-2 tumor bearing mice were sacrificed 21 days after transplantation. Blood and tissue samples were collected from these mice at the time of sacrifice and a final weight was taken of the excised tumor mass. Sera concentrations from 1:100-1:512,000 were tested. ABTS was used as a substrate in the assay the enzyme reaction was stopped after 10 minutes with a 0.1% SDS solution. Titers were defined as the final dilution that still had an absorbance >than 0.200 when read at 415 nm. Sera samples 1Y+3, 2Y+1, 2Y+3, and 3Y+2 were taken before CT-26 HER-2 neu tumor challenge. Samples 3Y+3 and 3Y+5 were taken at 1 week and 3 weeks post challenge respectively. Robust HER-2 and PD-1 antibody responses were elicited in all vaccinated mice (FIG. 17).

Individual Plots of tumor growth in syngeneic Balb/c mice (10/gps) immunized 3 times at 3 week intervals with PD-1 (92-110) alone or in combination with immunization two Her2 peptide immunogens. An immunization control group immunized with irrelevant peptide was included. Mice were challenged 15 days after 3rd vaccination with CT-26 Her2 neu carcinoma cells ($1 \times 10^5$). Control mice were also challenged with the CT-26 Her2 neu carcinoma cells. Control mice were treated twice weekly IP with anti-Ms PD-1 MAb (Positive control) or PBS (Negative control). Mice were monitored and scored for the formation of palpable tumors, then tumor dimensions were measured regularly using calipers. Animals were sacrificed on day 21 after tumor cell transplantation. Error bars are a representation of standard error for the group of mice and p-values compare various groups to triple vaccine mice. The results indicate that the triple vaccination is effective in reducing tumor growth in a Balb/c syngeneic model of colon carcinoma versus either the PD-1 vaccine or more importantly the positive control gold standard: anti-mouse PD-1 monoclonal antibody (29F.1A12) (FIG. 18).

The data demonstrate that the triple vaccination group MVF-PD-1 (92-110)+MVF-HER-2 (266+296)+MVF-HER-2 (597-626) were more effective in preventing tumor growth against the positive control anti-mouse PD-1 Mab (29F.1A12) or vaccination with MVF-PD-1 alone (FIGS. 19A and 19B). Thus, the strategy of triple vaccination with the combo HER-2 and PD-1 peptides is a viable proposition that demonstrates synergistic/additivity culminating in enhanced immunogenicity and inhibition of tumor growth.

10. Example 10: PD-1 Vaccines are Safe and do not Exhibit Toxicity or Autoimmunity All mice vaccinated over a period of 9 weeks showed no signs of scruffiness, lesions, and lethargy. Organs (spleen, liver, heart, lung, kidney, and tumor) from the Balb/c mice vaccinated with combination peptides (HER-2 and PD-1) were collected from mice and submitted for analysis at the Comparative Pathology & Mouse. Phenotyping Core facility of the Comprehensive cancer center department of Veterinary Biosciences (Pathologist: Krista M. D. La Perle, DVM, PhD, Dipl. ACVP). No significant lesions were noted in any of the organs submitted for histologic evaluation. There were also no overt biochemical abnormalities noted. All mice had hepatocellular vacuolation consistent with glycogenosis. Glycogen accumulation in the liver is interpreted to be a normal finding, and varies depending on the physiological state of the animal. Glycogen accumulation can also be observed as a manifestation of toxicity or with glycogen storage diseases.

11. Example 11: Combination Peptide Vaccine Significantly Increased CD8/Treg Ratio in Tumor Infiltrating Cells (TILs)

$CD25^+FoxP3^+CD4$ T regulatory cells (Tregs) are one of the major suppressive populations in tumor microenvironment that contributes significantly to the development of an immunosuppressive tumor microenvironment (TME). On the other hand, high numbers of T cells at the tumor site, especially CD8 T cells, is a key denominator for overall survival (OS) in cancer patients. A high CD8/Treg ratio has been associated with favorable prognosis in cancer. Therefore, it was determined CD8/Treg ratio in TIC in tumor-bearing mice vaccinated with combination peptides or control peptide (described above). Tumors were removed from four groups of mice (described above) and pressed through cell strainers, followed by two washes with 37% percoll. The cells were then incubated with mAbs to the cell-surface markers (CD45, CD4, CD8, CD25 Then the cells were fixed and permeabilized using Cytofix/Cytoperm solution (ebioscience) for 60 min at 4° C., followed by staining for FoxP3 for 30 min at 4° C. 80,000-100,000 live cell events were acquired on a FACSCantoII (BD) and analyzed using FlowJo software (Tree Star, Inc.). To differentiate TILs from tumor cells, the cells were first gated on $CD45^+$ cells. Then the $CD4^+$ (FIG. 20A) and $CD8^+$ (FIG. 20B) cells were analyzed. Tregs were represented by $CD4^+CD25^+FoxP3^+$ cells (FIG. 20C). GraphPad software (GraphPad Prism Software, Inc., San Diego, Calif., USA) was utilized for statistical analysis. Group means were calculated and compared with Anova. CD8+ T cells were significantly higher in combination vaccine group (HER-2/PD1-92 vaccinated group) compared to control peptide-vaccinated group (FIG. 20B). There are no significant differences of CD4 T cells or Treg cells among all groups (FIGS. 20A and 20B). However, the CD8/Treg ratio is significantly higher in combination vaccine group compared to control peptide-vaccinated group (FIG. 20D). Therefore, these data indicate an increased CD8/Treg ratio in HER-2/PD-1 vaccinated group compared to control peptide-vaccinated group) for 30 min at 4

12. Example 12: Analysis of Tumor Infiltrating Lymphocytes from Peptide-Vaccinated Mice A high CD8/Treg ratio has been associated with favorable prognosis in cancer. To determine whether peptide vaccine increases CD8/Treg ratio, CD8+, CD4+ and T regulatory (FoxP3+CD25+CD4+) tumor infiltrating lymphocytes were analyzed in peptide-vaccinated mice. Flow cytometric analysis was performed to evaluate the expression of surface markers (CD45, CD4, CD8 and CD25) and the expression of transcription factor FoxP3 was determined by intracellular staining (FIG. 21A). Briefly, tumors were removed from mice and pressed through cell strainers, followed by two washes with 37% percoll. The cells were then resuspended in staining buffer and incubated with mAbs to the cell-surface markers for 30 min at 4° C. After washing twice with staining buffer, cells were fixed and permeabilized using Cytofix/Cytoperm solution (ebioscience) for 60 min at 4° C. Cells were then stained for FoxP3 for 30 min at 4° C. 80,000-100,000 live cell events were acquired on a FACSCanto II (BD) and analyzed using FLOWJO™ software (Tree Star, Inc.). To differentiate infiltrating cells (CD45+) from tumor cells (CD45−), the total cells were first gated on CD45+ cells. Then the percentage of CD4+ and CD8+ cells in CD45+ tumor infiltrating population were analyzed. Tregs were represented by FoxP3+CD25+CD4+ cells. GraphPad software (GraphPad Prism Software, Inc., San Diego, Calif., USA) was utilized for statistical analysis. Group means were calculated and compared with Anova. As shown in FIG. 21B CD8+ T cells were significantly higher in PD-1 peptide or PD-1/Her-2 vaccinated groups (group 1 and 2) compared to control peptide-vaccinated group (group 3). However, there were no significant differences in Treg cells among PD-1 peptide, PD-1/Her-2 vaccinated group and control peptide-vaccinated group. Together, these data indicate an increased CD8/Treg ratio in PD-1 peptide or PD-1/Her-2 vaccinated groups compared to control peptide-vaccinated group.

E. REFERENCES

Allen S D, Rawale S V, Whitacre C C, Kaumaya P T. Therapeutic peptidomimetic strategies for autoimmune diseases: costimulation blockade. J Pept Res. 2005; 65(6): 591-604.

Allen, S. D., et al., Peptide vaccines of the HER-2/neu dimerization loop are effective in inhibiting mammary tumor growth in vivo. J Immunol, 2007. 179(1): p. 472-82.

Arteaga C L, Engelman J A. ERBB receptors: from oncogene discovery to basic science to mechanism-based cancer therapeutics. Cancer cell. 2014; 25(3):282-303. Epub 2014 Mar. 22.

Baras, A. S., et al., The ratio of CD8 to Treg tumor-infiltrating lymphocytes is associated with response to cisplatin-based neoadjuvant chemotherapy in patients with muscle invasive urothelial carcinoma of the bladder. Oncoimmunology, 2016. 5(5): p. e1134412.

Baselga J, Arteaga C L. Critical update and emerging trends in epidermal growth factor receptor targeting in cancer. J Clin Oncol. 2005; 23(11):2445-59. Epub 2005/03/09.

Baselga J, Swain S M. Novel anticancer targets: revisiting ERBB2 and discovering ERBB3. Nature reviews Cancer. 2009; 9(7):463-75. Epub 2009/06/19.

Baselga J. Targeting tyrosine kinases in cancer: the second wave. Science. 2006; 312(5777):1175-8. Epub 2006/05/27.

Brahmer J R, Tykodi S S, Chow L Q, Hwu W J, Topalian S L, Hwu P, Drake C G, Camacho L H, Kauh J, Odunsi K, Pitot H C, Hamid O, Bhatia S, Martins R, Eaton K, Chen S, Salay T M, Alaparthy S, Grosso J F, Korman A J, Parker S M, Agrawal S, Goldberg S M, Pardoll D M, Gupta A, Wigginton J M. Safety and activity of anti-PD-L1 antibody in patients with advanced cancer. The New England journal of medicine. 2012; 366(26):2455-65.

Chames P, Van Regenmortel M, Weiss E, Baty D. Therapeutic antibodies: successes, limitations and hopes for the future. Br J Pharmacol. 2009; 157(2):220-33.

Chou P Y, Fasman G D. Prediction of the secondary structure of proteins from their amino acid sequence. Advances in enzymology and related areas of molecular biology. 1978; 47:45-148.

Cobleigh M A, Langmuir V K, Sledge G W, Miller K D, Haney L, Novotny W F, Reimann J D, Vassel A. A phase I/II dose-escalation trial of bevacizumab in previously treated metastatic breast cancer. Seminars in oncology. 2003; 30(5 Suppl 16):117-24.

Dakappagari N K, Douglas D B, Triozzi P L, Stevens V C, Kaumaya P T. Prevention of mammary tumors with a chimeric HER-2 B-cell epitope peptide vaccine. Cancer Res. 2000; 60(14):3782-9.

Dakappagari N K, Lute K D, Rawale S, Steele J T, Allen S D, Phillips G, Reilly R T, Kaumaya P T. Conformational HER-2/neu B-cell epitope peptide vaccine designed to incorporate two native disulfide bonds enhances tumor cell binding and antitumor activities. J Biol Chem. 2005; 280(1):54-63.

Dakappagari N K, Pyles J, Parihar R, Carson W E, Young D C, Kaumaya P T. A chimeric multi-human epidermal growth factor receptor-2 B cell epitope peptide vaccine mediates superior antitumor responses. J Immunol. 2003; 170(8):4242-53. Epub 2003/04/12.

Dakappagari N K, Sundaram R, Rawale S, Liner A, Galloway D R, Kaumaya P T. Intracellular delivery of a novel multiepitope peptide vaccine by an amphipathic peptide carrier enhances cytotoxic T-cell responses in HLA-A*201 mice. J Pept Res. 2005; 65(2):189-99. Epub 2005/02/12.

deLeeuw, R. J., et al., The prognostic value of FoxP3+ tumor-infiltrating lymphocytes in cancer: a critical review of the literature. Clin Cancer Res, 2012. 18(11): p. 3022-9.

Eskens F A, Verweij J. The clinical toxicity profile of vascular endothelial growth factor (VEGF) and vascular endothelial growth factor receptor (VEGFR) targeting angiogenesis inhibitors; a review. European journal of cancer. 2006; 42(18):3127-39. Epub 2006/11/14.

Folkman J. Tumor angiogenesis: therapeutic implications. The New England journal of medicine. 1971; 285(21): 1182-6.

Foy K C, Liu Z, Phillips G, Miller M, Kaumaya P T. Combination treatment with HER-2 and VEGF peptide mimics induces potent anti-tumor and anti-angiogenic responses in vitro and in vivo. J Biol Chem. 2011; 286(15):13626-37. Epub 2011/02/18.

Foy K C, Miller M J, Moldovan N, Carson W E, Kaumaya PTP. Combined vaccination with HER-2 peptide followed by therapy with VEGF peptide mimics exerts effective anti-tumor and anti-angiogenic effects in vitro and in vivo. OncoImmunology. 2012; 1(7):0-1.

Foy K C, Vicari D, Kaumaya PTP. Therapeutic Peptides Targeting HER-2/neu and VEGF Signaling Pathways in Breast Cancer. Handbook of Biologically Active Peptides 2013. p. 612-6.

Garrett, J. T., et al., Novel engineered trastuzumab conformational epitopes demonstrate in vitro and in vivo antitumor properties against HER-2/neu. J Immunol, 2007. 178(11): p. 7120-31.

Grothey A. Recognizing and managing toxicities of molecular targeted therapies for colorectal cancer. Oncology (Williston Park). 2006; 20(14 Suppl 10):21-8. Epub 2007/03/16.

Hadrup, S., M. Donia, and P. Thor Straten, Effector CD4 and CD8 T cells and their role in the tumor microenvironment. Cancer Microenviron, 2013. 6(2): p. 123-33.

Hamid O, Robert C, Daud A, Hodi F S, Hwu W J, Kefford R, Wolchok J D, Hersey P, Joseph R W, Weber J S, Dronca R, Gangadhar T C, Patnaik A, Zarour H, Joshua A M, Gergich K, Elassaiss-Schaap J, Algazi A, Mateus C, Boasberg P, Tumeh P C, Chmielowski B, Ebbinghaus S W, Li X N, Kang S P, Ribas A. Safety and tumor responses with lambrolizumab (anti-PD-1) in melanoma. The New England journal of medicine. 2013; 369(2):134-44.

Harding F A, Stickler M M, Razo J, DuBridge R B. The immunogenicity of humanized and fully human antibodies: residual immunogenicity resides in the CDR regions. mAbs. 2010; 2(3):256-65.

Hoeben A, Landuyt B, Highley M S, Wildiers H, Van Oosterom A T, De Bruijn E A. Vascular endothelial growth factor and angiogenesis. Pharmacol Rev. 2004; 56(4):549-80.

Hopp T P, Woods K R. Prediction of protein antigenic determinants from amino acid sequences. Proceedings of the National Academy of Sciences of the United States of America. 1981; 78(6):3824-8.

Houck K A, Ferrara N, Winer J, Cachianes G, Li B, Leung D W. The vascular endothelial growth factor family: identification of a fourth molecular species and characterization of alternative splicing of RNA. Molecular endocrinology. 1991; 5(12):1806-14. Epub 1991/12/01.

Hynes N E, Lane H A. ERBB receptors and cancer: the complexity of targeted inhibitors. Nature reviews Cancer. 2005; 5(5):341-54.

Ishida Y, Agata Y, Shibahara K, Honjo T. Induced expression of PD-1, a novel member of the immunoglobulin gene superfamily, upon programmed cell death. The EMBO journal. 1992; 11(11):3887-95.

Iwai Y, Ishida M, Tanaka Y, Okazaki T, Honjo T, Minato N. Involvement of PD-L1 on tumor cells in the escape from host immune system and tumor immunotherapy by PD-L1 blockade. Proceedings of the National Academy of Sciences of the United States of America. 2002; 99(19): 12293-7.

Jain R K, Duda D G, Clark J W, Loeffler J S. Lessons from phase III clinical trials on anti-VEGF therapy for cancer. Nat Clin Pract Oncol. 2006; 3(1):24-40.

Karplus P A, Schulz G E. Refined structure of glutathione reductase at 1.54 A resolution. Journal of molecular biology. 1987; 195(3):701-29.

Kaumaya P T, Foy K C, Garrett J, Rawale S V, Vicari D, Thurmond J M, Lamb T, Mani A, Kane Y, Balint C R, Chalupa D, Otterson G A, Shapiro C L, Fowler J M, Greyer M R, Bekaii-Saab T S, Carson W E, 3rd. Phase I active immunotherapy with combination of two chimeric, human epidermal growth factor receptor 2, B-cell epitopes fused to a promiscuous T-cell epitope in patients with metastatic and/or recurrent solid tumors. J Clin Oncol. 2009; 27(31):5270-7.

Kaumaya P T. A paradigm shift: Cancer therapy with peptide-based B-cell epitopes and peptide immunotherapeutics targeting multiple solid tumor types: Emerging concepts and validation of combination immunotherapy. Human vaccines & immunotherapeutics. 2015; 11(6): 1368-86.

Kaumaya P T. Could precision-engineered peptide epitopes/vaccines be the key to a cancer cure? Future Oncol. 2011; 7(7):807-10.

Kaumaya P T P, Kobs-Conrad S, DiGeorge A M, Stevens V. Denovo Engineering of Protein Immunogenic & Antigenic Determinants. In: Anantharamaiah GMB, C., editor. PEPTIDES: Springer-Verlag.; 1994. p. 133-64.

Kaumaya PTP. HER-2/neu cancer vaccines: Present status and future prospects. International Journal of Peptide Research and Therapeutics. 2006; 12(1):65-77.

Kyte J, Doolittle R F. A simple method for displaying the hydropathic character of a protein. Journal of molecular biology. 1982; 157(1):105-32.

Li B, Ogasawara A K, Yang R, Wei W, He G W, Zioncheck T F, Bunting S, de Vos A M, Jin H. KDR (VEGF receptor 2) is the major mediator for the hypotensive effect of VEGF. Hypertension. 2002; 39(6):1095-100. Epub 2002/06/08.

Lynch M P, Kaumaya PTP. Advances in HTLV-1 peptide vaccines and therapeutics. Current Protein and Peptide Science. 2006; 7(2):137-45.

Miller M J, Foy K C, Kaumaya P T. Cancer immunotherapy: present status, future perspective, and a new paradigm of peptide immunotherapeutics. Discovery medicine. 2013; 15(82):166-76. Epub 2013 Apr. 3.

Miller M J, Foy K C, Kaumaya PTP. Cancer immunotherapy: Present status, future perspective, and a new paradigm of peptide immunotherapeutics. Discovery medicine. 2013; 15(82):166-76.

Motzer R J, Rini B I, McDermott D F, Redman B G, Kuzel T M, Harrison M R, Vaishampayan U N, Drabkin H A, George S, Logan T F, Margolin K A, Plimack E R, Lambert A M, Waxman I M, Hammers H J. Nivolumab for Metastatic Renal Cell Carcinoma: Results of a Randomized Phase II Trial. Journal of clinical oncology: official journal of the American Society of Clinical Oncology. 2015; 33(13):1430-7.

Nelson A L, Dhimolea E, Reichert J M. Development trends for human monoclonal antibody therapeutics. Nature reviews Drug discovery. 2010; 9(10):767-74.

Novotny J, Handschumacher M, Haber E, Bruccoleri R E, Carlson W B, Fanning D W, Smith J A, Rose G D. Antigenic determinants in proteins coincide with surface regions accessible to large probes (antibody domains). Proceedings of the National Academy of Sciences of the United States of America. 1986; 83(2):226-30.

Oshima R G, Lesperance J, Munoz V, Hebbard L, Ranscht B, Sharan N, Muller W J, Hauser C A, Cardiff R D. Angiogenic acceleration of Neu induced mammary tumor progression and metastasis. Cancer Res. 2004; 64(1):169-79. Epub 2004/01/20.

Preston, C. C., et al., The ratios of CD8+ T cells to CD4+CD25+ FOXP3+ and FOXP3− T cells correlate with poor clinical outcome in human serous ovarian cancer. PLoS One, 2013. 8(11): p. e80063.

Rizvi N A, Mazieres J, Planchard D, Stinchcombe T E, Dy G K, Antonia S J, Horn L, Lena H, Minenza E, Mennecier B, Otterson G A, Campos L T, Gandara D R, Levy B P, Nair S G, Zalcman G, Wolf J, Souquet P J, Baldini E, Cappuzzo F, Chouaid C, Dowlati A, Sanborn R, Lopez-Chavez A, Grohe C, Huber R M, Harbison C T, Baudelet C, Lestini B J, Ramalingam S S. Activity and safety of nivolumab, an anti-PD-1 immune checkpoint inhibitor, for patients with advanced, refractory squamous non-small-cell lung cancer (CheckMate 063): a phase 2, single-arm trial. The Lancet Oncology. 2015; 16(3):257-65.

Rose G D, Geselowitz A R, Lesser G J, Lee R H, Zehfus M H. Hydrophobicity of amino acid residues in globular proteins. Science. 1985; 229(4716):834-8.

Roskoski R, Jr. The ErbB/HER family of protein-tyrosine kinases and cancer. Pharmacological research: the official journal of the Italian Pharmacological Society. 2014; 79:34-74. Epub 2013 Nov. 26.

Sharma P, Allison J P. The future of immune checkpoint therapy. Science. 2015; 348(6230):56-61.

Shinohara T, Taniwaki M, Ishida Y, Kawaichi M, Honjo T. Structure and chromosomal localization of the human PD-1 gene (PDCD1). Genomics. 1994; 23(3):704-6.

Srinivasan M, Gienapp I E, Stuckman S S, Rogers C J, Jewell S D, Kaumaya P T, Whitacre C C. Suppression of experimental autoimmune encephalomyelitis using peptide mimics of CD28. J Immunol. 2002; 169(4):2180-8. Epub 2002/08/08.

Srinivasan M, Wardrop R M, Gienapp I E, Stuckman S S, Whitacre C C, Kaumaya P T. A retro-inverso peptide mimic of CD28 encompassing the MYPPPY motif adopts a polyproline type II helix and inhibits encephalitogenic T cells in vitro. J Immunol. 2001; 167(1):578-85.

Steele J T, Allen S D, Kaumaya PTP. Cancer Immunotherapy with Rationally Designed Synthetic Peptides. Handbook of Biologically Active Peptides 2006. p. 491-8.

Sundaram R, Dakappagari N K, Kaumaya PTP. Synthetic peptides as cancer vaccines. Biopolymers—Peptide Science Section. 2002; 66(3):200-16.

Thornton J M, Edwards M S, Taylor W R, Barlow D J. Location of 'continuous' antigenic determinants in the protruding regions of proteins. The EMBO journal. 1986; 5(2):409-13.

Topalian S L, Drake C G, Pardoll D M. Immune checkpoint blockade: a common denominator approach to cancer therapy. Cancer cell. 2015; 27(4):450-61.

Topalian S L, Hodi F S, Brahmer J R, Gettinger S N, Smith D C, McDermott D F, Powderly J D, Carvajal R D, Sosman J A, Atkins M B, Leming P D, Spigel D R, Antonia S J, Horn L, Drake C G, Pardoll D M, Chen L, Sharfman W H, Anders R A, Taube J M, McMiller T L, Xu H, Korman A J, Jure-Kunkel M, Agrawal S, McDonald D, Kollia G D, Gupta A, Wigginton J M, Sznol M. Safety, activity, and immune correlates of anti-PD-1 antibody in cancer. The New England journal of medicine. 2012; 366(26):2443-54.

Vicari D, Foy K C, Liotta E M, Kaumaya P T. Engineered Conformation-dependent VEGF Peptide Mimics Are Effective in Inhibiting VEGF Signaling Pathways. J Biol Chem.286(15):13612-25. Epub 2011 Feb. 16.

Wang B, Kaumaya P T, Cohn D E. Immunization with synthetic VEGF peptides in ovarian cancer. Gynecol Oncol. 2010; 119(3):564-70.

Welling G W, Weijer W J, van der Zee R, Welling-Wester S. Prediction of sequential antigenic regions in proteins. FEBS letters. 1985; 188(2):215-8.

Yarden Y, Sliwkowski M X. Untangling the ErbB signalling network. Nature reviews Molecular cell biology. 2001; 2(2):127-37. Epub 2001 Mar. 17.

Zak K M, Kitel R, Przetocka S, Golik P, Guzik K, Musielak B, Domling A, Dubin G, Holak T A. Structure of the Complex of Human Programmed Death 1, PD-1, and Its Ligand PD-L1. Structure. 2015; 23(12):2341-8.

Zhu Z, Witte L. Inhibition of tumor growth and metastasis by targeting tumor-associated angiogenesis with antagonists to the receptors of vascular endothelial growth factor. Investigational new drugs. 1999; 17(3):195-212. Epub 2000 Feb. 9.

| F. Sequences |
|---|
| SEQ ID NO: 1 human PD1 residues 1-128<br>PPTFSPALLVVTEGDNATFTCSFSNTSESFVLNWYRMSPSNQTDKLAAFP<br>EDRSQPGQDCRFRVTQLPNGRDFHMSVVRARRNDSGTYLCGAISLAPKLQ<br>IKESLRAERVTERRAEVPTAHPSPSP |
| SEQ ID NO: 2 PD1 (32-50)<br>VLNWYRMSPSNQTDKLAAF |
| SEQ ID NO: 3 PD1 (45-64)<br>KLAAFPEDRSQPGQDCRFR |
| SEQ ID NO: 4 PD1 (73-90)<br>DFHMSVVRARRNDSGTYL |
| SEQ ID NO: 5 PD1 (92-110)<br>GAISLAPKAQIKESLRAEL |
| SEQ ID NO: 6 Measles virus fusion protein (MVF)<br>KLLSLIKGVIVHRLEGVE |
| SEQ ID NO: 7 Linker<br>GPSL |
| SEQ ID NO: 8 MVF-PD1 (32-50)<br>KLLSLIKGVIVHRLEGVEGPSLVLNWYRMSPSNQTDKLAAF |
| SEQ ID NO: 9 MVF-PD1 (45-64)<br>KLLSLIKGVIVHRLEGVEGPSLKLAAFPEDRSQPGQDCRFR |
| SEQ ID NO: 10 MVF-PD1 (73-90)<br>KLLSLIKGVIVHRLEGVEGPSLDFHMSVVRARRNDSGTYL |
| SEQ ID NO: 11 MVF-PD1 (92-110)<br>KLLSLIKGVIVHRLEGVEGPSLGAISLAPKAQIKESLRAEL |

-continued

| F. Sequences |
|---|
| SEQ ID NO: 12 PD1 (32-50) D PEPTIDE RETRO-INVERSO<br>FAALKDTQNSPSMRWNLV |
| SEQ ID NO: 13 PD1 (45-64) D PEPTIDE RETRO-INVERSO<br>RFRCDQGPQSRDEPFAALK |
| SEQ ID NO: 14 PD1 (73-90) D PEPTIDE RETRO-INVERSO<br>LYTGSDNRRARVVSMHFD |
| SEQ ID NO: 15 PD1 (92-110) D PEPTIDE RETRO-INVERSO<br>LEARLSEKIQAKPALSIAG |
| SEQ ID NO: 16 MVF PD1 (32-50) D PEPTIDE<br>RETRO-INVERSO<br>KLLSLIKGVIVHRLEGVEGPSLFAALKDTQNSPSMRYWNLV |
| SEQ ID NO: 17 MVF PD1 (45-64) D PEPTIDE<br>RETRO-INVERSO<br>KLLSLIKGVIVHRLEGVEGPSLRFRCDQGPQSRDEPFAALK |
| SEQ ID NO: 18 MVF PD1 (73-90) D PEPTIDE<br>RETRO-INVERSO<br>KLLSLIKGVIVHRLEGVEGPSLLYTGSDNRRARVVSMHFD |
| SEQ ID NO: 19 MVF PD1 (92-110) D PEPTIDE<br>RETRO-INVERSO<br>KLLSLIKGVIVHRLEGVEGPSLLEARLSEKIQAKPALSIAG |
| SEQ ID NO: 20 TT<br>NSVDDALINSTIYSYFPSV |
| SEQ ID NO: 21 TT1<br>PGINGKAIHLVNNQSSE |
| SEQ ID NO: 22 P2<br>QYIKANSKFIGITEL |
| SEQ ID NO: 23 P30<br>FNNFTVSFWLRVPKVSASHLE |
| SEQ ID NO: 24 MVF (natural)<br>LSEIKGVIVHRLEGV |
| SEQ ID NO: 25 HBV<br>FFLLTRILTIPQSLN |
| SEQ ID NO: 26 CSP<br>TCGVGVRVRSRVNAANKKPE |
| SEQ ID NO: 27 HER-2 (266-296)<br>LHCPALVTYNTDTFESMPNPEGRYTFGASCV |
| SEQ ID NO: 28 MVF HER-2(266-296)<br>KLLSLIKGVIVHRLEGVEGPSLLHCPALVTYNTDTFESMPNPEGRYTFGA<br>SCV |
| SEQ ID NO: 29 HER-2 (597-626)<br>VARCPSGVKPDLSYMPIWKFPDEEGACQPL |
| SEQ ID NO: 30 MVF HER-2 (597-626)<br>KLLSLIKGVIVHRLEGVEGPSLVARCPSGVKPDLSYMPIWKFPDEEGAC<br>QPL |

What is claimed is:

1. An isolated peptide consisting of the amino acid sequence of SEQ ID NO: 5.

2. A composition comprising the peptide of claim 1 and further comprising a pharmaceutically acceptable vehicle.

3. The composition of claim 2, further comprising an adjuvant.

4. The peptide of claim 1, which is acylated or amidated.

5. An isolated chimeric peptide consisting of the amino acid sequence of SEQ ID NO: 11.

6. An isolated chimeric peptide comprising the amino acid sequence of SEQ ID NO: 11.

7. An isolated chimeric peptide consisting of the amino acid sequence of i) SEQ ID NO: 5; ii) a peptide linker consisting of the amino acid sequence of SEQ ID NO: 7; and iii an amino acid sequence selected from SEQ ID NO: 6, SEQ ID NO: 20, SEQ ID NO: 21, SEQ ID NO: 22, SEQ ID NO: 23, SEQ ID NO: 24, SEQ ID NO: 25, and SEQ ID NO: 26; wherein said amino acid sequence of SEQ ID NO: 7 adjoins the amino acid sequence of SEQ ID NO: 5 to the other amino acid sequence.

8. An isolated chimeric peptide comprising the amino acid sequence of SEQ ID NO: 5 and an amino acid sequence selected from SEQ ID NO: 6, SEQ ID NO: 20, SEQ ID NO: 21, SEQ ID NO: 22, SEQ ID NO: 23, SEQ ID NO: 24, SEQ ID NO: 25, and SEQ ID NO: 26, wherein said amino acid sequences are adjoined via a peptide linker consisting of the amino acid sequence of SEQ ID NO: 7.

9. A method for treating a cancer in a human subject, said method comprising administering to said human subject having cancer a composition comprising a chimeric peptide comprising the amino acid sequence of SEQ ID NO: 5 and an amino acid sequence selected from SEQ ID NO: 6, wherein said amino acid sequences are adjoined via a peptide linker consisting of the amino acid sequence of SEQ ID NO: 7.

10. The method of claim 9, wherein said chimeric peptide comprises SEQ ID NO: 11.

11. The method of claim 9, wherein said composition further comprises an adjuvant.

12. The method of claim 9, wherein said chimeric peptide is acylated or amidated.

13. The method of claim 9, wherein said cancer is breast cancer.

14. The method of claim 9, wherein said cancer is colon cancer.

15. The method of claim 9, wherein said chimeric peptide consists of SEQ ID NO: 11.

* * * * *